US012616736B2

(12) United States Patent
Wright et al.

(10) Patent No.: US 12,616,736 B2
(45) Date of Patent: May 5, 2026

(54) METHOD OF DIAGNOSIS OF ADRENAL INSUFFICIENCY

(71) Applicants: Sheffield Children's NHS Foundation Trust, Sheffield (GB); University of Sheffield, Sheffield (GB)

(72) Inventors: Neil Peter Wright, Sheffield (GB); Charlotte Jane Elder, Sheffield (GB)

(73) Assignees: Sheffield Children's NHS Foundation Trust, Sheffield South Yorkshire (GB); University of Sheffield, Sheffield (GB)

( * ) Notice: Subject to any disclaimer, the term of this patent is extended or adjusted under 35 U.S.C. 154(b) by 384 days.

(21) Appl. No.: 16/650,259

(22) PCT Filed: Oct. 24, 2018

(86) PCT No.: PCT/GB2018/053073
§ 371 (c)(1),
(2) Date: Mar. 24, 2020

(87) PCT Pub. No.: WO2019/081923
PCT Pub. Date: May 2, 2019

(65) Prior Publication Data
US 2020/0268851 A1 Aug. 27, 2020

(30) Foreign Application Priority Data

Oct. 25, 2017 (GB) ..................................... 1717509
Jun. 8, 2018 (GB) ..................................... 1809456

(51) Int. Cl.
| | |
|---|---|
| A61K 38/22 | (2006.01) |
| A61K 9/00 | (2006.01) |
| A61K 47/36 | (2006.01) |
| G01N 33/50 | (2006.01) |

(52) U.S. Cl.
CPC ............ *A61K 38/22* (2013.01); *A61K 9/0043* (2013.01); *A61K 47/36* (2013.01); *G01N 33/50* (2013.01); *G01N 2800/04* (2013.01)

(58) Field of Classification Search
CPC ...... A61K 38/22; A61K 9/0043; A61K 47/36; A61K 49/004; G01N 33/50; G01N 2800/04
USPC ....................................................... 436/128
See application file for complete search history.

(56) References Cited

PUBLICATIONS

Elder et al, Endocrine Abstracts, 2014, 36, OC3.6.*
Elder et al, Endocrine Abstracts, Nov. 2014, vol. 36, abstract OC3.6.*
Hiroi et al, The Journal of Clinical Endocrinology & Metabolism, 2002, 87, 1750-1753.*
Agwu et al, Arch Dis Child, 1999, 80, 330-333.*
Mak et al, Journal of the Endocrine Society, Feb. 2017, 1(2), 96-108.*
Cornes et al., "Salivary Cortisol and Cortisone Responses to Tetracosactrin (Synacthen)," Ann Clin Biochem. 52:606-610, 2015.
Elder et al., "A Novel Non-Invasive Short Synacthen Test," Endocrine Abstracts, Abstract OC3.6, 42$^{nd}$ Meeting of the British Society for Paediatric Endocrinology and Diabetes, Nov. 12-14, 2014, Winchester, UK.
Hiroi et al., "Intranasal Administration of Adrenocorticotropin-(1-24) Adrenocortical Hormone Secretion," J Clin Endocrinol Metabol. 87:1750-1753, 2002.
Illum, "Nasal Drug Delivery—Recent Developments and Future Prospects," J Control. Release 161:254-263, 2012.
Patel et al., "Morning Salivary Cortisol Versus Short Synacthen Test as a Test of Adrenal Suppression," Ann Clin Biochem. 41:408-410, 2004.
Wüthrich et al., "Effect of Formulation Additives Upon the Intranasal Bioavailability of a Peptide Drug: Tetracosactide (ACTH$_{1-24}$)," Pharm Res. 11:278-282, 1994.
Great Britain Combined Search and Examination Report dated Feb. 6, 2018 for GB1717509.2 (7 pages).
International Search Report and Written Opinion mailed on Feb. 13, 2019 for International Application No. PCT/GB2018/053073 (16 pages).
Agwu et al., "Tests of adrenal insufficiency" Arch Dis Child 80:330-333, 1999.

* cited by examiner

*Primary Examiner* — Ganapathy Krishnan
(74) *Attorney, Agent, or Firm* — Klarquist Sparkman, LLP

(57) ABSTRACT

The disclosure relates to a composition comprising adrenocorticotropic hormone (ACTH) or a synthetic ACTH analogue for use in a diagnostic test for adrenal insufficiency. A method to conduct said diagnostic test; a combined diagnostic and method of treatment; and kits comprising the components for said test are also disclosed.

15 Claims, 70 Drawing Sheets

Figures 1, 2:
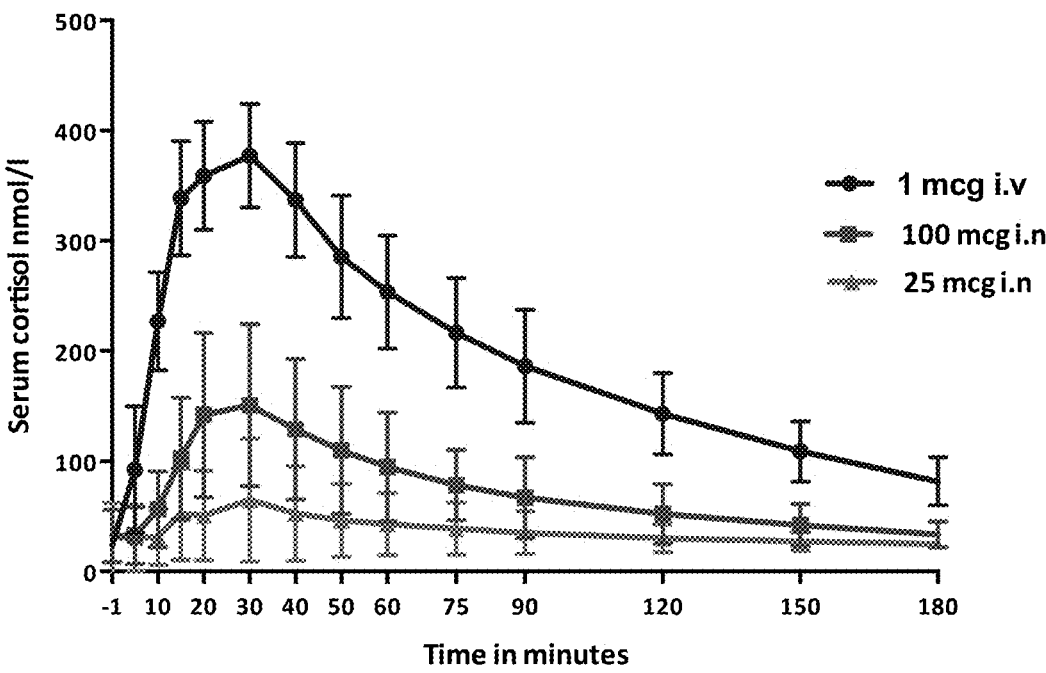
Figure 3A:
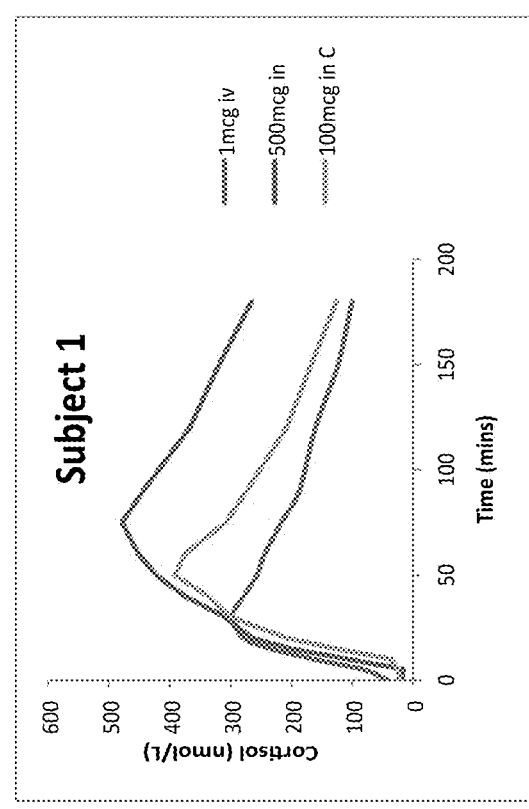
Figure 3A:
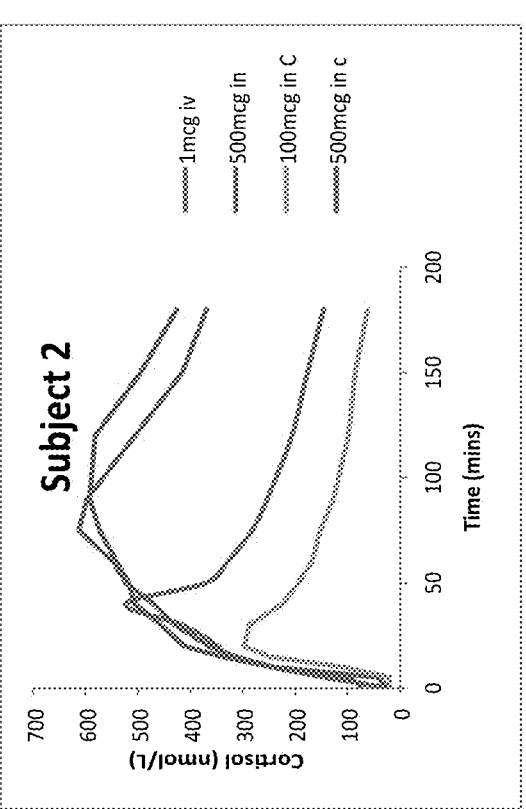
Figure 3A:
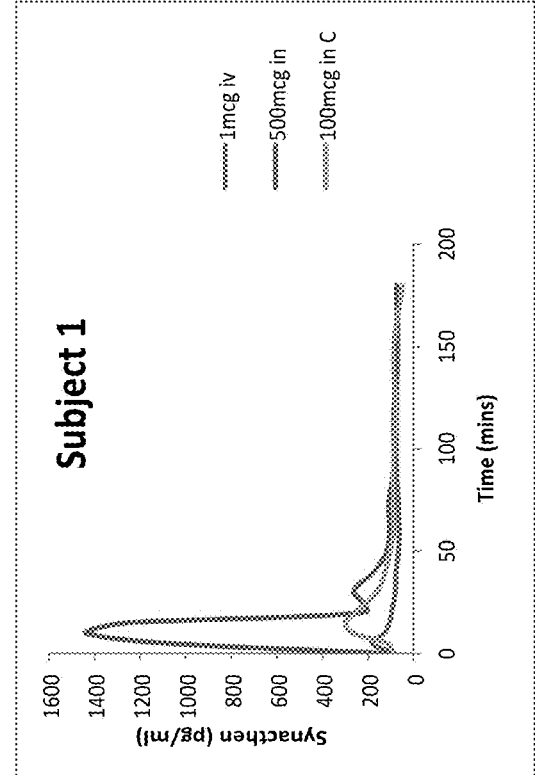
Figure 3A:
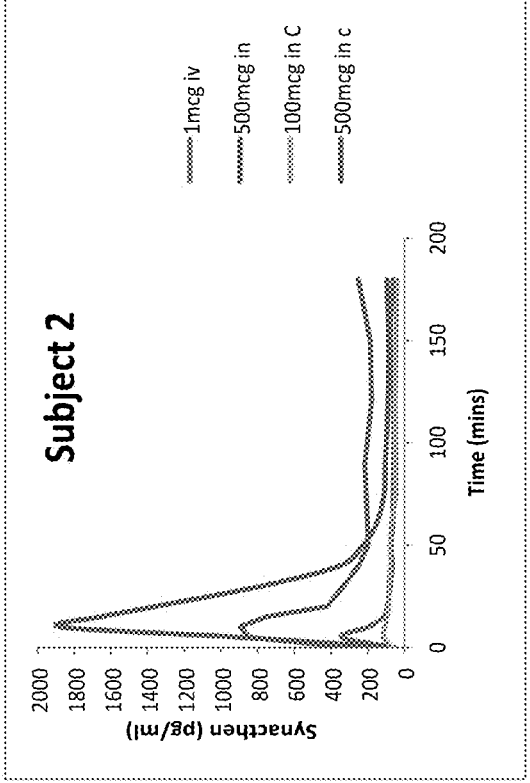
Figure 3B:
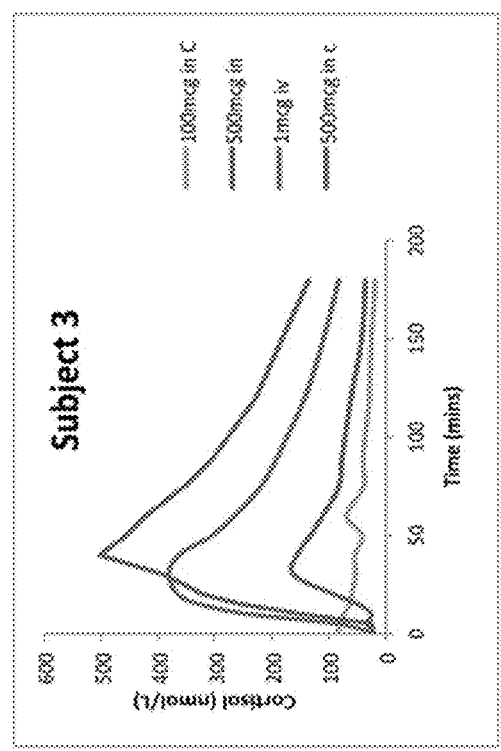
Figure 3B:
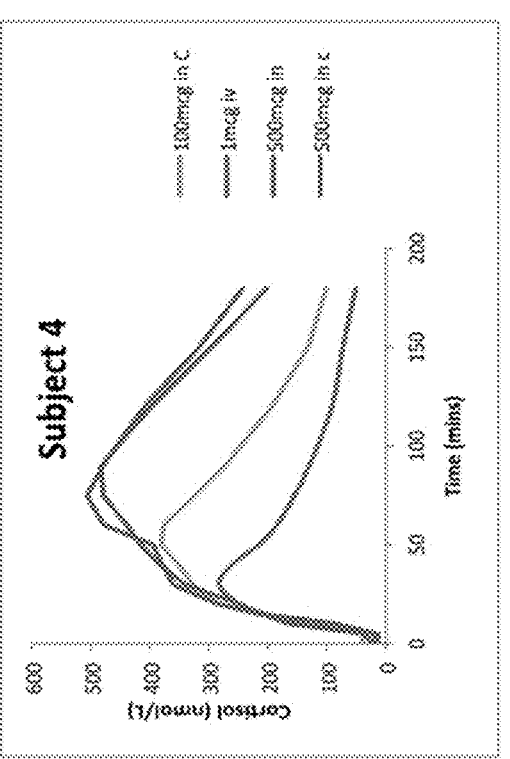
Figure 3B:
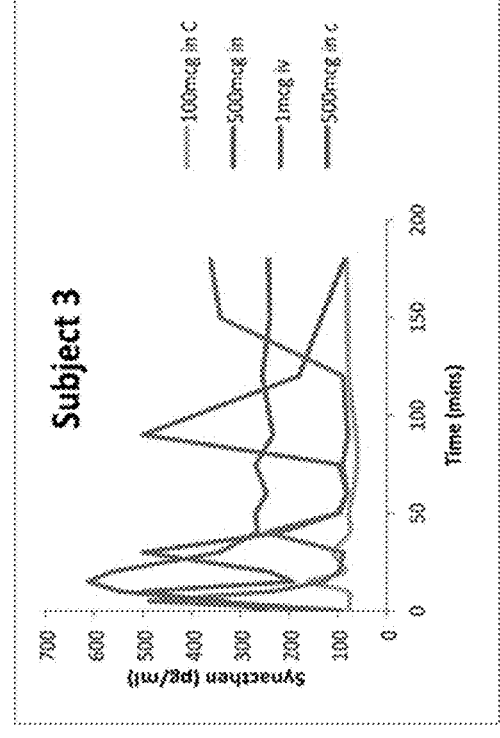
Figure 3B:
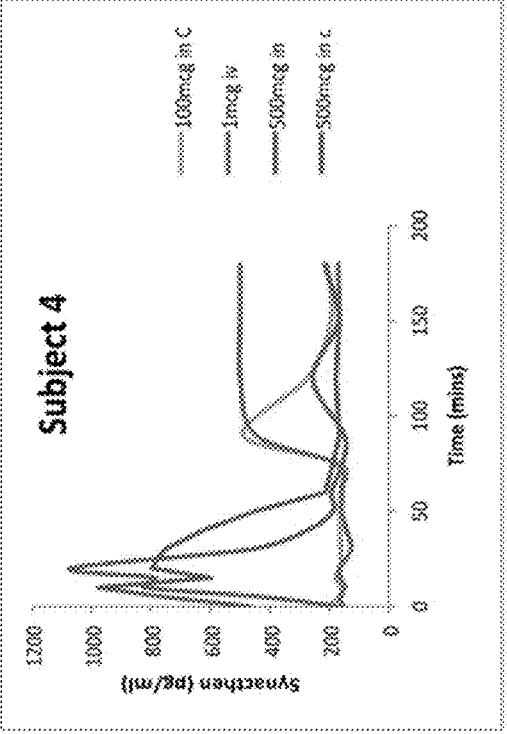
Figure 3C:
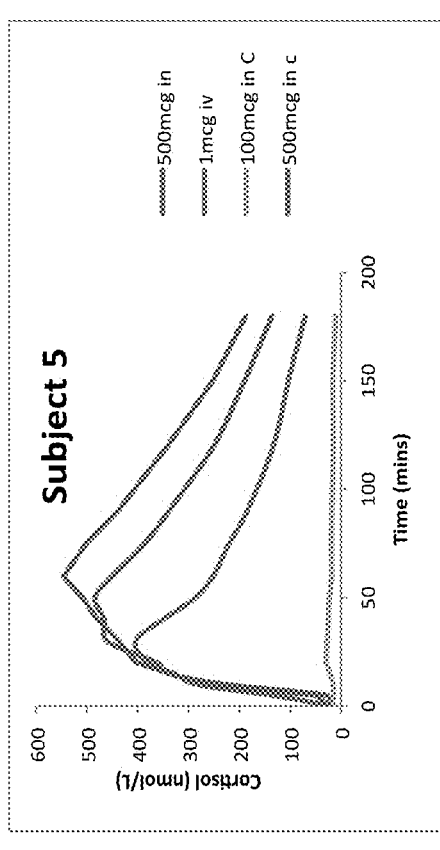
Figure 3C:
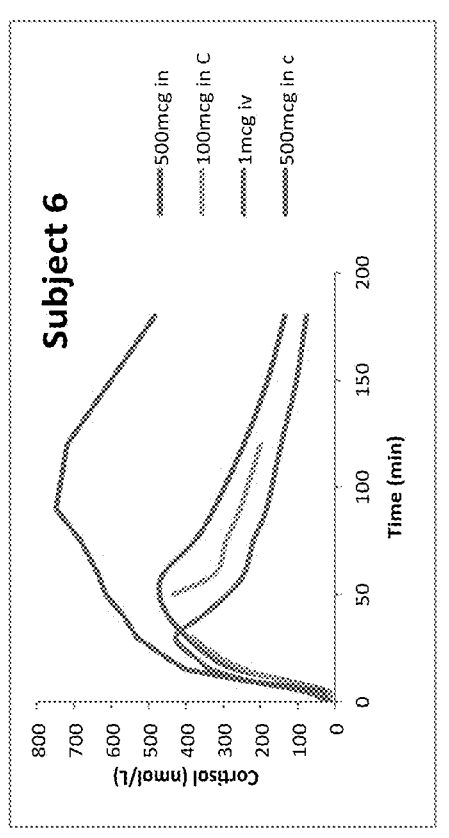
Figure 3C:
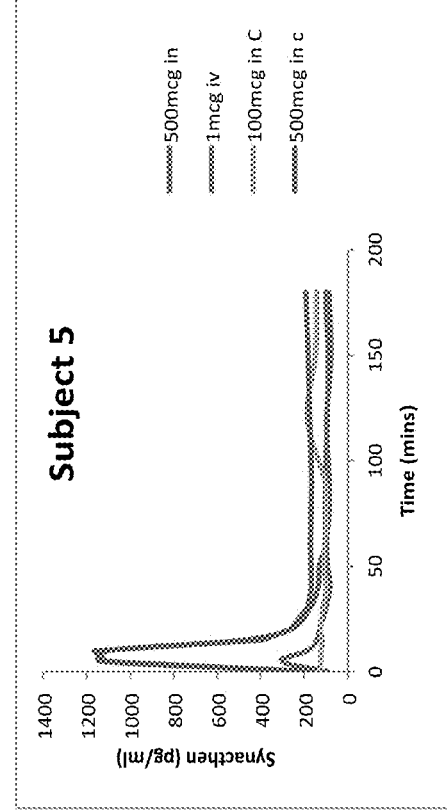
Figure 3C:
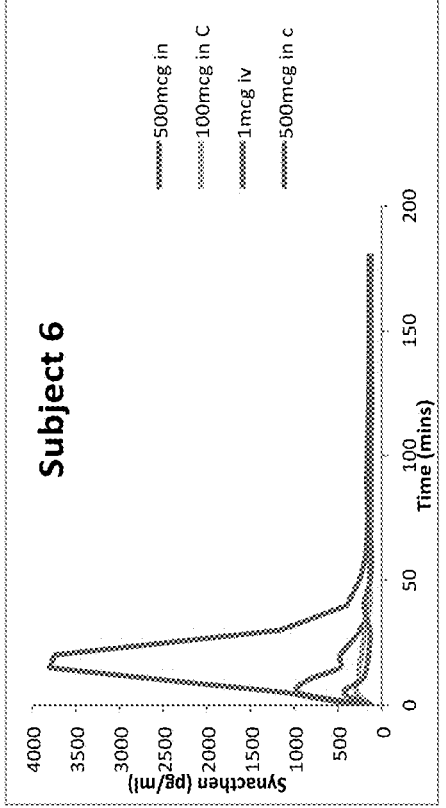
Figure 3D:
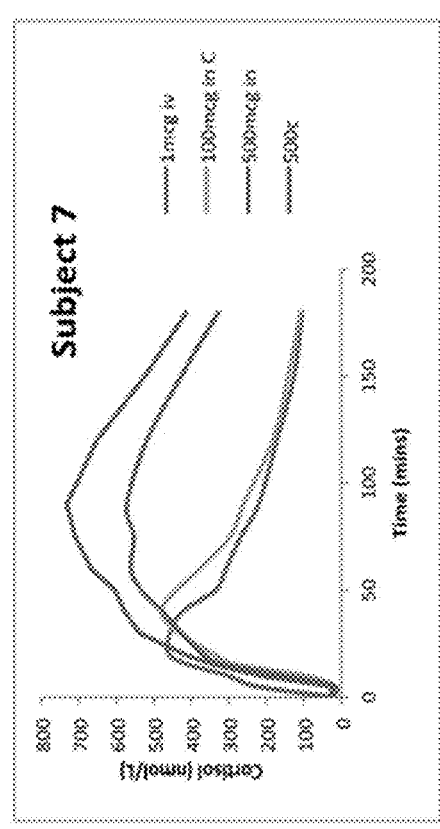
Figure 3D:
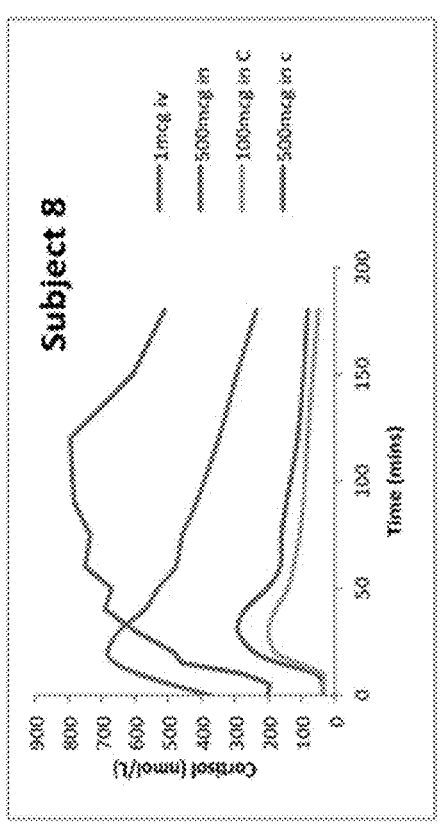
Figure 3D:
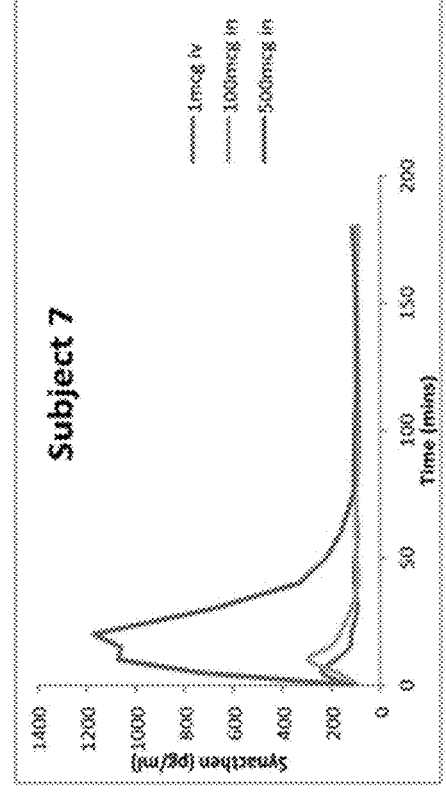
Figure 3D:
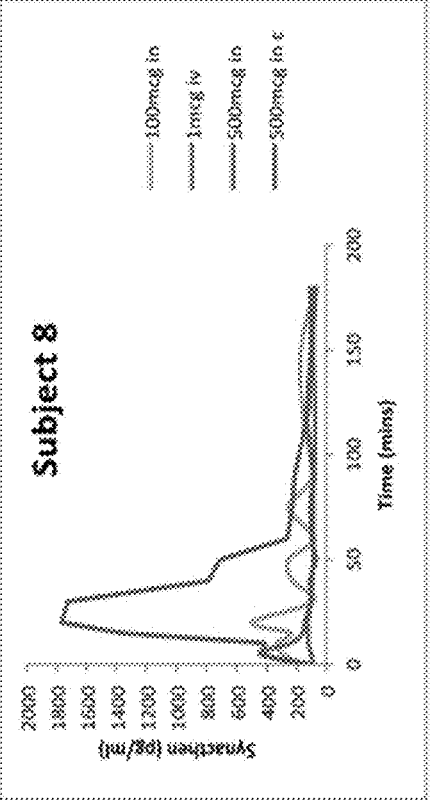
Figure 3E:
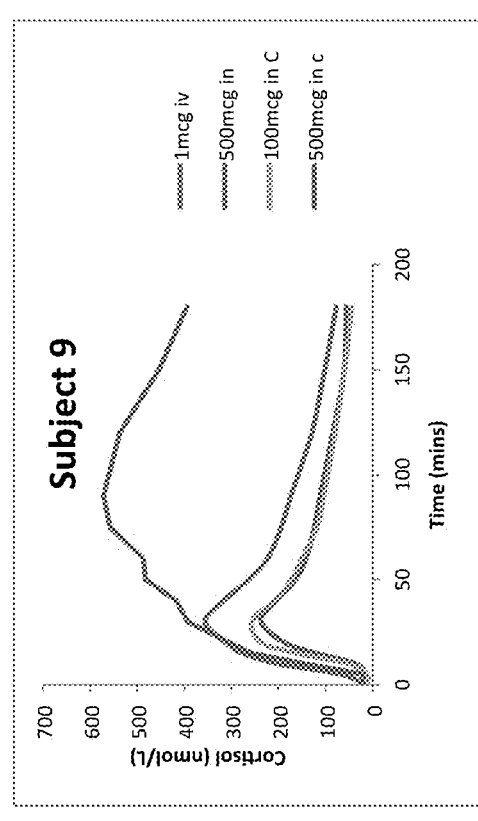
Figure 3E:
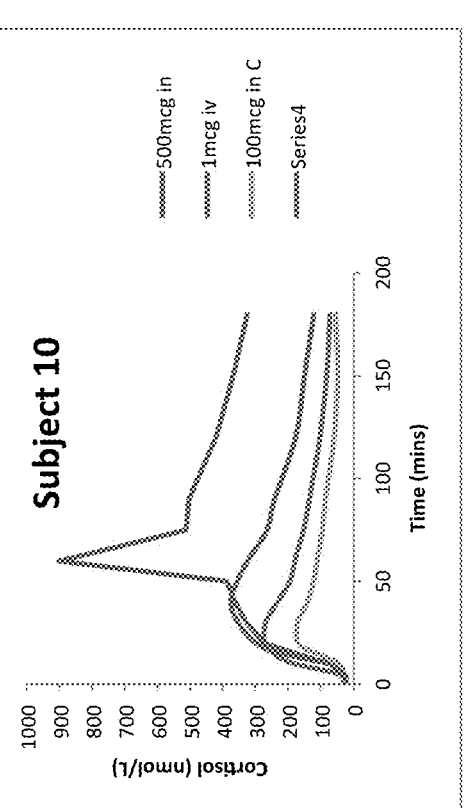
Figure 3E:
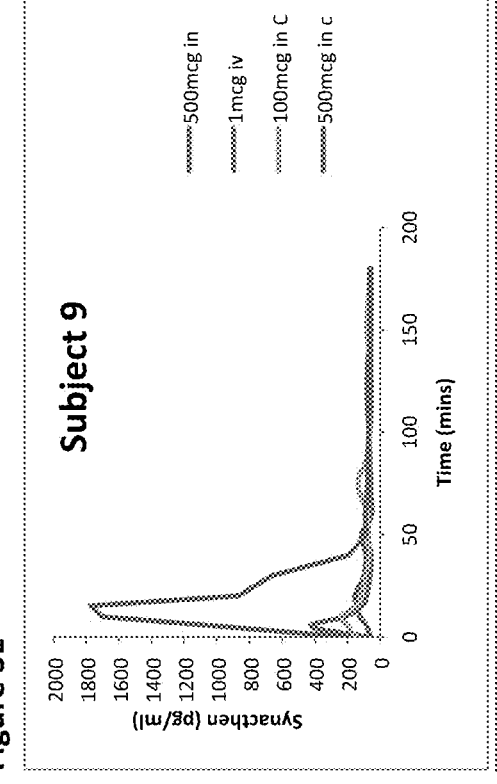
Figure 3E:
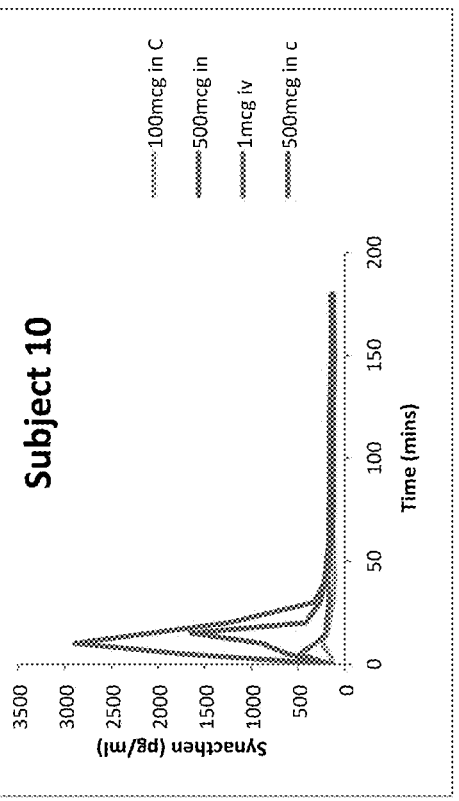
Figure 3F:
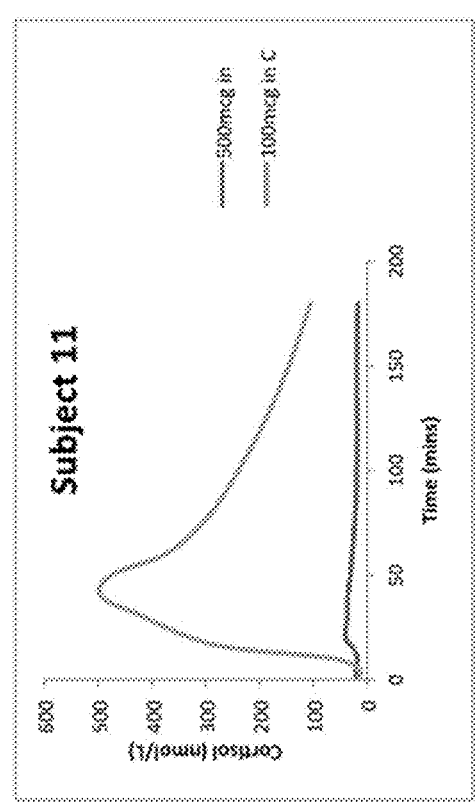
Figure 3F:
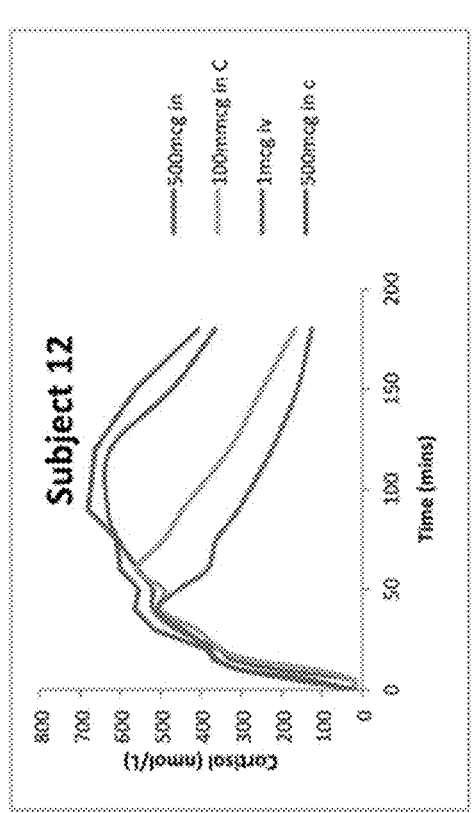
Figure 3F:
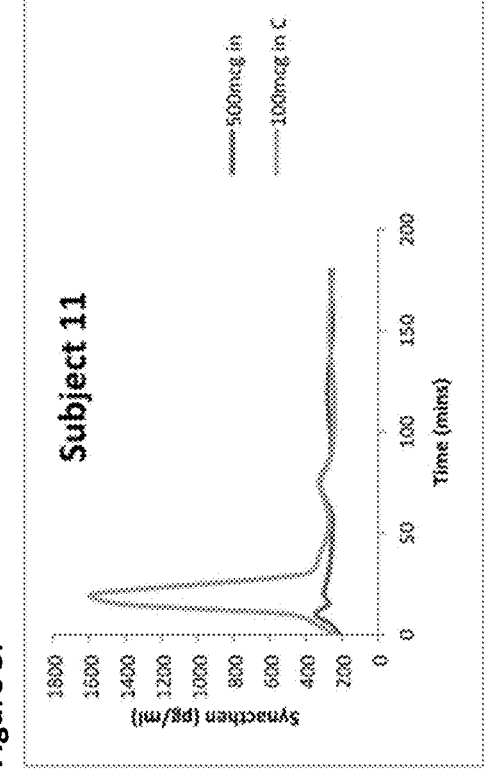
Figure 3F:
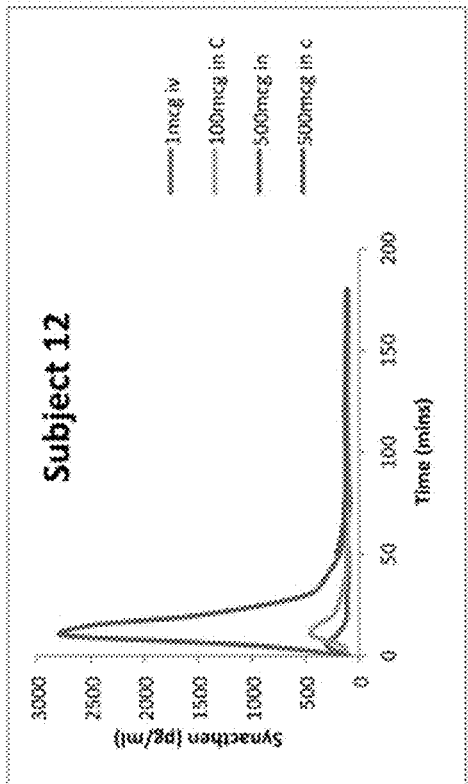

Specification includes a Sequence Listing.

N21B01
N21B02
N21B03
N21B04
N21B05
N21B06
N21B07
N21B08
N21B09
N21B10
N21B11
N21B12

Plasma cortisol concentration (nmol/l)

Time (minutes)

Plasma cortisol concentration (nmol/l)

Time (minutes)

~*~ Adult nasal synacthen 500 mcg + chitosan     ~*~ Adult intravenous synacthen 1 mcg ~*~ Children nasal synacthen 500 mcg + chitosan     ~*~ Children intravenous synacthen 1 mcg ~*~ Adult intravenous synacthen 250 mcg ~*~ Children intravenous synacthen 250 mcg

- ···✱·· Adult nasal synacthen 500 mcg + chitosan
- ─✱─ Children nasal synacthen 500 mcg + chitosan
- ··✱·· Adult intravenous synacthen 1 mcg
- ─✱─ Children intravenous synacthen 1 mcg

- ··✱·· Adult intravenous synacthen 250 mcg
- ─✱─ Children intravenous synacthen 250 mcg

- - • - Adult nasal synacthen 500 mcg + chitosan
- - • - Adult intravenous synacthen 1 mcg
- -•- Children nasal synacthen 500 mcg + chitosan
- -•- Children intravenous synacthen 1 mcg

- - • - Adult intravenous synacthen 250 mcg
- -•- Children intravenous synacthen 250 mcg

SEQUENCE LISTING

<160> NUMBER OF SEQ ID NOS: 1

<210> SEQ ID NO 1
<211> LENGTH: 39
<212> TYPE: PRT
<213> ORGANISM: Homo sapiens

<400> SEQUENCE: 1

```
Ser Tyr Ser Met Glu His Phe Arg Trp Gly Lys Pro Val Gly Lys Lys
1               5                   10                  15

Arg Arg Pro Val Lys Val Tyr Pro Asn Gly Ala Glu Asp Glu Ser Ala
            20                  25                  30

Glu Ala Phe Pro Leu Glu Phe
            35
```

METHOD OF DIAGNOSIS OF ADRENAL INSUFFICIENCY

CROSS REFERENCE TO RELATED APPLICATIONS

This is the U.S. National Stage of International Application No. PCT/GB2018/053073, filed Oct. 24, 2018, which was published in English under PCT Article 21 (2), which in turn claims the benefit of Great Britain Application Nos. 1717509.2, filed Oct. 25, 2017 and 1809456.5, filed Jun. 8, 2018.

FIELD OF THE INVENTION

The disclosure relates to a composition comprising adrenocorticotropic hormone (ACTH) or a synthetic ACTH analogue for use in a diagnostic test for adrenal insufficiency. A method to conduct said diagnostic test by typically administering a hormone or hormone analogue nasally and measuring response with a non-invasive saliva test; kits comprising the components for said test are also disclosed and the use of the diagnostic test and kits in the diagnosis of patients

BACKGROUND TO THE INVENTION

The adrenal glands are above the kidneys and are part of the body's endocrine system. They produce a number of different hormones; those involved in metabolism (cortisol), salt and water balance (aldosterone) and sex steroids (oestrogen and testosterone). Cortisol release is regulated by interaction and feedback with the hormones of the hypothalamus and the anterior pituitary gland. Corticotropin releasing hormone (CRH) produced by the hypothalamus stimulates adrenocorticotropin (ACTH) production in the pituitary gland which in turn stimulates the production of cortisol in the adrenal cortex of the adrenal gland. Cortisol has itself a negative feedback on the hypothalamus and the pituitary gland inhibiting the production of CRH and ACTH.

Cortisol is referred to as a stress hormone and has several other physiological functions such as maintaining blood pressure, regulating protein, carbohydrate and fat metabolism, regulating the effects of insulin and influencing the immune system's inflammatory responses. Adrenal insufficiency is a rare endocrine disorder and can affect people of all ages and sex and is characterised by insufficient production of cortisol (and in some cases aldosterone) causing symptoms such as muscle weakness, loss of weight, low mood, cramps and exhaustion, and has pronounced effects on mental and physical development in children. Adrenal insufficiency (AI) is caused by an impaired function of either i) the adrenal glands (primary adrenal insufficiency), ii) the pituitary gland (secondary adrenal insufficiency) or iii) the hypothalamus (tertiary adrenal insufficiency) and can present with the slow but progressive loss of cortisol (and in some cases aldosterone) resulting in steadily worsening symptoms which, if undiagnosed and not treated with adequate hormone replacement therapy, can ultimately result in adrenal crises, a potential life threatening condition requiring immediate emergency treatment with hydrocortisone.

The most common cause in adults from the developed world is autoimmune destruction of the adrenal gland but worldwide it is tuberculosis. The commonest paediatric cause is the prescription of steroid medication. Adrenal insufficiency is usually permanent but may be transient, especially in children, and therefore periodic diagnostic testing is required in some patients (for example weekly, monthly or 3-monthly).

A diagnosis of adrenal insufficiency can be confirmed by the short synacthen test (SST) using the synthetic analogue of ACTH, tetracosactide, to monitor cortisol production. The test is typically conducted at a hospital where a blood sample is obtained from the patient to determine the amount of cortisol present in the blood. Then a dose of tetracosactide is injected to stimulate the adrenal glands and after a short period of time, such as after 20, 30 and/or 60 min, cortisol levels in the blood are measured again to monitor the response of the adrenal glands to the stimulant. A failure to produce cortisol in response to the stimulant can be indicative of adrenal insufficiency and may provide information of the interaction of hypothalamus, pituitary and adrenal glands.

In recent years requests for SSTs have risen in line with increased paediatric steroid usage and heightened awareness of the adrenal insufficiency steroids can cause. However, although the SST is a common diagnostic method for adrenal insufficiency, cannulation and blood sampling are required making it invasive, time-consuming and resource-intensive, which, when considering children in particular, is not desirable.

The disclosure relates to compositions comprising tetracosactide and chitosan suitable for nasal administration and to a diagnostic test for detecting adrenal insufficiency comprising the delivery of said tetracosactide composition which allows measurement of the cortisol response of a subject in the saliva in a non-invasive manner.

STATEMENT OF THE INVENTION

According to an aspect of the invention there is provided a liquid pharmaceutical composition adapted for nasal administration comprising adrenocorticotropic hormone (ACTH) or a synthetic ACTH analogue, a bioadhesive excipient and including one or more other pharmaceutical excipients.

According to an aspect of the invention there is provided a liquid pharmaceutical composition adapted for nasal administration comprising an effective dose of adrenocorticotropic hormone (ACTH) or a synthetic ACTH analogue, a bioadhesive excipient and including one or more other pharmaceutical excipients for use in a method of diagnosis of adrenal insufficiency in a paediatric subject.

ACTH is used in treatment and as a diagnostic agent. Synthetic forms of ACTH are also available, most notably in the form of tetracosactide which is also known as tetracisactrin, cosyntropin and the acetate ester tetracosactide acetate or tetracisactrin acetate.

The amino acid sequence of ACTH is:

(SEQ ID NO: 1)
SYSMEHFRWGKPVGKKRRPVKVYPNGAEDESAEAFPLEF

Synthetic analogues consist typically of the first 24 amino acids of ACTH and retain full function of the native peptide hormone. Other known analogues consist of the first 17 or 18 amino acids of SEQ ID NO 1 and retain the full function of the native peptide hormone.

In a preferred embodiment of the invention said analogue is tetracosactide, preferably tetracosactide acetate.

Suitably tetracosactide has the molecular formula $C_{136}H_{210}N_{40}O_{31}S$ and a molecular weight of 2933.5 g/mol.

Suitably, said tetracosactide acetate comprises between 4-8 mole of acetic acid per mole of peptide.

Tetracosactide stimulates the release of corticosteroids such as cortisol from the adrenal glands, and is used for the ACTH stimulation test to assess adrenal gland function.

Bioadhesives or mucoadhesives may prolong the residence time of a drug dosage form at the site of absorption, for example the nasal mucosa, and in turn may be able to enhance the absorption and subsequently the efficacy of the drug.

In a preferred embodiment of the invention said bioadhesive is a cationic biopolymer.

In a preferred embodiment of the invention said bioadhesive is chitosan.

Chitosan, is a polysaccharide derived from chitin by partial deacetylation of poly-N-acetyl-D-glucosamine comprising ß-(1→4)-linked 2-acetamido-2-dexoy-D-glucopyranose and ß-(1→4)-linked N-acetyl-D-glucosamine units. Chitosan may facilitate paracellular transport of large polar compounds.

Suitably, said chitosan is deacetylated between 40-90%, more suitably between 50-80%, even more suitably between 60-70%. Suitably said chitosan is deacetylated between 75-90% or 80-90% more suitable chitosan is deacetylated to 80% or more suitably to 90%.

Pharmaceutically acceptable salt forms of chitosan are selected from the group consisting of hydrochloride, lactate, glutamate, maleate, acetate, formate, propionate, malate, malonate, adipate, succinate and nitrate.

In a preferred embodiment said chitosan is chitosan glutamate.

The chitosan glutamate preferably has a molecular weight of between 200000-600000 g/mol. The molecular weight may be more conveniently expressed in terms of the viscosity of a 1% solution of chitosan (or its salt) in 1% acetic acid in water. The preferred molecular weight according to the present invention results in a viscosity ranging from 10 to 300 mPa·s, especially from 20 to 200 mPa·s, more particularly from 50 mPa·s to 100 mPa·s. When using chitosan with a molecular weight resulting in a viscosity of a 1% solution in 1% acetic acid in water lower than 10 mPa·s the absorption enhancing effect of chitosan is considered to be strongly reduced. When using chitosan with a molecular weight resulting in a viscosity of a 1% solution in 1% acetic acid in water higher than 300 mPa·s the resulting final composition may be too viscous to conveniently administer.

In a further preferred embodiment of the invention said chitosan is unmodified.

In an alternative embodiment of the invention said chitosan is modified.

In a further embodiment of the invention said modified chitosan is a quaternary chitosan or thiolated chitosan.

The term "chitosan" is used in this application to encompass chitosan in unmodified, modified and salt forms such as for example chitosan glutamate.

The pH range in which chitosan or its salts is soluble depends upon the deacetylation grade of the chitosan. The lower the deacetylation of the chitosan the higher the pH can be at which the chitosan remains soluble.

The pH of the composition according to the present invention may range from 3.0 to 9.0. The pH of the composition comprising the preferred form of chitosan may range from 3.0 to 8.0 or from 3.0 to 7.0. Preferably the pH range of the composition is from 4.0 to 6.0. The preferred range of pH is between 4.0 and 5.5.

In a preferred embodiment said composition comprises chitosan at a concentration of between 0.10-5.00% (w/v), more suitably between 0.25-1.00% (w/v) or 0.40-0.75% (w/v).

Suitably, said composition comprises chitosan at a concentration of between 0.45 and 0.55% (w/v).

Suitably said composition comprises chitosan at a concentration of 0.5% (w/v).

Suitably said composition comprises tetracosactide (glutamate) at a concentration of between 0.01 to 1% (w/v).

Suitably said composition comprises tetracosactide (glutamate) at a concentration of 0.15 to 0.4% (w/v).

Suitably said composition comprises tetracosactide (glutamate) at a concentration of 0.25% (w/v)

In a preferred embodiment of the invention said composition further comprises tonicity adjusting agents, preservatives and acids and buffers to adjust and/or maintain pH.

In a preferred embodiment of the invention said tonicity adjusting agents are selected from the group consisting of sodium chloride, glucose, dextrose, mannitol, sorbitol or lactose.

In a further preferred embodiment of the invention said tonicity adjusting agents is sodium chloride.

The tonicity of the composition should approximately be equal to the tonicity of plasma.

In a preferred embodiment of the invention said composition comprises preservatives selected from the group of quaternary ammonium salts such as lauralkonium chloride, benzalkonium chloride, benzododecinium chloride, cetyl pyridium chloride, cetrimide, domiphen bromide; alcohols such as benzyl alcohol, chlorobutanol, o-cresol, phenyl ethyl alcohol; organic acids or salts thereof such as benzoic acid, sodium benzoate, potassium sorbate, parabens; or complex forming agents such as EDTA.

In a preferred embodiment of the invention said preservative is benzalkonium chloride.

In a further preferred embodiment of the invention said buffer comprises sodium acetate.

In a further preferred embodiment of the invention said acid is selected from the group consisting of hydrochloric acid, lactic acid, glutamic acid, maleic acid, acetic acid, formic acid, propionic acid, malic acid, malonic acid, adipic acid, succinic acid or nitric acid In a further preferred embodiment of the invention said acid is acetic acid.

In a preferred embodiment of the invention said composition comprises of the following components:

tetracosactide acetate 0.25% (w/v)
chitosan glutamate 0.5% (w/v)
sodium chloride 0.54% (w/v)
benzalkonium chloride 0.015% (w/v)
acetic acid 0.51% (w/v) and
sodium acetate trihydrate 0.21% (w/v).

In a preferred embodiment of the invention said composition comprises between 0.5-5 mg/ml tetracosactide acetate.

In a preferred embodiment said composition is administered at an effective dose of between 25-1000 μg tetracosactide acetate.

In a preferred embodiment said composition is administered at a dose between 100-500 μg tetracosactide acetate.

In a preferred embodiment said composition is administered at an effective dose selected form the group consisting of 25, 50, 75, 100, 125, 150, 175, 200, 225, 250, 275, 300, 325, 350, 375, 400, 425, 450, 475, 500, 550, 600, 650, 700, 750, 800, 850, 900, 950, 1000 μg tetracosactide acetate.

In a preferred embodiment said composition is administered at an effective dose of 500 µg tetracosactide acetate.

In a preferred embodiment of the invention said effective dose is administered once in 24 h.

The intranasal composition according to the invention can form an aerosol or is applied to the nasal cavity as a liquid. The property to form an aerosol mainly depends upon the viscosity of the composition. When the composition is too viscous, the composition will not allow the formation of a spray. It can be sprayed and still the droplets reside long enough in the nasal cavity to allow for a good bioavailability. The viscosity of the solution may range between 10-300 mPa. The compositions preferably adhere to the mucosa, at least to some extent, and this facilitates retention of the composition of the mucosa and/or enhances the absorption of the active ingredient.

According to a further aspect of the invention there is provided a composition according to the invention for use in the diagnosis of adrenal insufficiency in a subject In a preferred embodiment of the invention said adrenal insufficiency is caused by a condition selected from the group consisting of: primary or secondary or tertiary adrenal failure examples of which include congenital adrenal hyperplasia, late-onset congenital adrenal hyperplasia, glucocorticoid-remediable aldosteronism (GRA), Addison's disease or tuberculosis.

In a preferred embodiment of the invention said subject is a paediatric subject.

A paediatric subject includes neonates (0-28 days old), infants (1-12 months old), young children (12 months-6 years old), prepubescent [7-14 years old] or adolescents [15-18].

According to an aspect of the invention there is provided a diagnostic test for adrenal insufficiency in a subject comprising the following steps:

i) obtaining a sample of saliva from a subject and measuring cortisol or/and cortisone concentration in said saliva sample;

ii) repeating step i) after intranasal administration of the composition according to the invention and iii) comparing the concentration of cortisol or cortisone in the saliva sample of step (i) with the cortisol or cortisone concentration of step (ii); and iv) determining if the subject has adrenal insufficiency.

In a preferred method of the invention said subject is a human.

In a preferred method of the invention said subject is a paediatric subject.

In a further preferred method of the invention said paediatric subject is selected from the group consisting of neonates, infants, children or adolescents.

In a preferred method of the invention step i) is repeated 5, 10, 15, 20, 30, 40, 45, 50, 60, 75, 90, 120, 150 and/or 180 min after intranasal administration of said composition according to the invention.

In a preferred method of the invention step i) is repeated 2, 3, 4 or 5 times after intranasal administration of said composition according to the invention.

In a further preferred method of the invention step i) is repeated at frequent intervals such as 2, 5, 10, 15, 20 or 30-minute intervals after intranasal administration of said composition according to the invention. Step i) can also be repeated at 2, 5, 10, 15, 20 or 30-minute intervals after intranasal administration of said composition according to the invention which are non-linear e.g. the second sample is taken after 30 min, the third sample taken after 45 minutes and the forth sample taken after 60 min from the time point when the first sample is taken.

In an alternative further preferred method of the invention step i) is repeated at frequent intervals such as 30, 45, 60, 90, 120, 150 or 180-minute intervals after intranasal administration of said composition according to the invention.

According to a further aspect of the invention there is provided a device comprising the pharmaceutical composition according to the invention wherein said device is adapted to deliver said composition as an aerosol or in liquid form.

In a preferred embodiment said composition is delivered into the nasal cavity.

In a preferred embodiment of the invention said device is selected from the group consisting of pipettes, syringes, nasal spray pumps, dropper bottles, squeeze bottles, metered-dose spray pumps, single-dose spray devices, nasal pressurized metered-dose inhalers, mucosal atomiser devices or nebulisers.

According to an aspect of the invention there is provided a kit comprising a container for collecting saliva, a composition according to the invention comprising ACTH or an ACTH synthetic analogue.

Definitions

"$AUC_{(0-t)}$" is the area under the concentration time curve from time zero until the last quantifiable time point i.e. 180 minutes.

"$AUC_{(0-\infty)}$" area under the concentration time curve from time zero until infinity.

Figure 4:
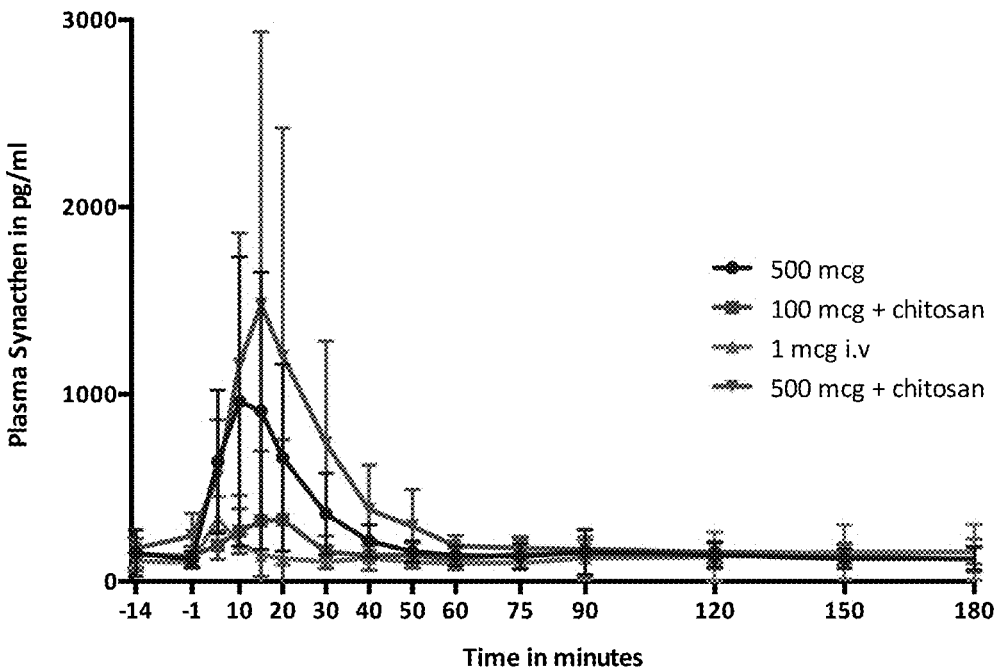

"Bioavailability (F)" is concerned with both the amount of drug present in the systemic circulation and the rate of systemic absorption. Bioavailability is often measured by comparing administration via a non-intravenous route with the i.v route. Absolute bioavailability is dependent on the dose and the area under the concentration-time profiles (AUC) following administration via the route of interest and i.v route (FIG. 4.3). Two different formulations of the same drug may have the same bioavailability as measured by the AUC but one formulation may release drug more quickly compared to the other, resulting in a higher initial concentration (Cmax) at an earlier time (Tmax), therefore the formulations would not be bioequivalent. In this study proving bioequivalence is not necessary but enough of the intranasal dose must be absorbed and rapidly enough to produce an equivalent cortisol response to the 1 mcg i.v SST.

$$F = \frac{AUC_{ev}}{AUC_{iv}} \times \frac{DOSE_{iv}}{DOSE_{ev}}$$

"Absolute Bioavailability equation" where F=bioavailability, AUC=area under the curve (concentration-time), iv=iv route, and ev=non-intravenous route i.e nasal.

"Cmax" is the maximum plasma concentration achieved

"Tmax" is the time to maximum plasma concentration

"Pharmacodynamics (PD)"—the effect of the drug on the body

"Pharmacokinetics (PK)" the effect of the body on the drug

"Terminal t½" the time taken to halve the plasma concentration after achieving pseudo-equilibrium. If plasma absorption is not a limiting factor then terminal t½ essentially reflects plasma clearance and distribution. However, if plasma absorption is a limiting factor then terminal t½ is a marker of the rate and degree of absorption. Terminal t½ is an important parameter in multiple dosing regimes as it determines the extent of drug accumulation.

IN or i.n. is the abbreviation for intranasal

IV or i.v. is the abbreviation for intravenous

Throughout the description and claims of this specification, the words "comprise" and "contain" and variations of the words, for example "comprising" and "comprises", means "including but not limited to", and is not intended to (and does not) exclude other moieties, additives, components, integers or steps. "Consisting essentially" means having the essential integers but including integers which do not materially affect the function of the essential integers.

Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith.

Figure 5:
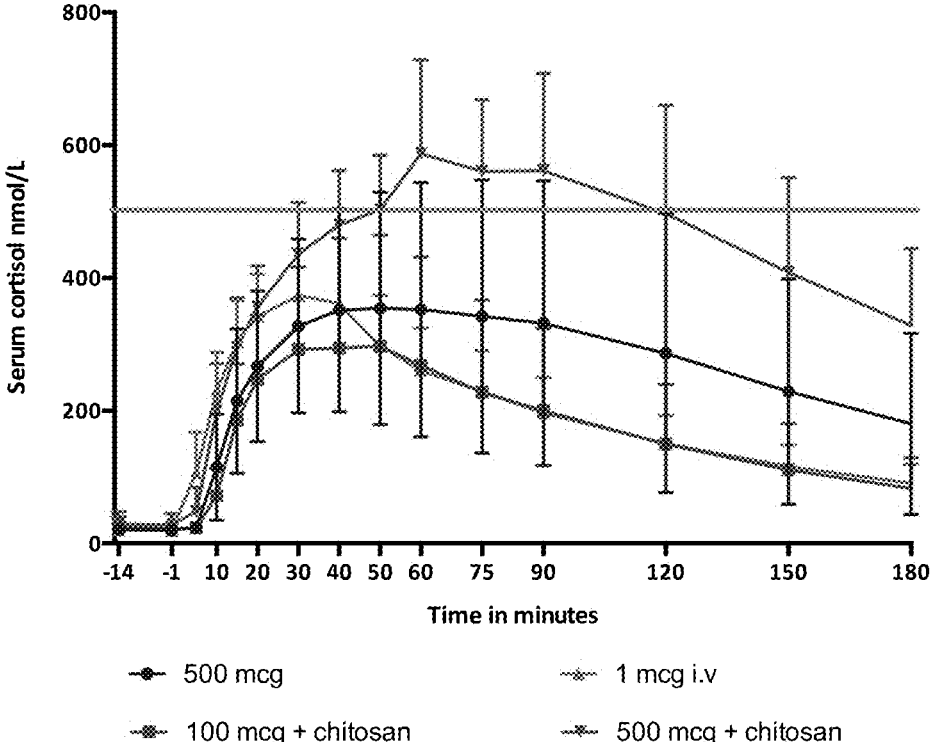
Figure 6:
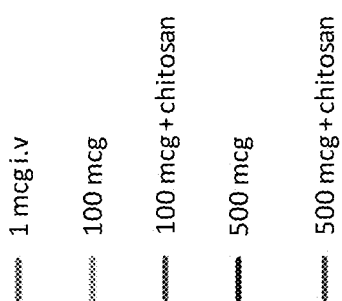
Figure 6:
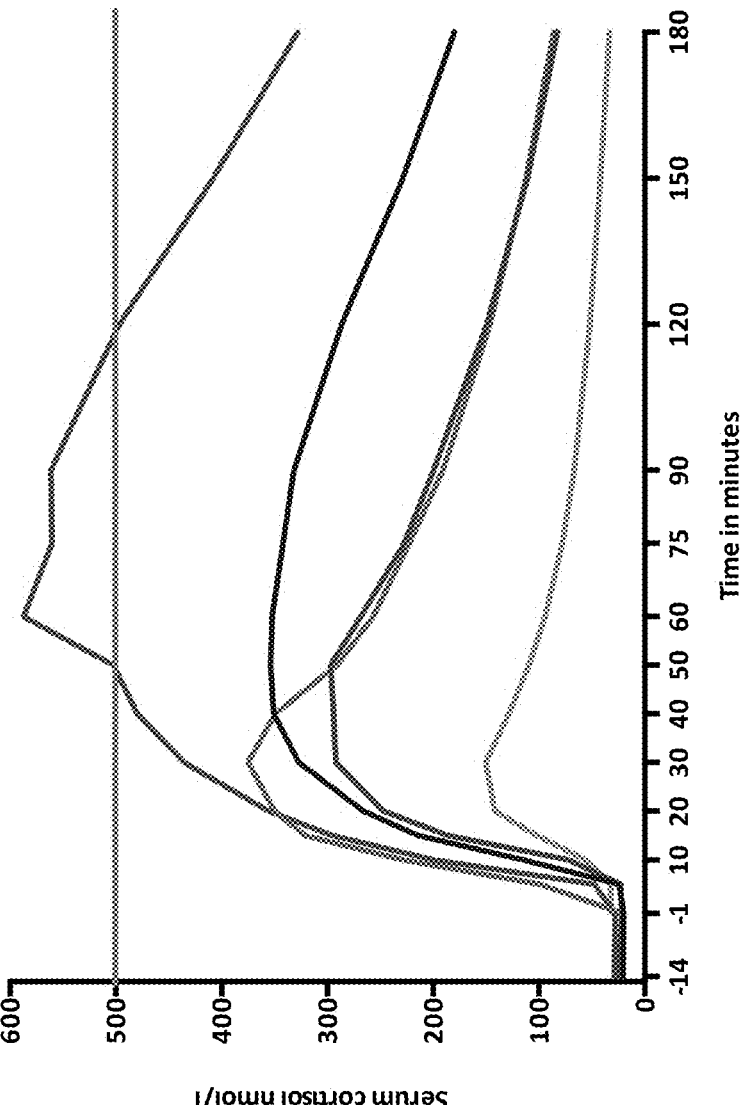
Figure 7:
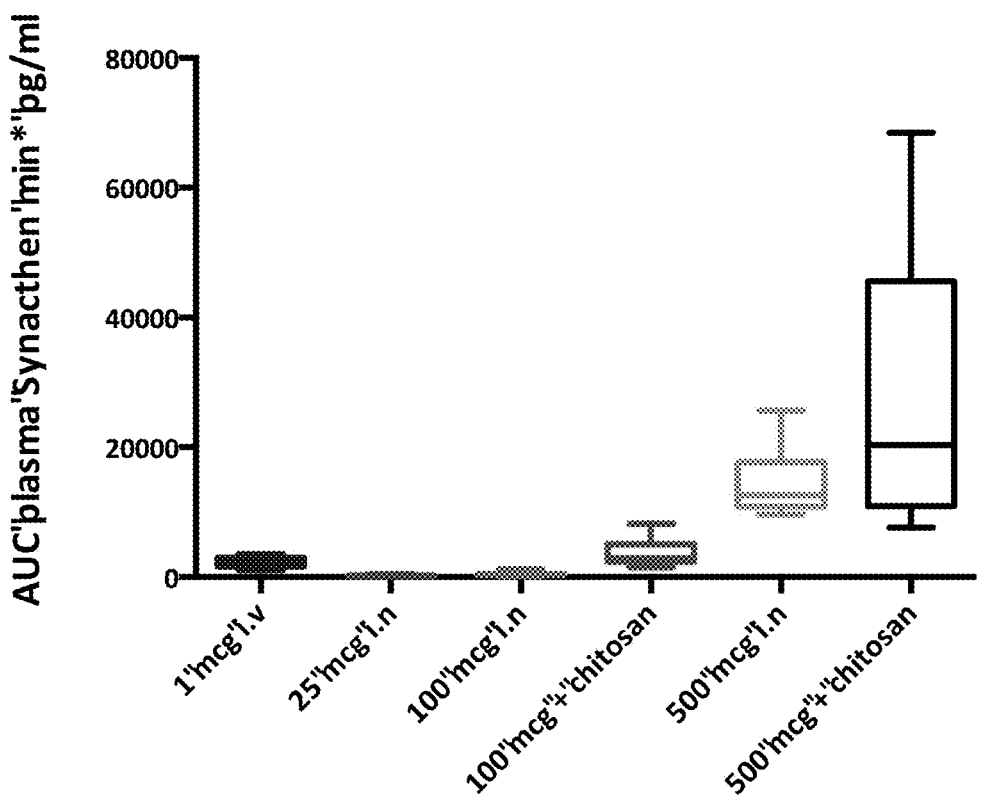
Figure 8A:
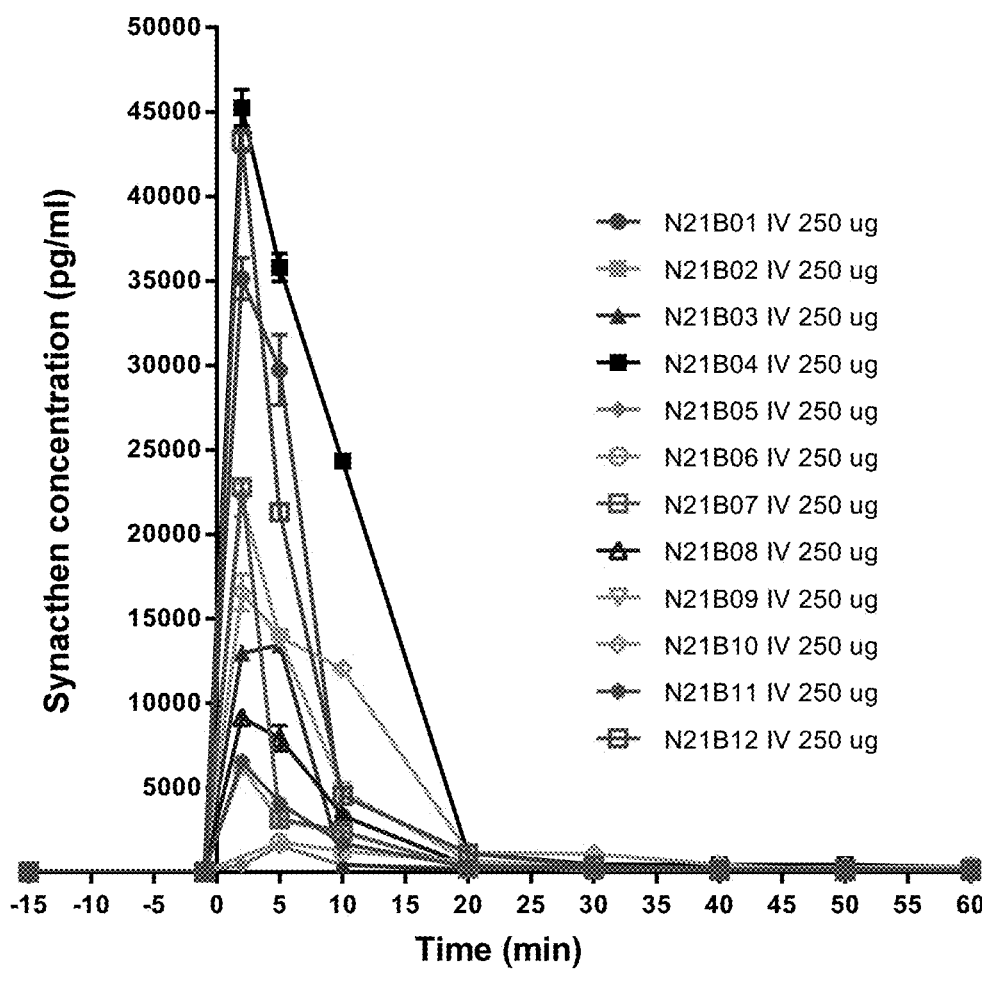
Figure 8B:
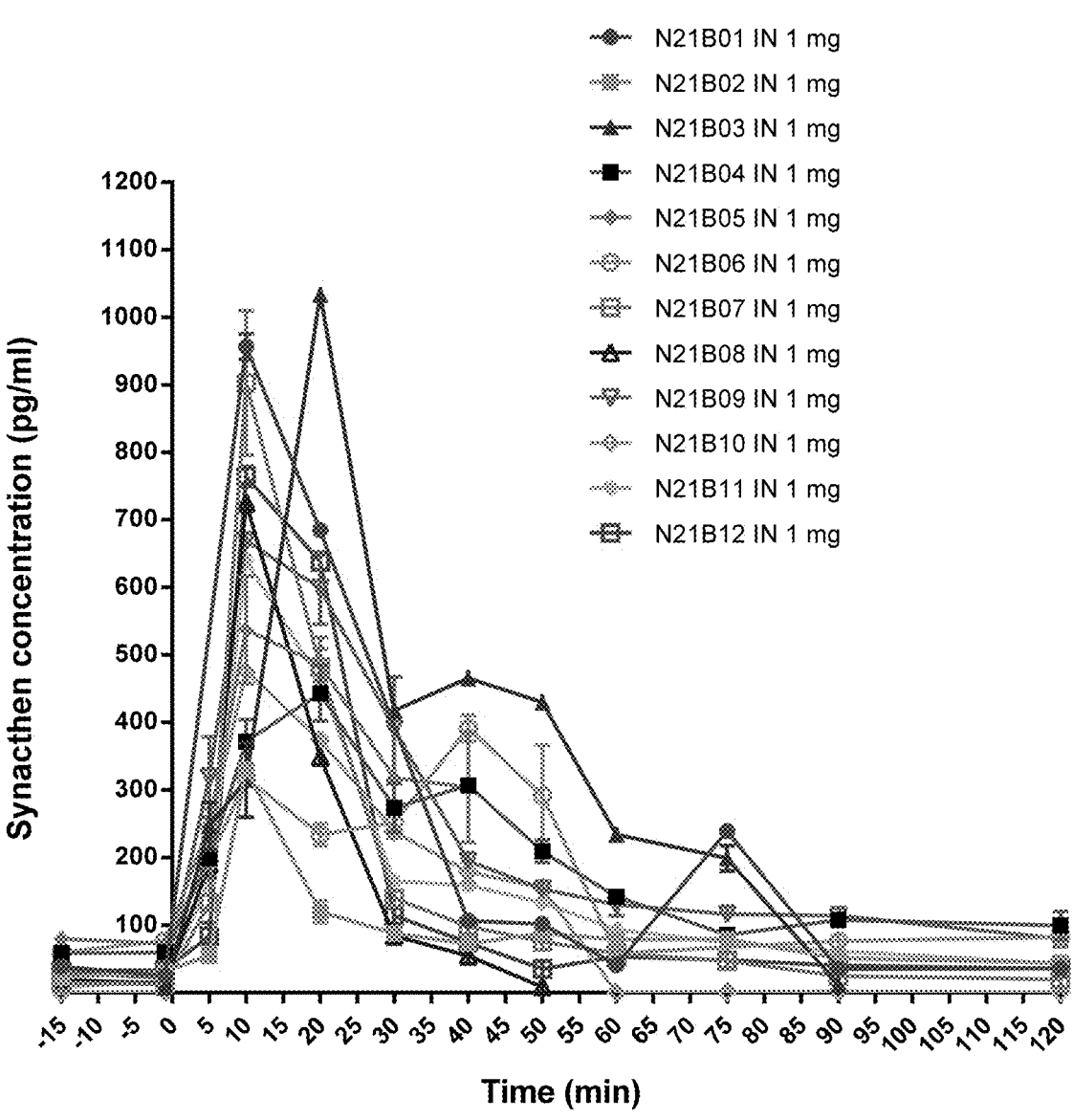
Figure 8C:
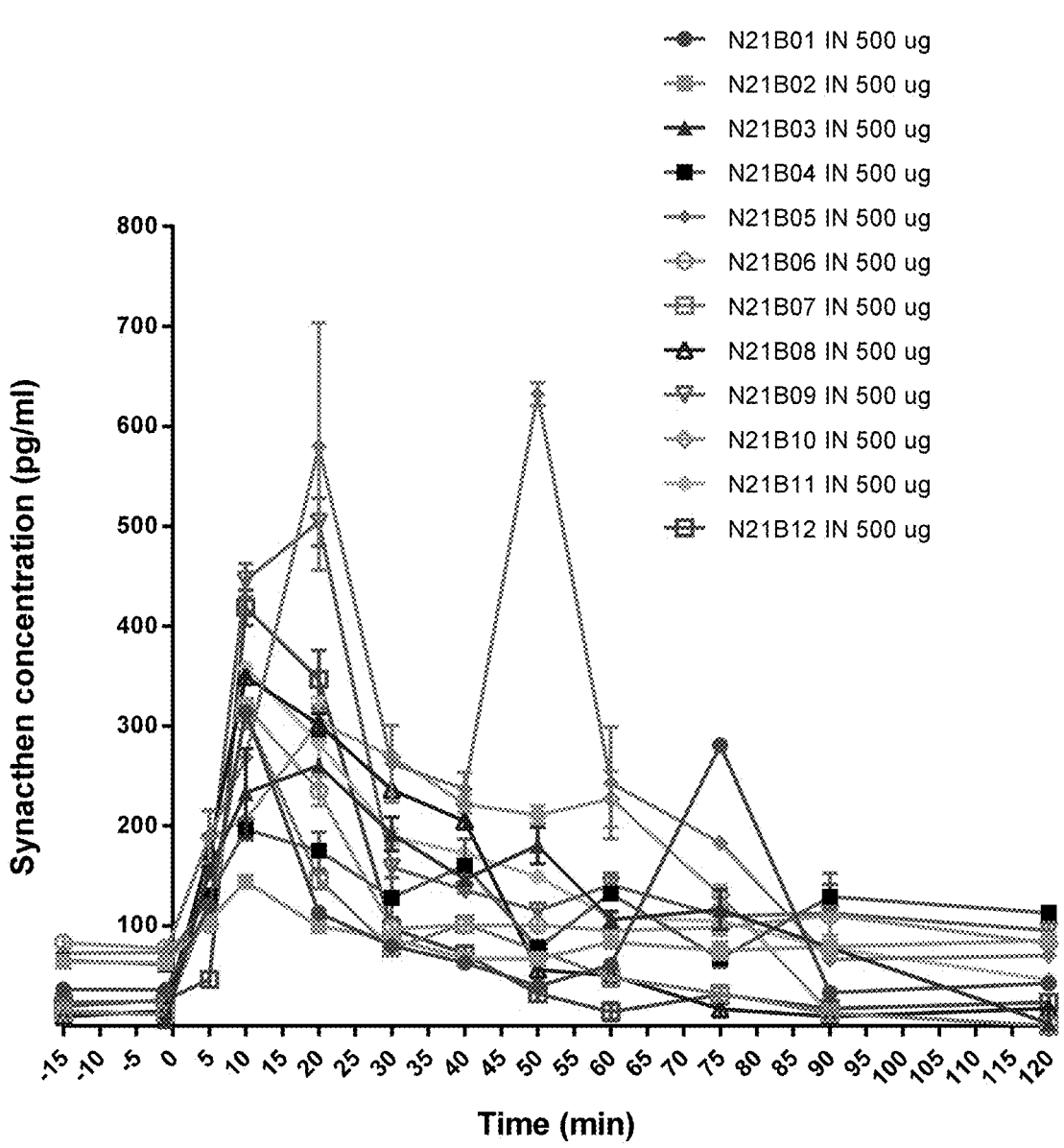
Figure 9:
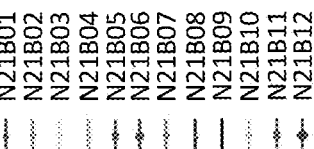
Figure 10:
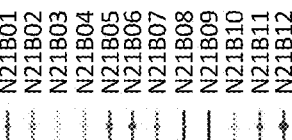
Figure 11:
Figure 12A:
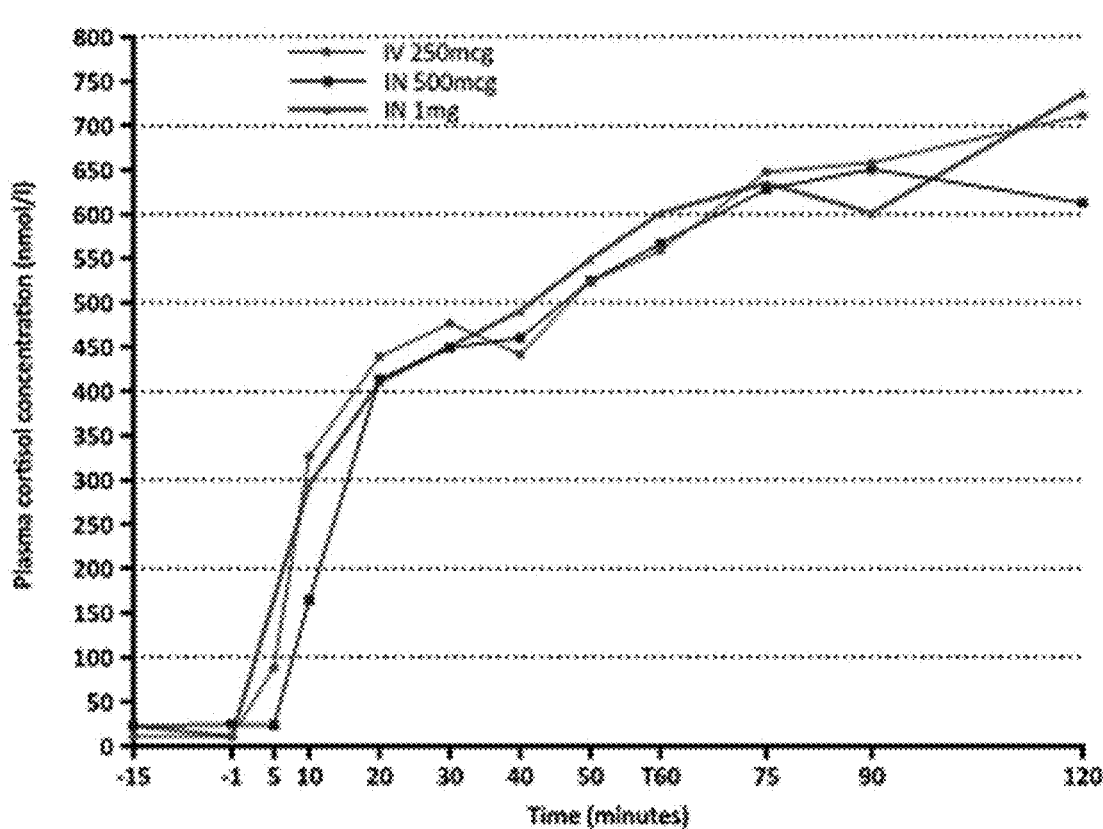
Figure 12B:
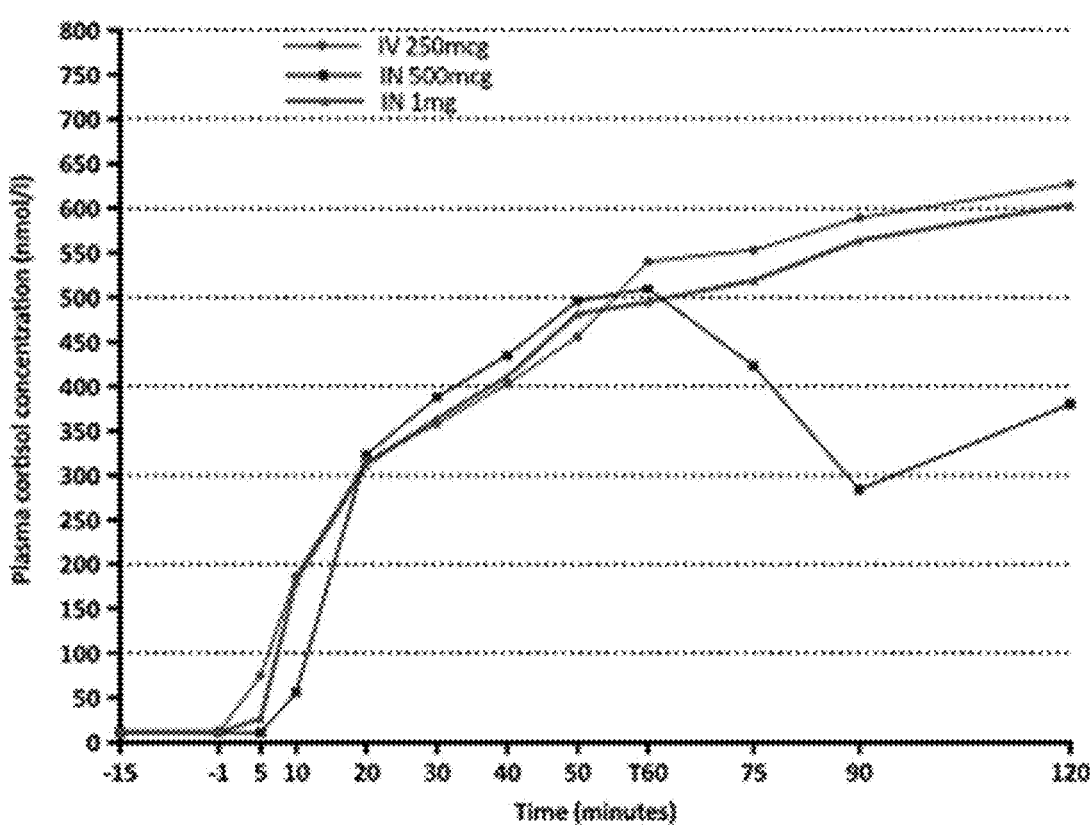
Figure 12C:
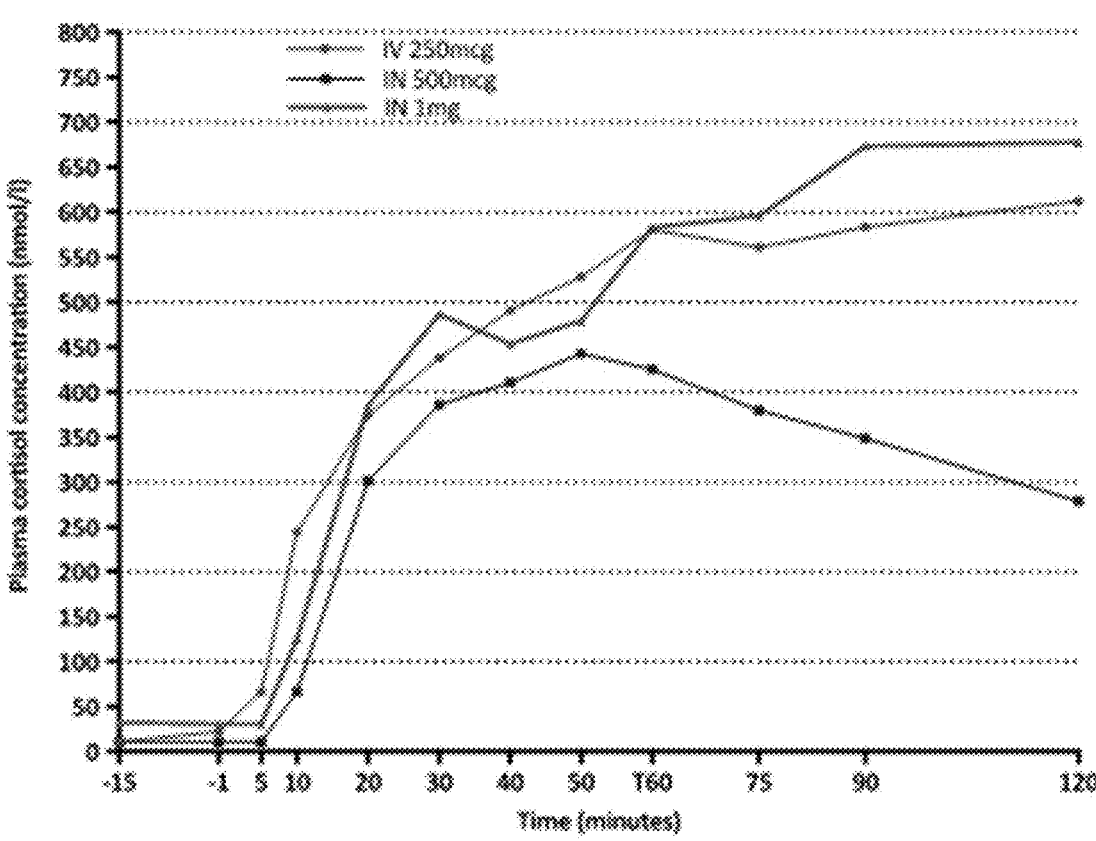
Figure 12D:
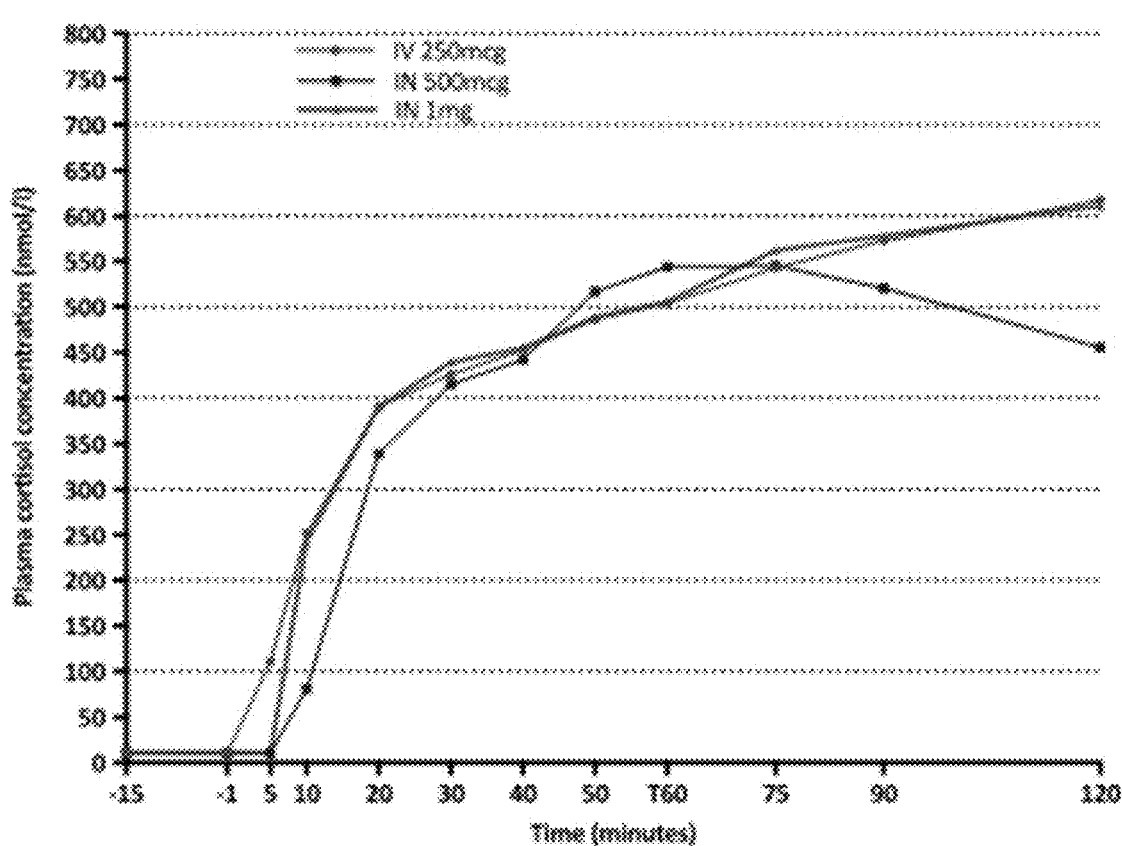
Figure 12E:
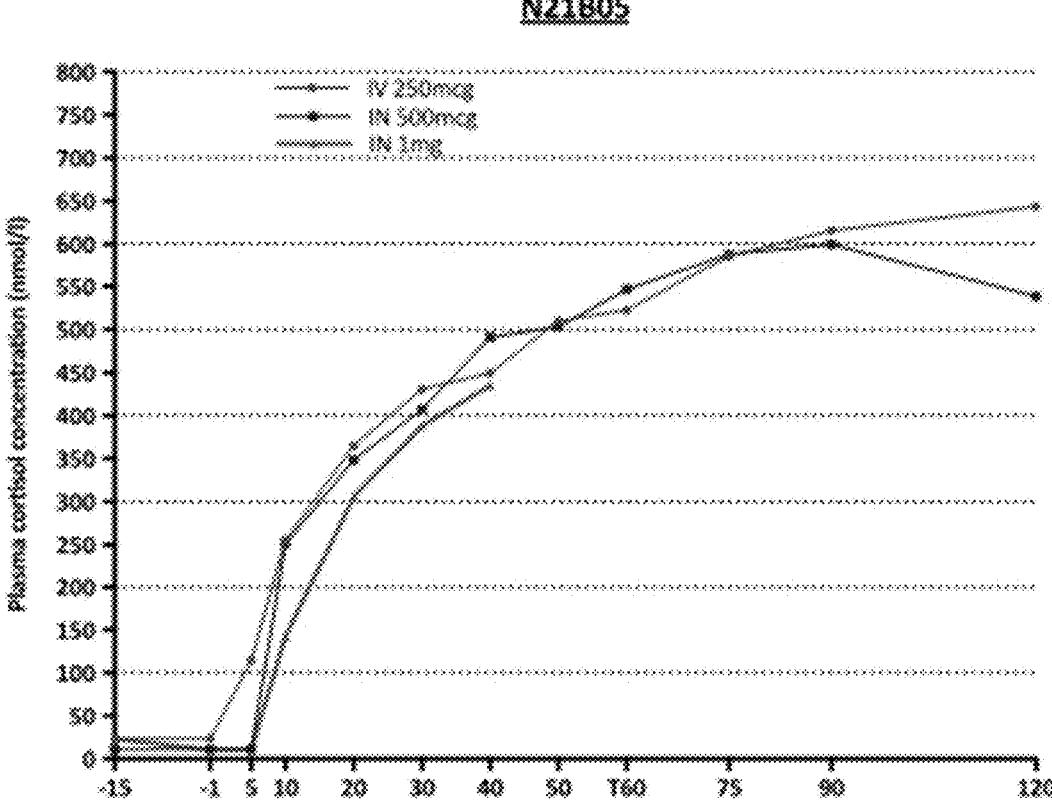
Figure 12F:
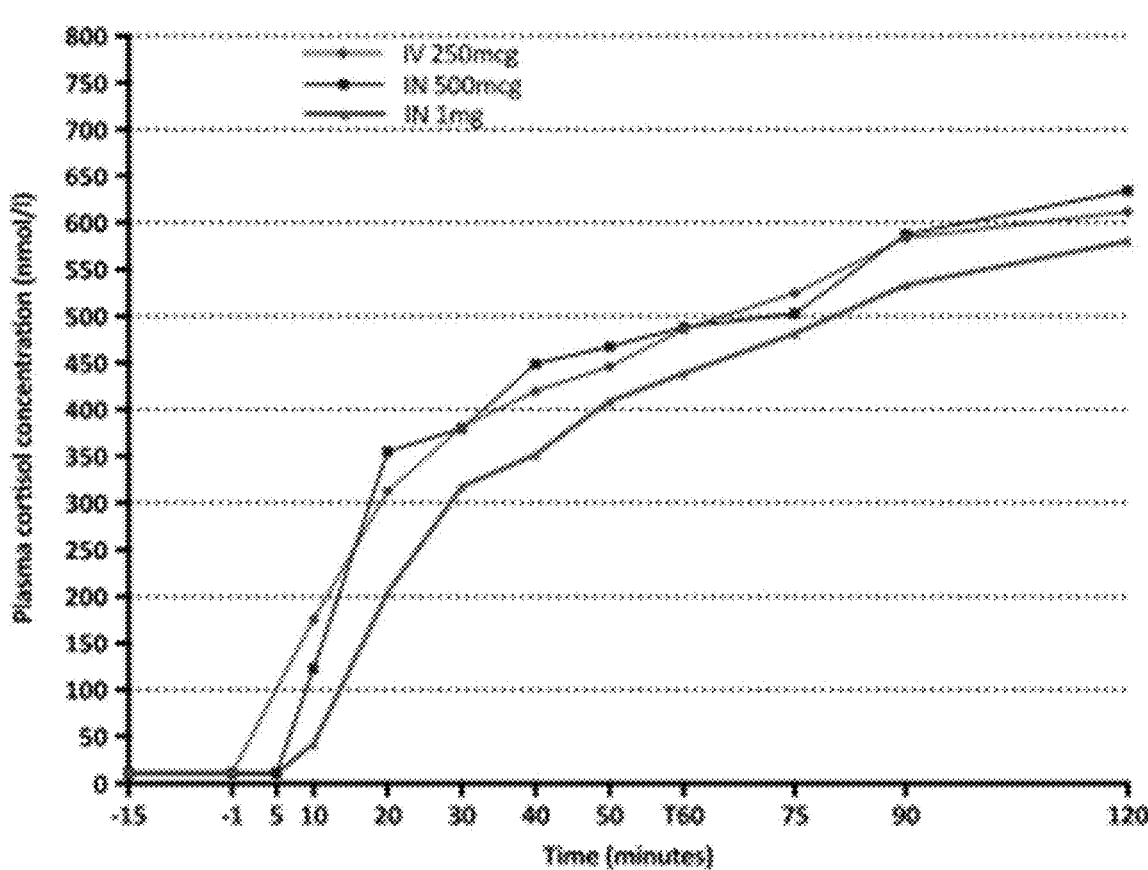
Figure 12G:
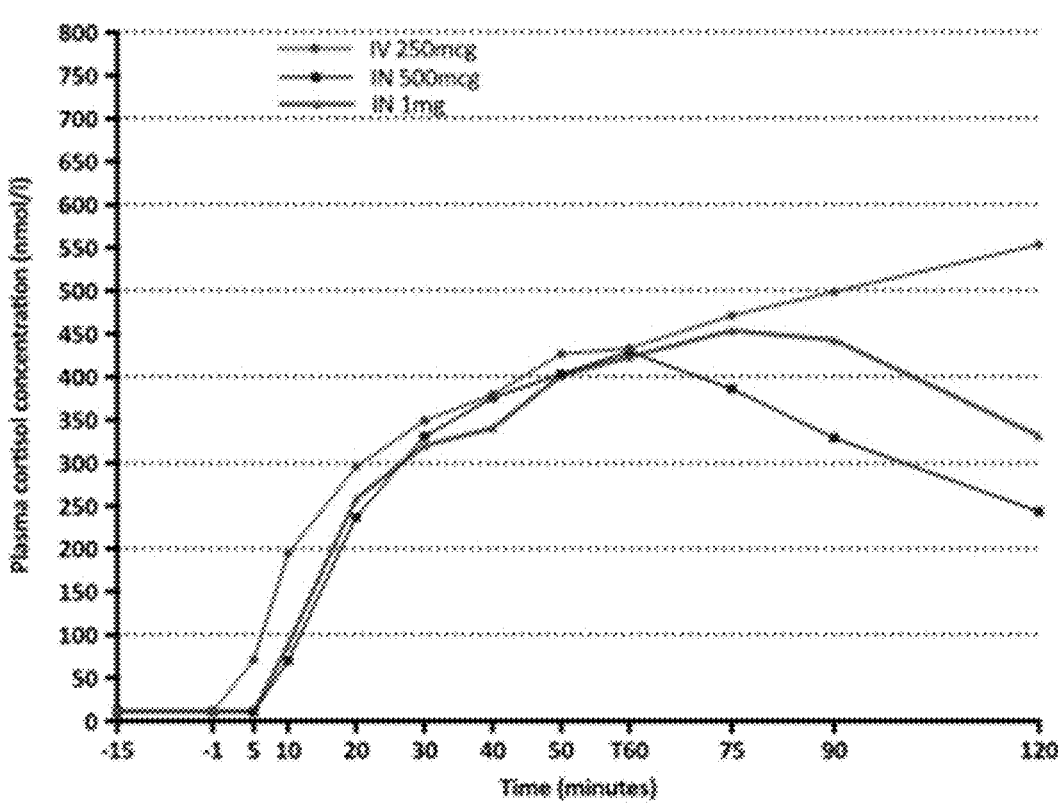
Figure 12H:
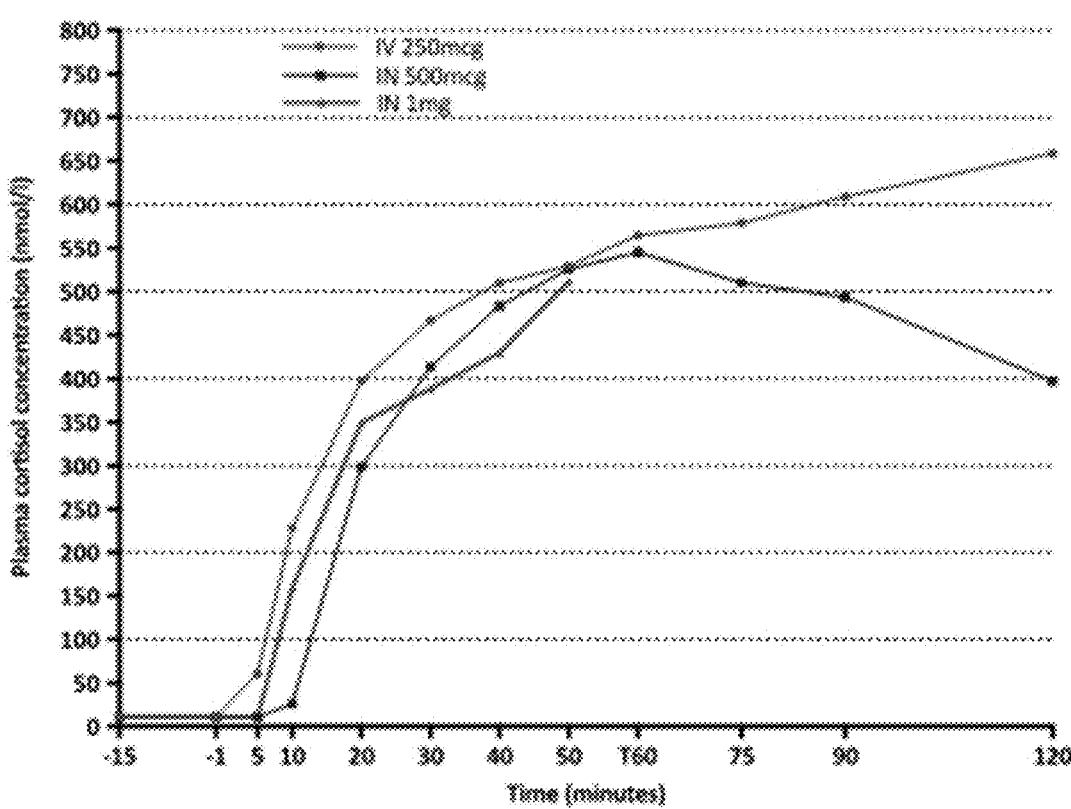
Figure 12I:
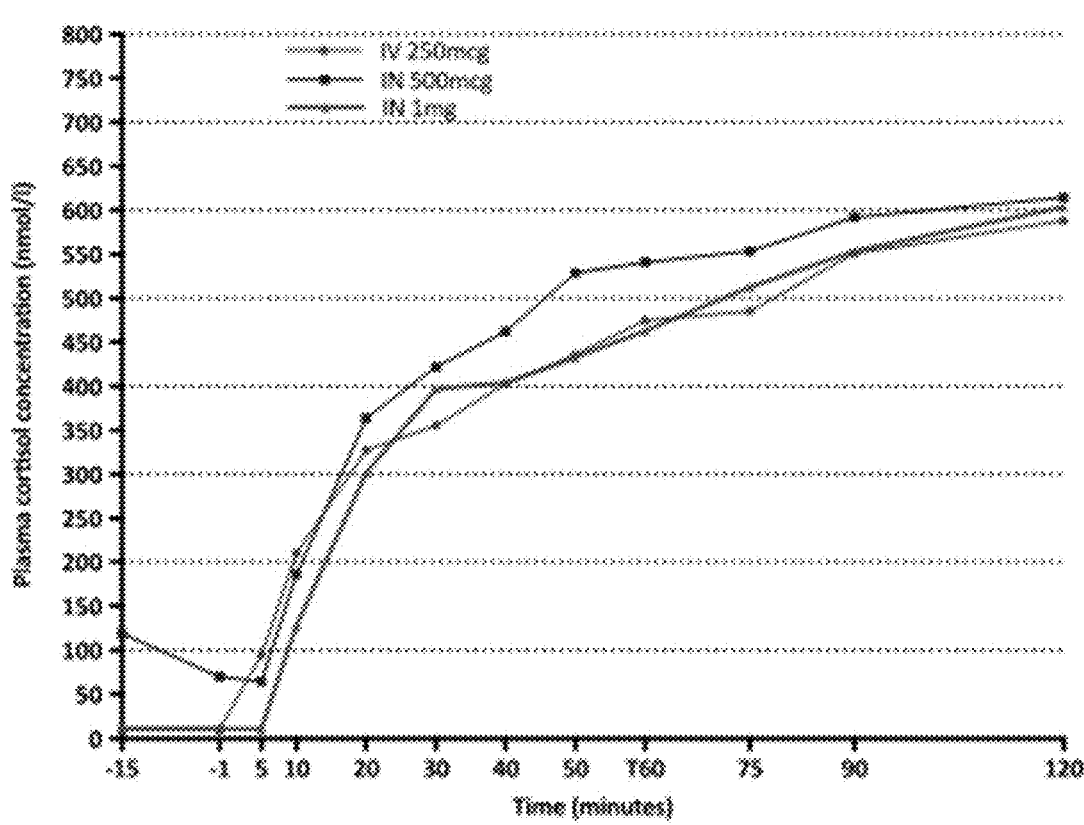
Figure 12J:
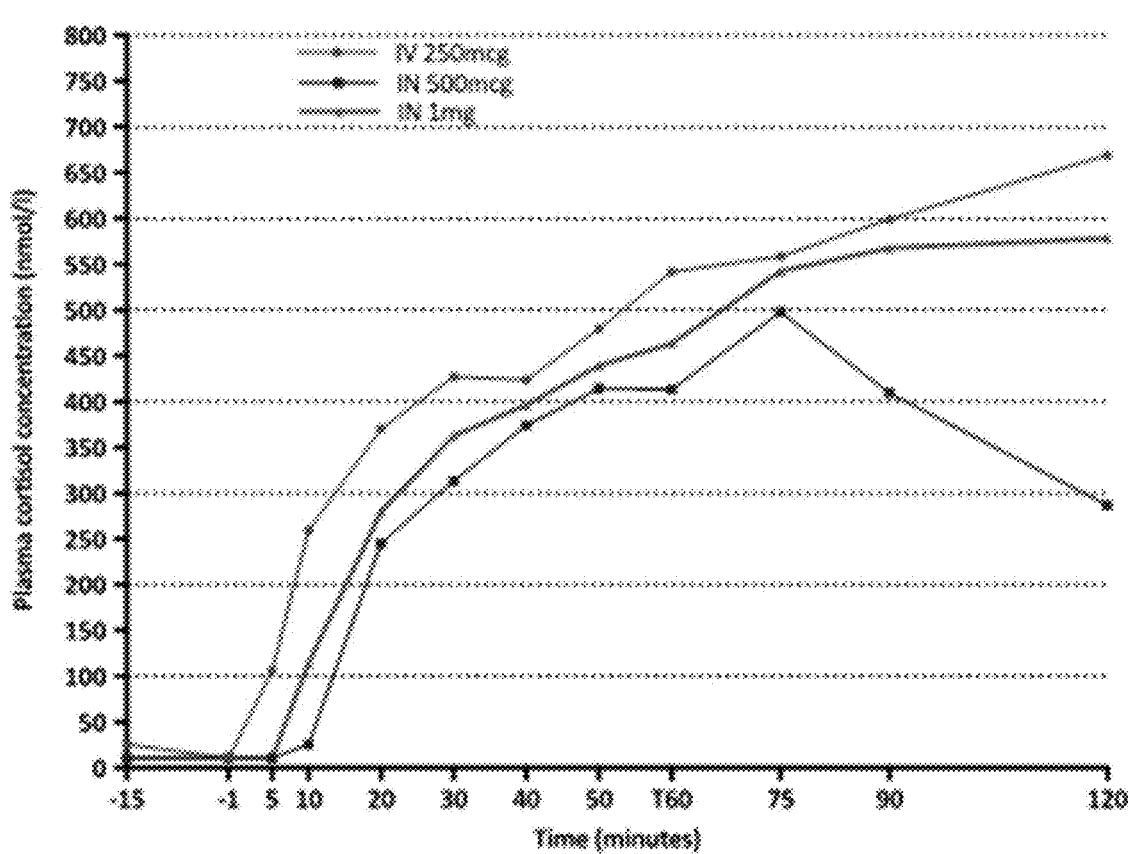
Figure 12K:
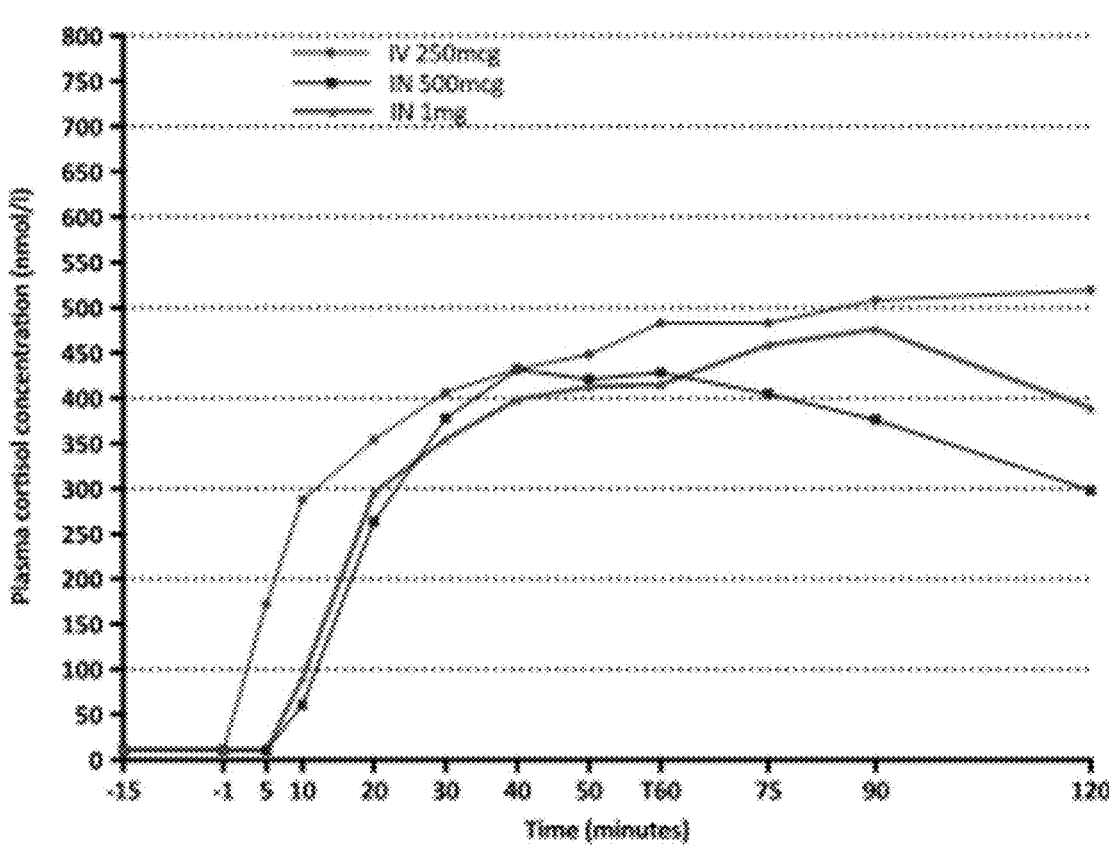
Figure 12L:
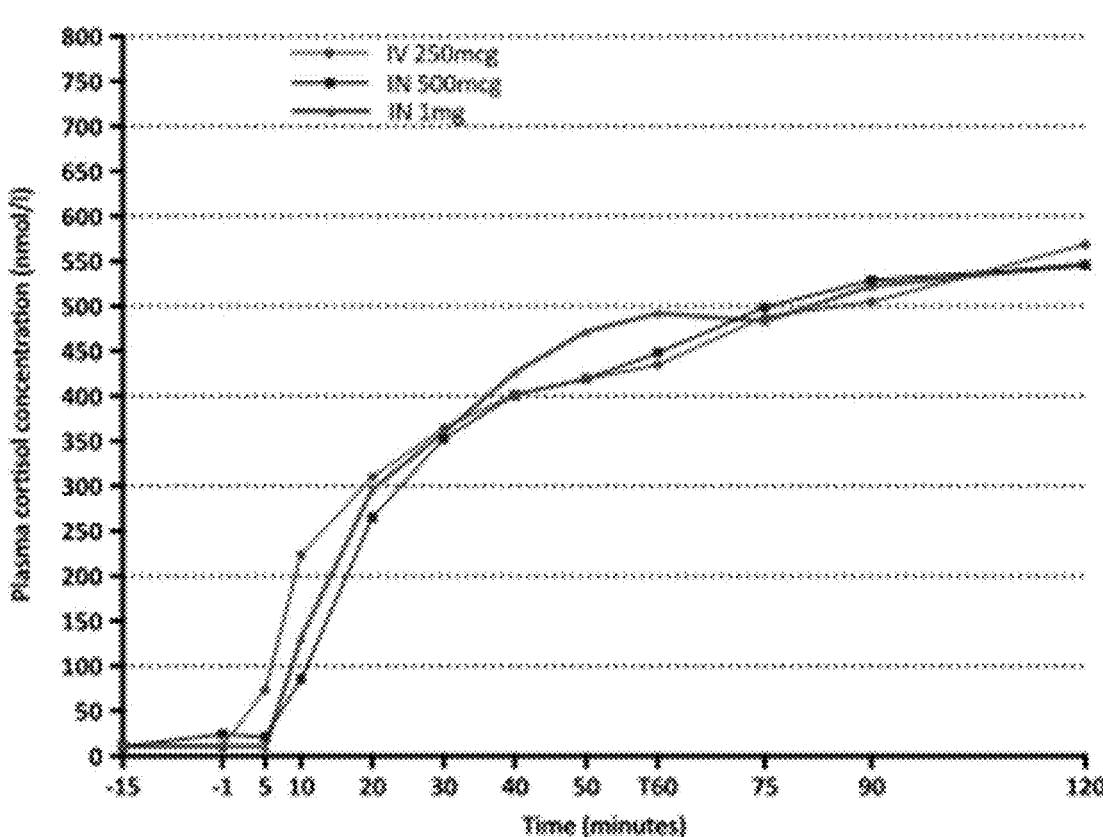
Figure 13:
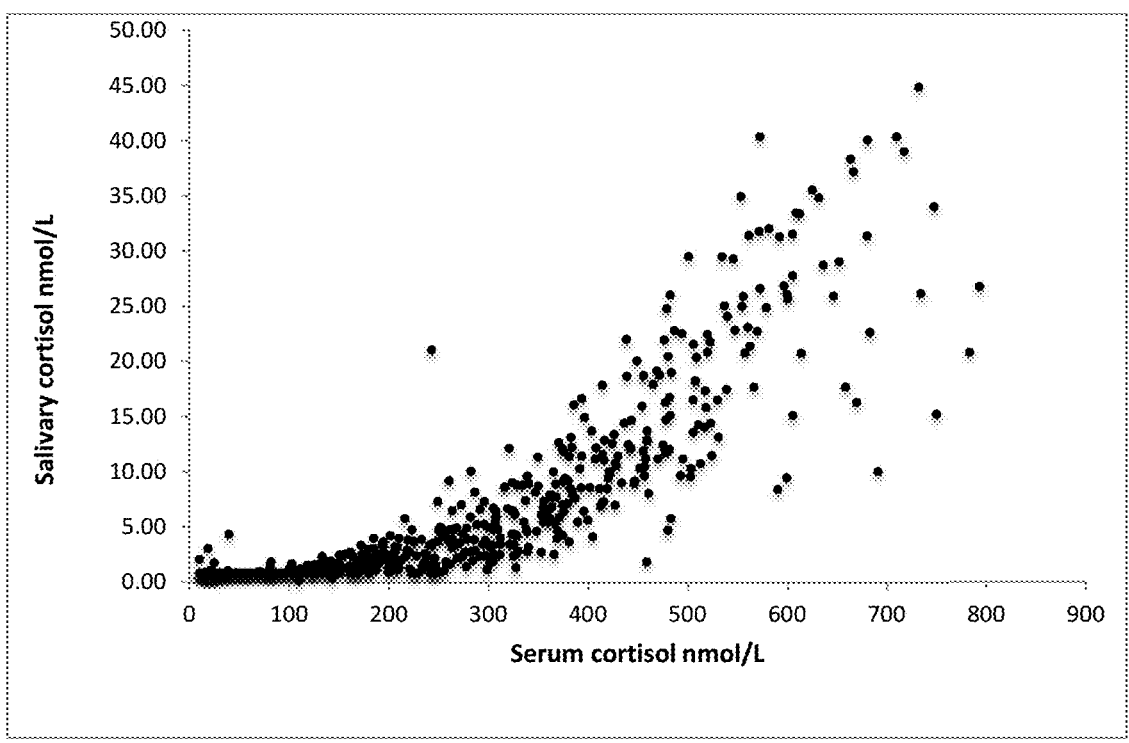
Figure 14:
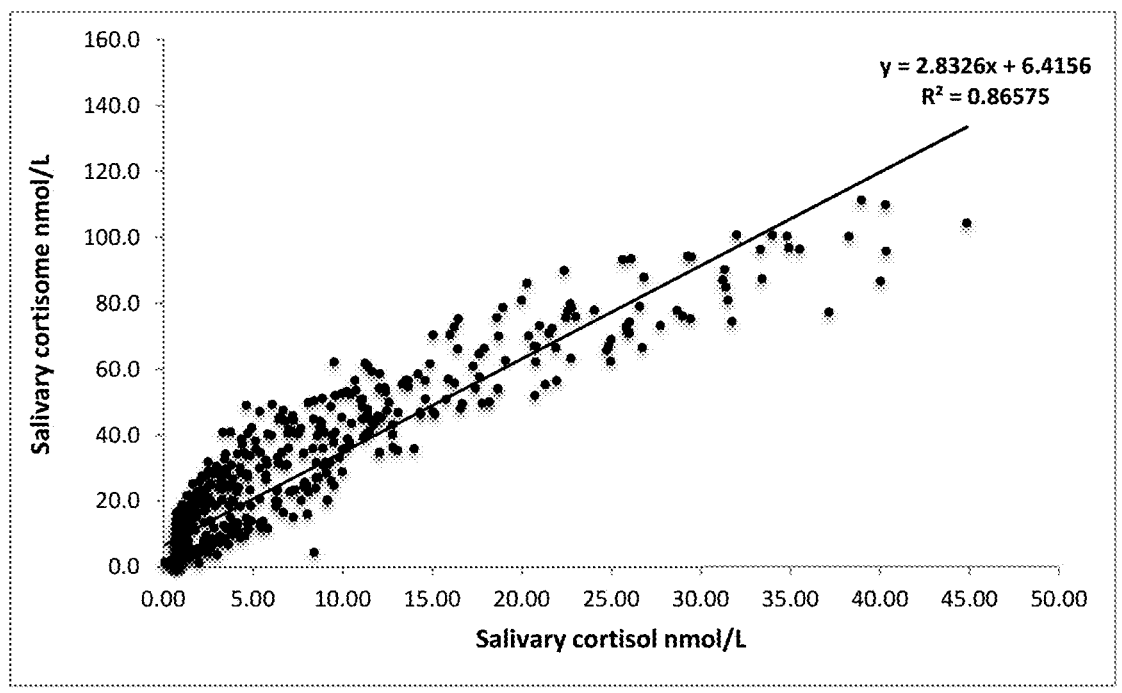
Figure 15:
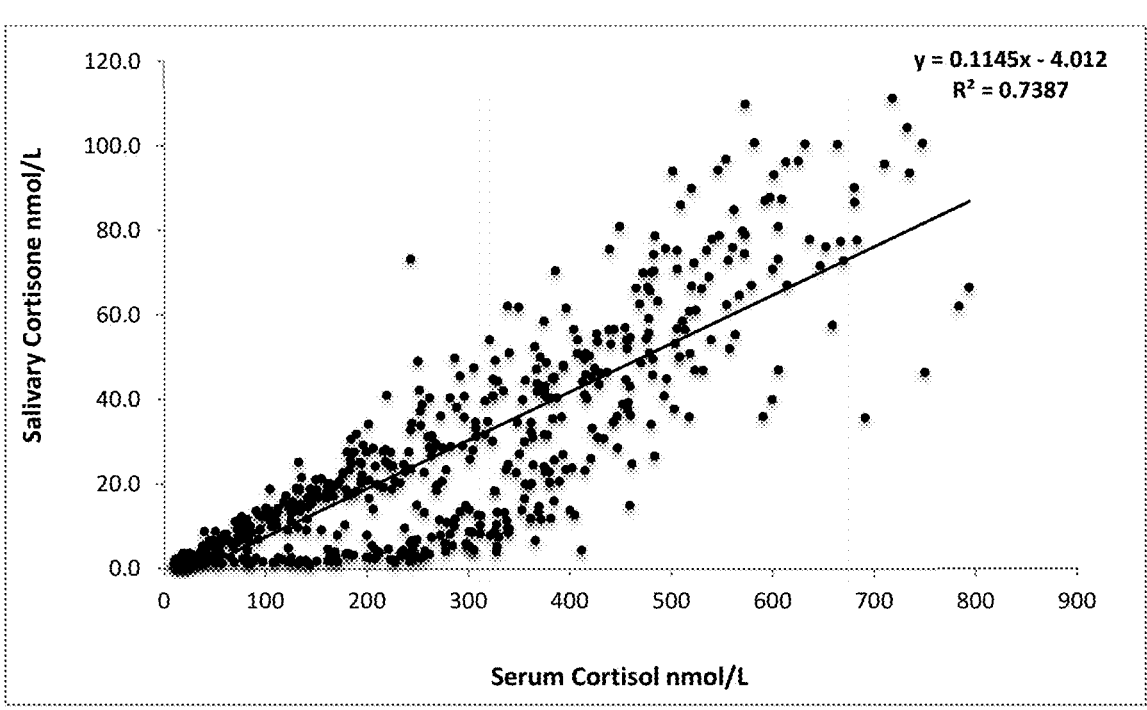
Figure 16:
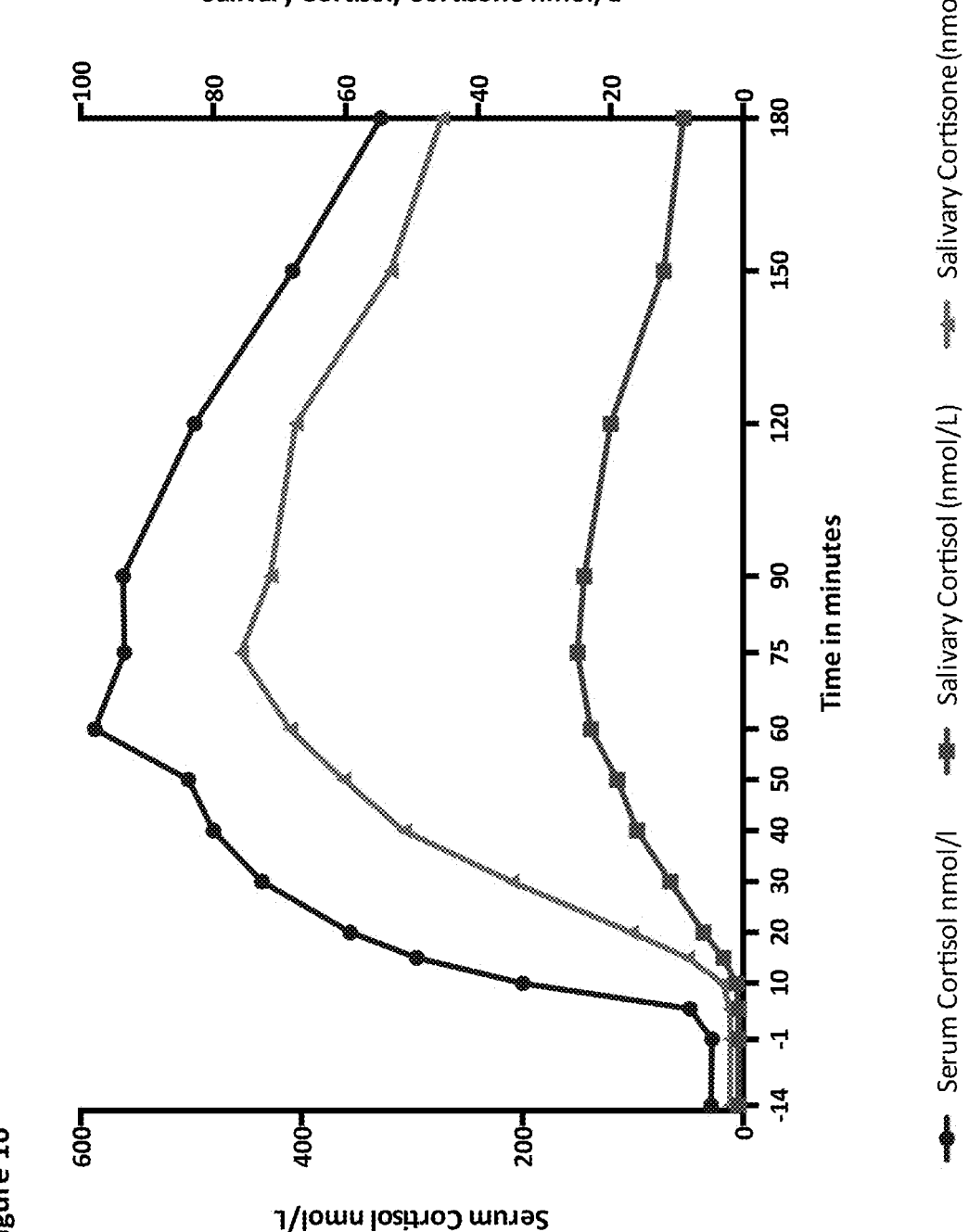
Figure 17:
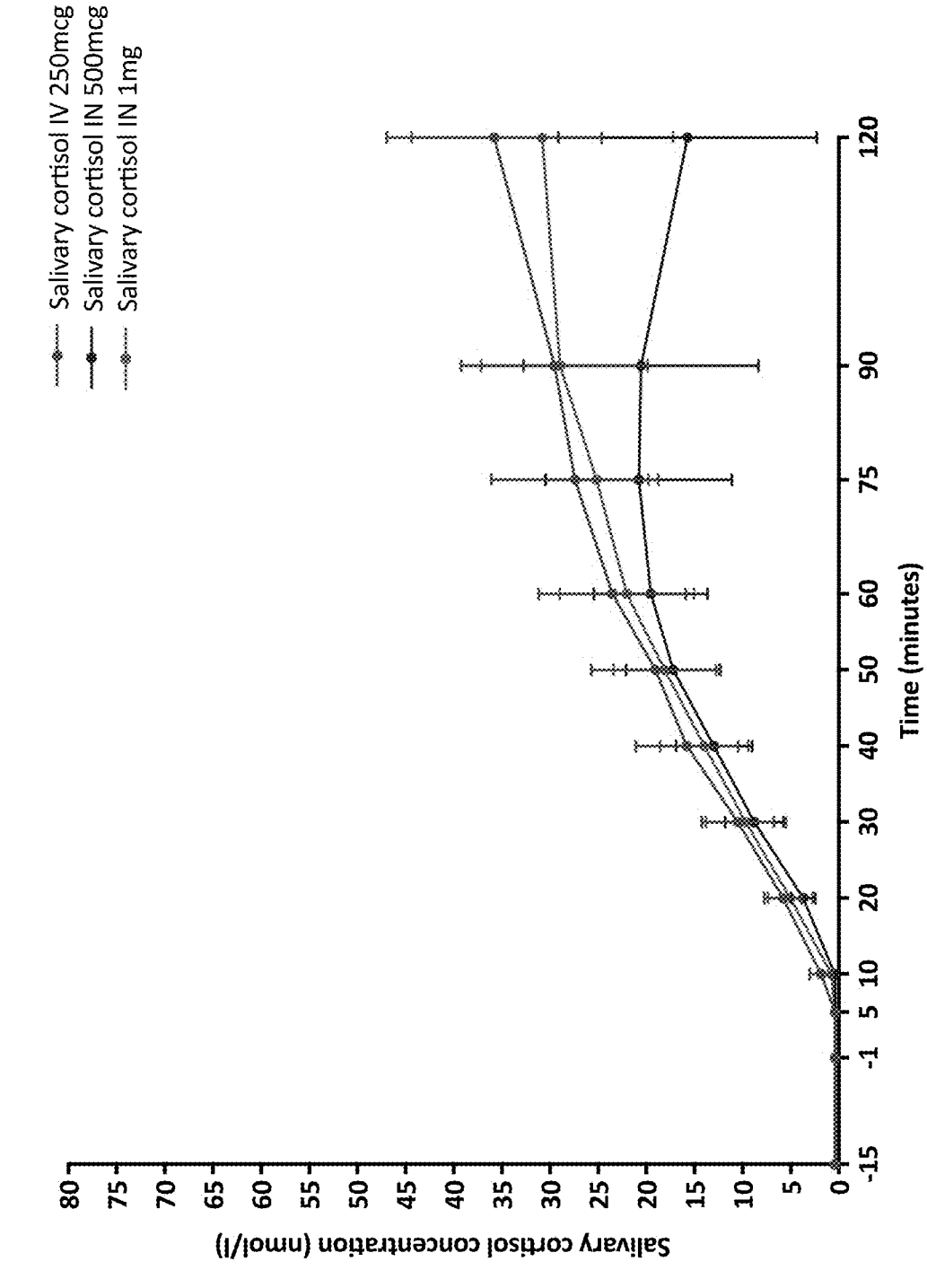
Figure 18:
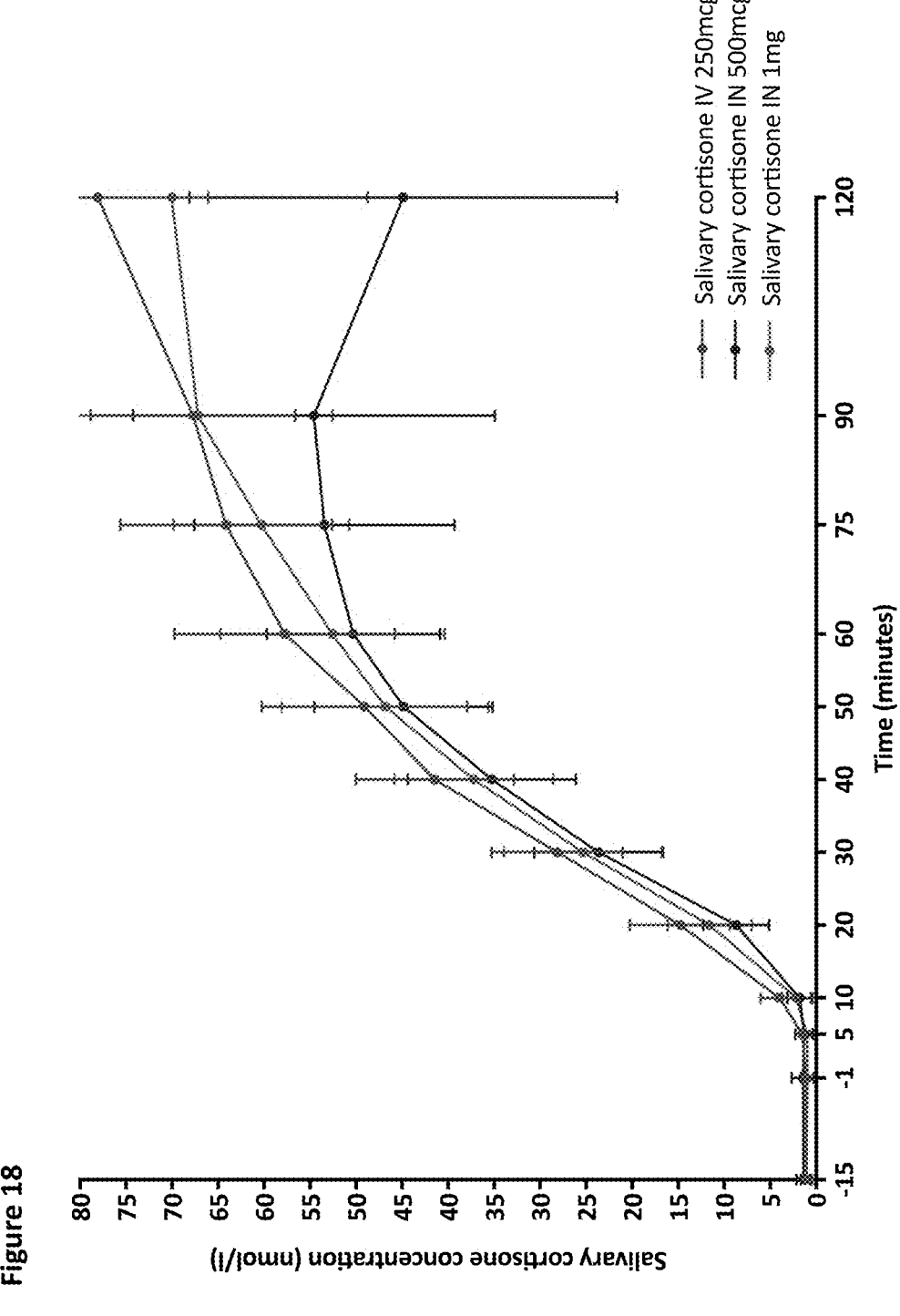
Figure 19:
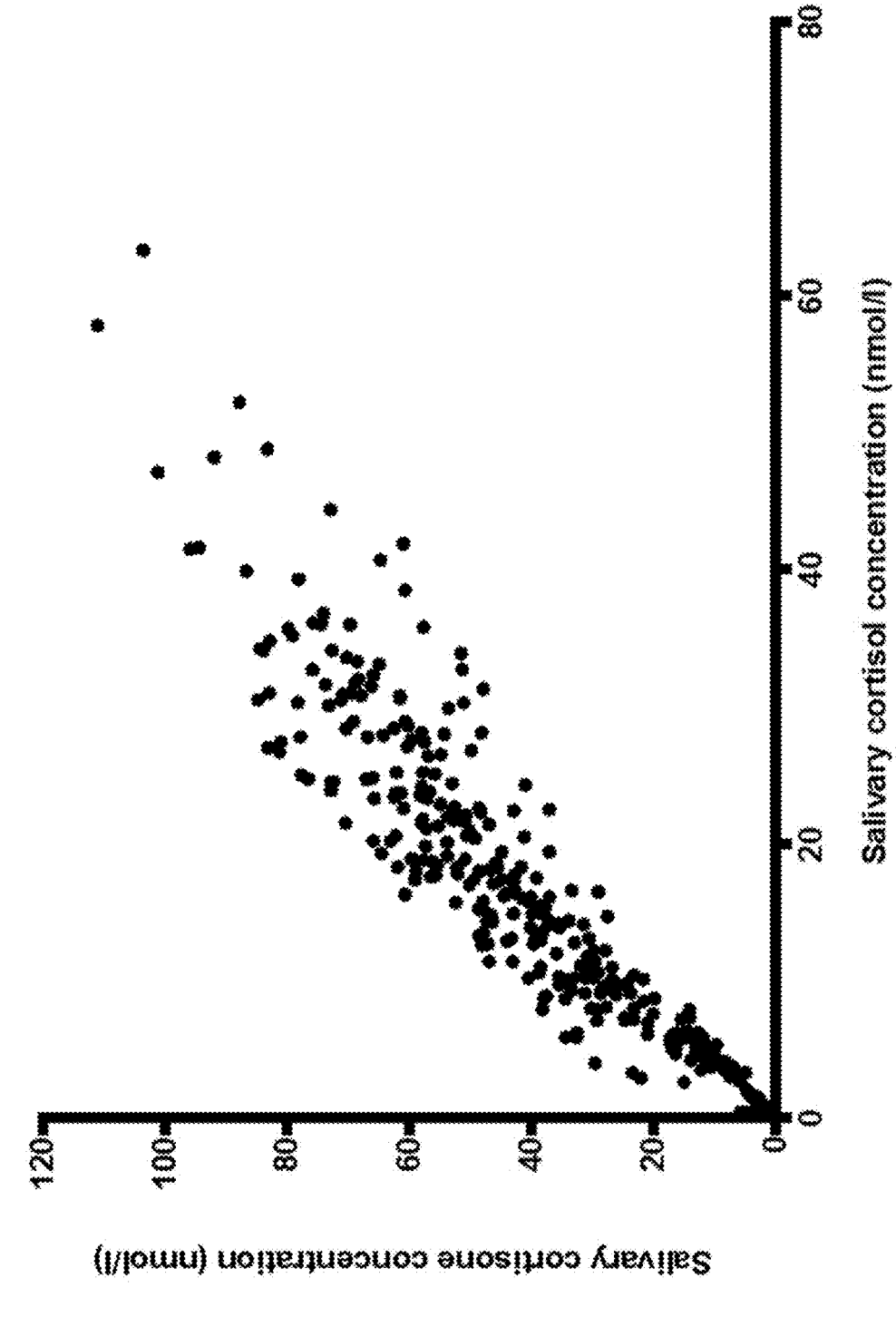
Figure 20:
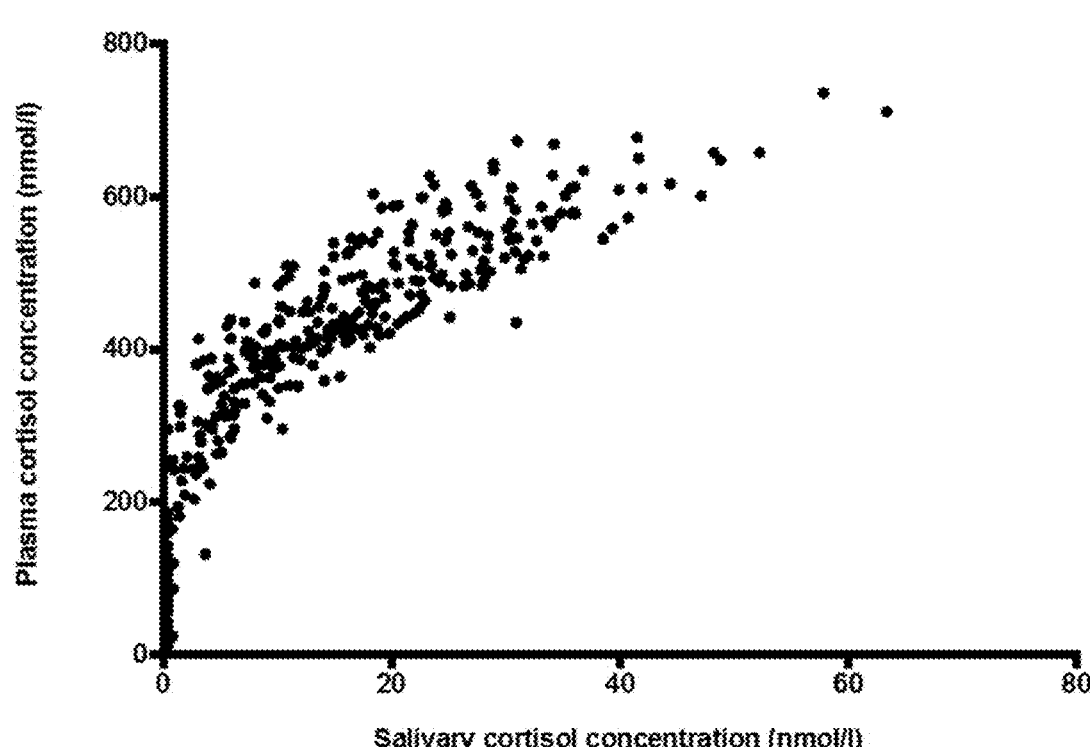
Figure 21:
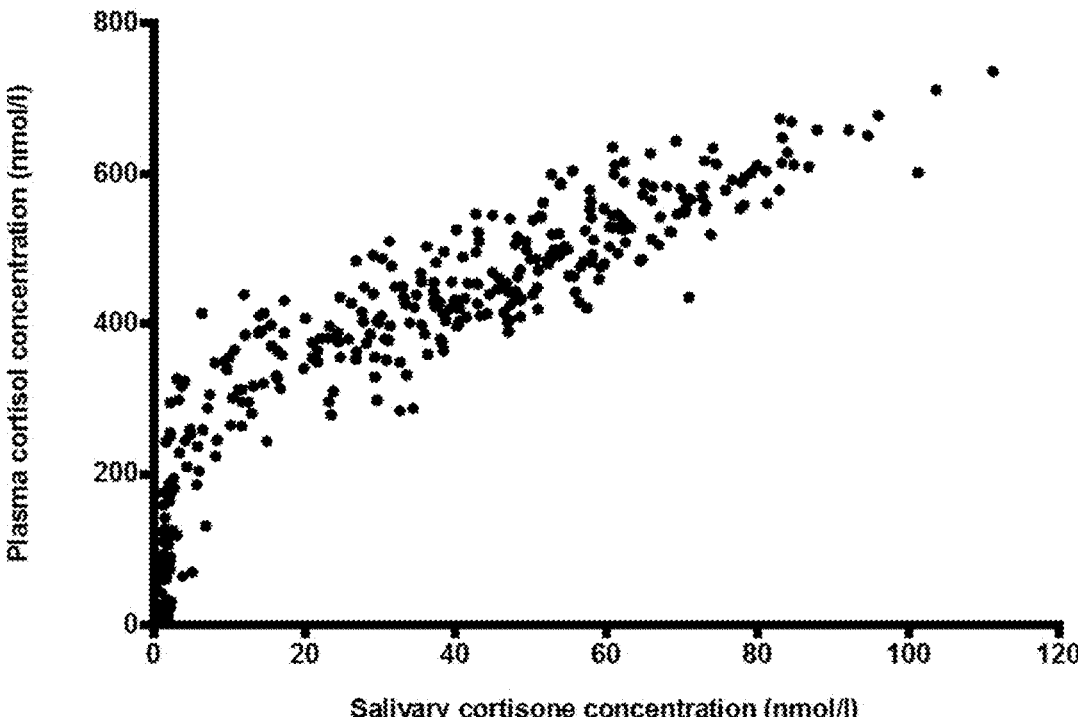
Figure 22A:
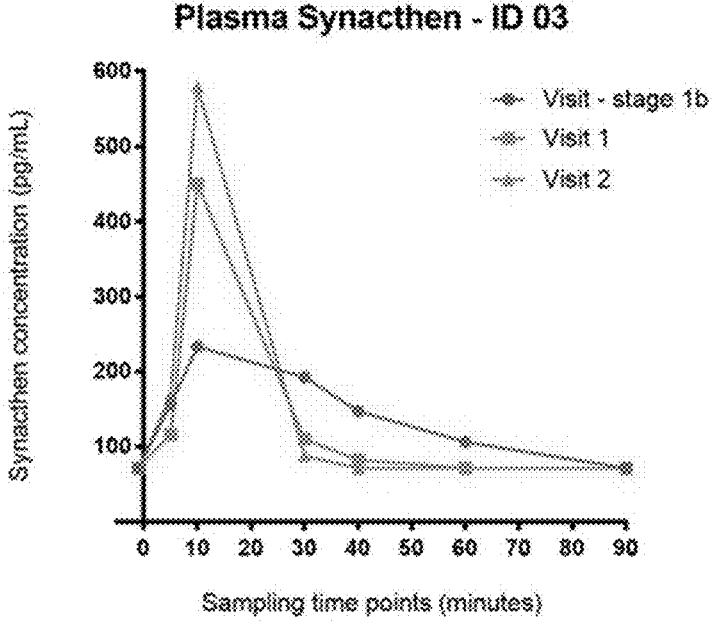
Figure 22A:
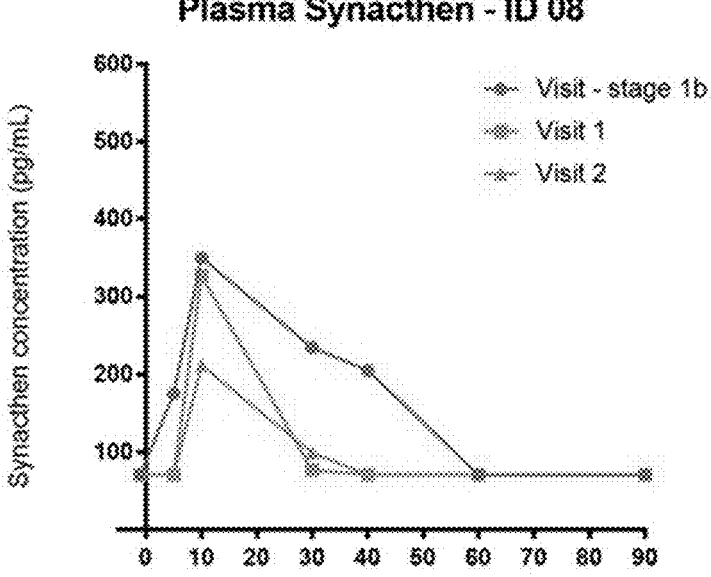
Figure 22B:
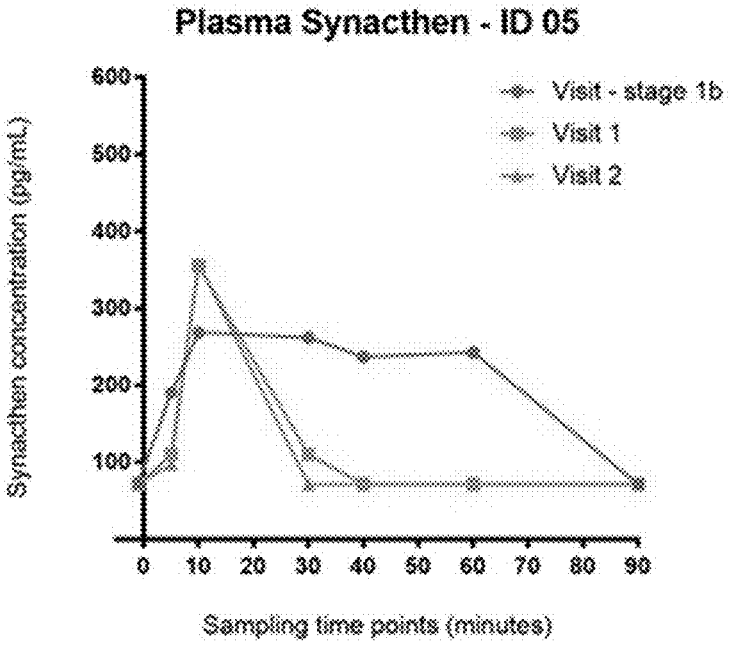
Figure 22B:
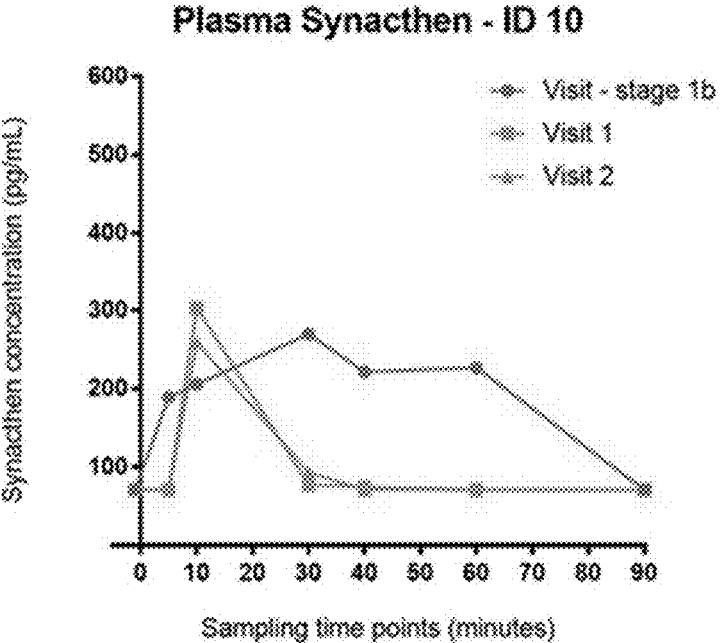
Figure 22C:
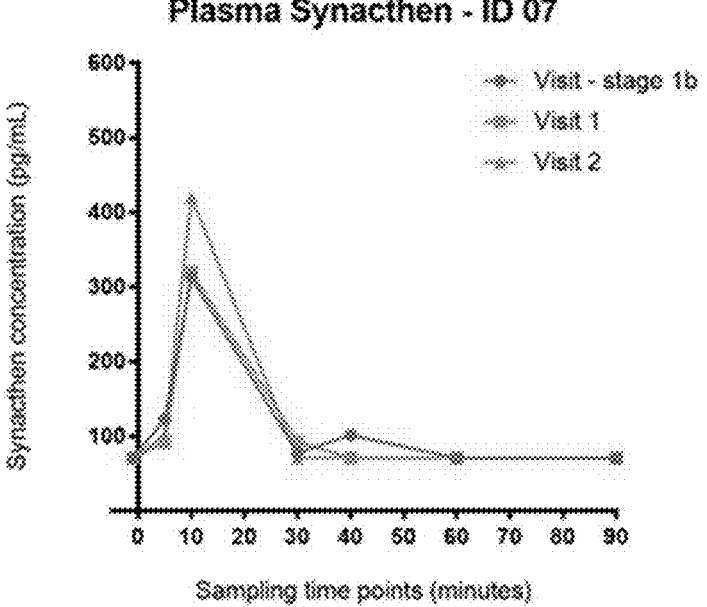
Figure 22C:
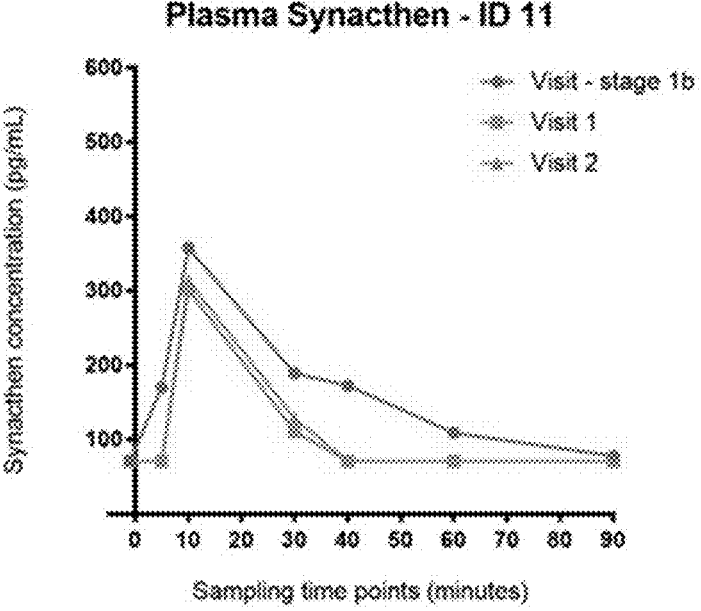
Figure 23A:
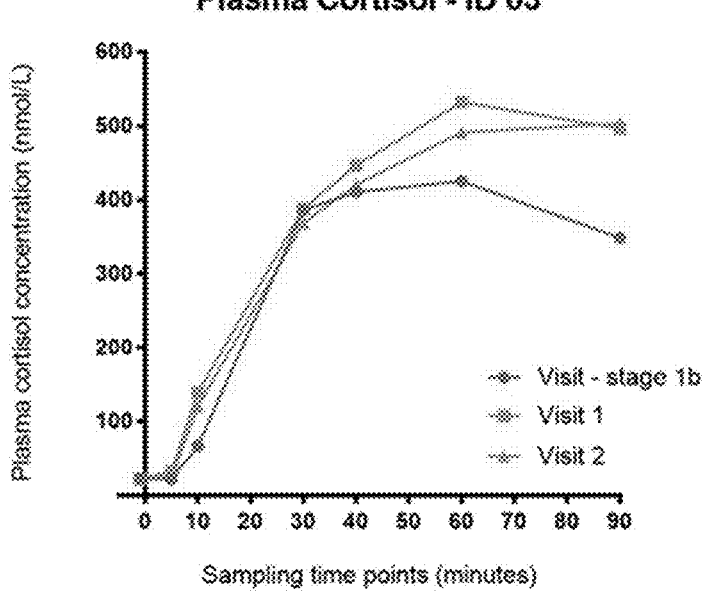
Figure 23A:
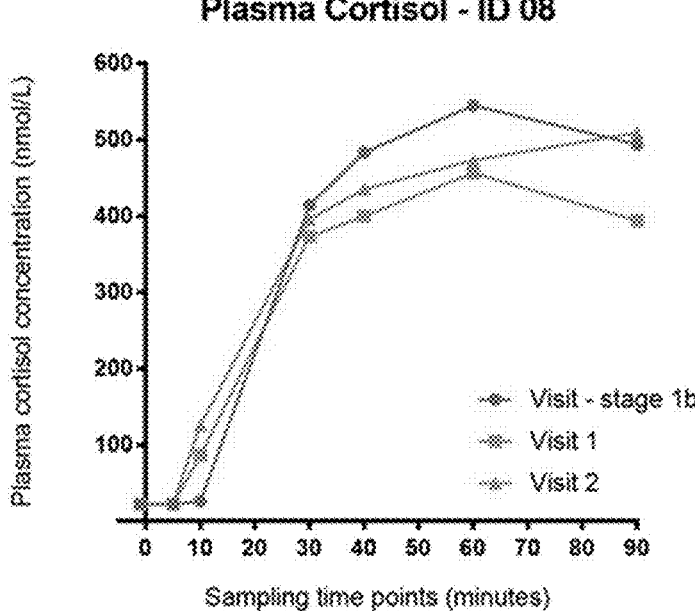
Figure 23B:
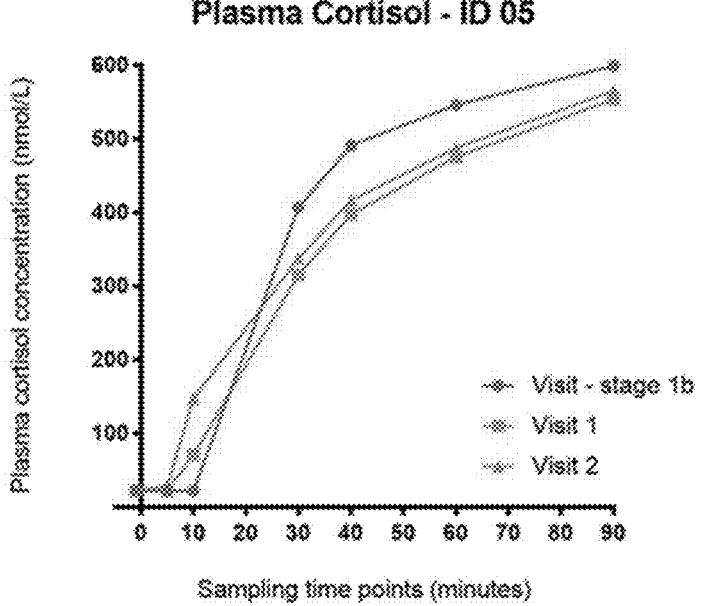
Figure 23B:
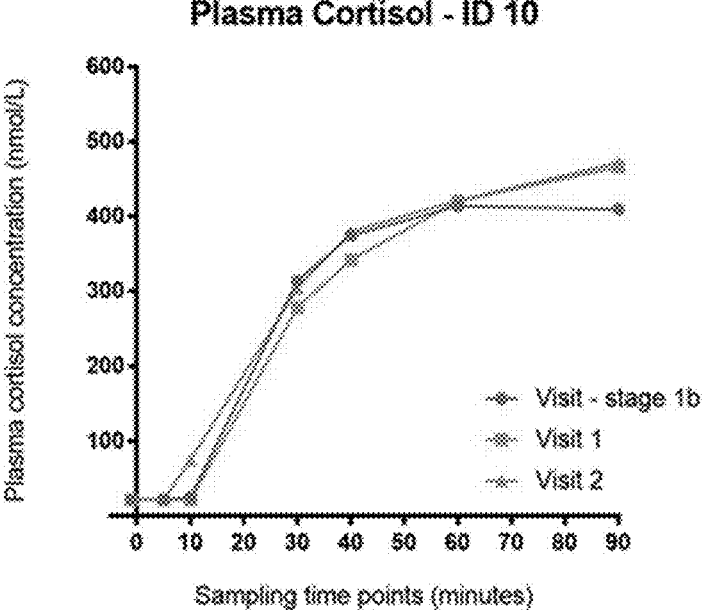
Figure 23C:
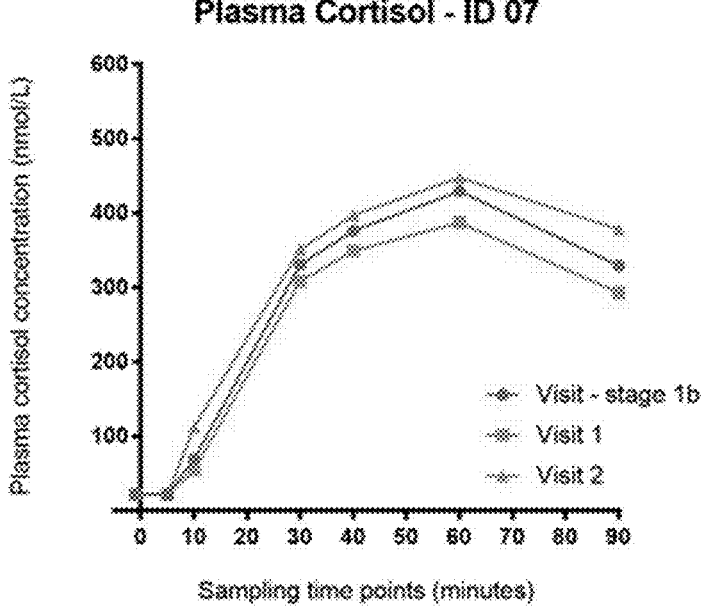
Figure 23C:
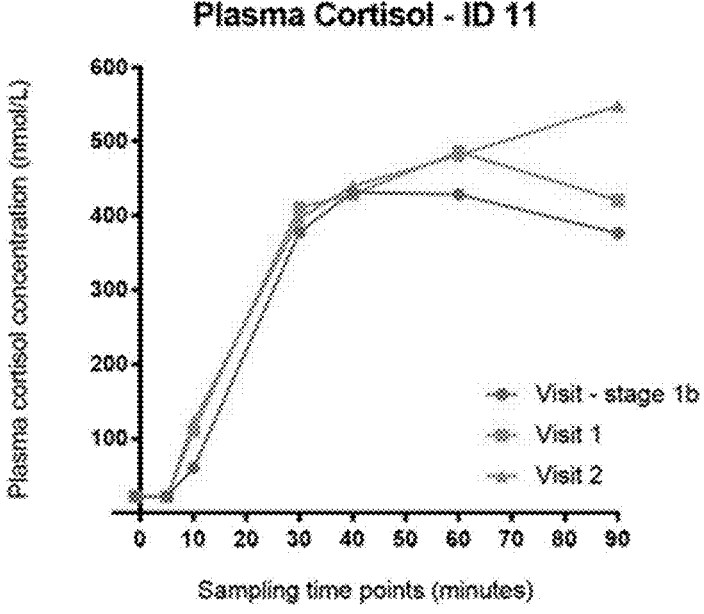
Figure 24A:
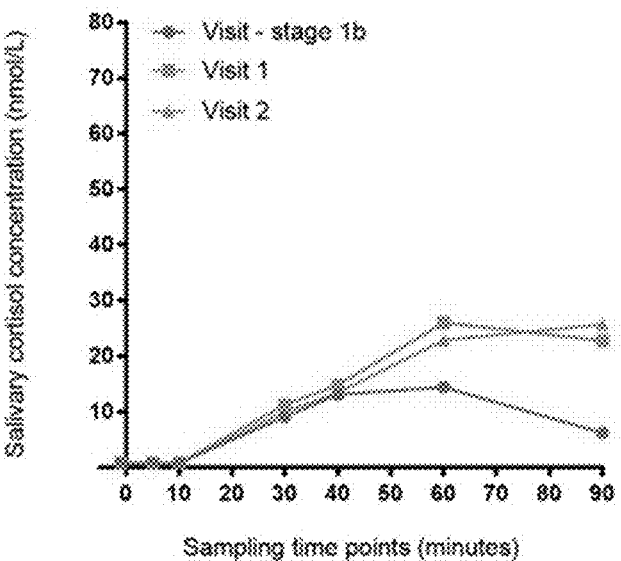
Figure 24A:
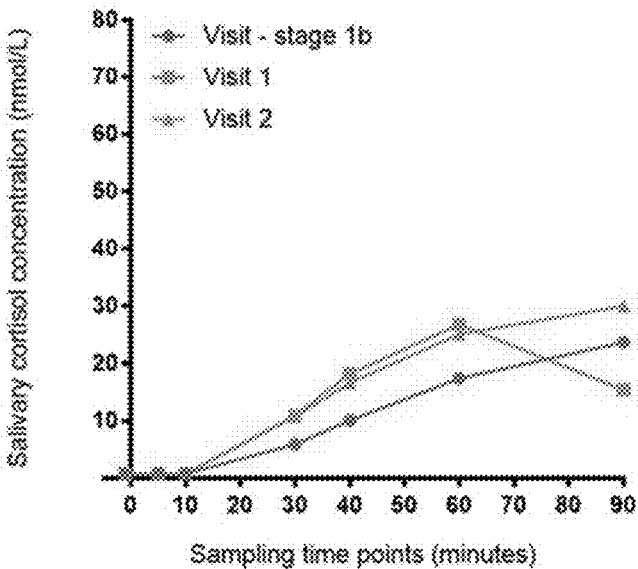
Figure 24B:
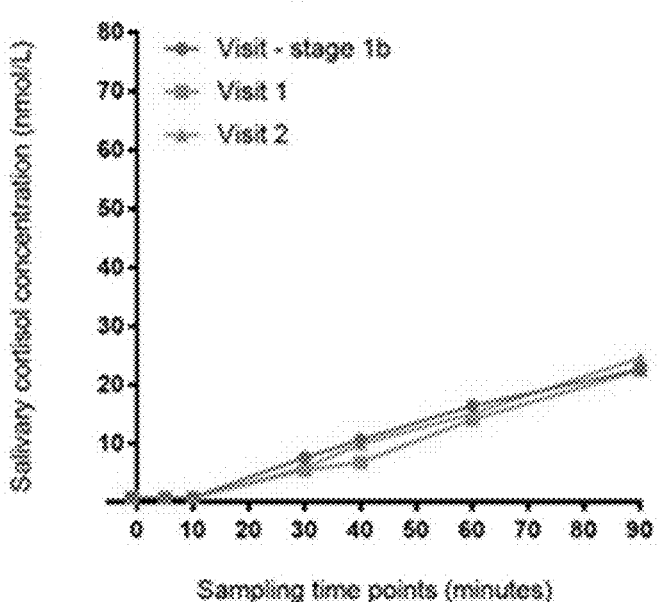
Figure 24B:
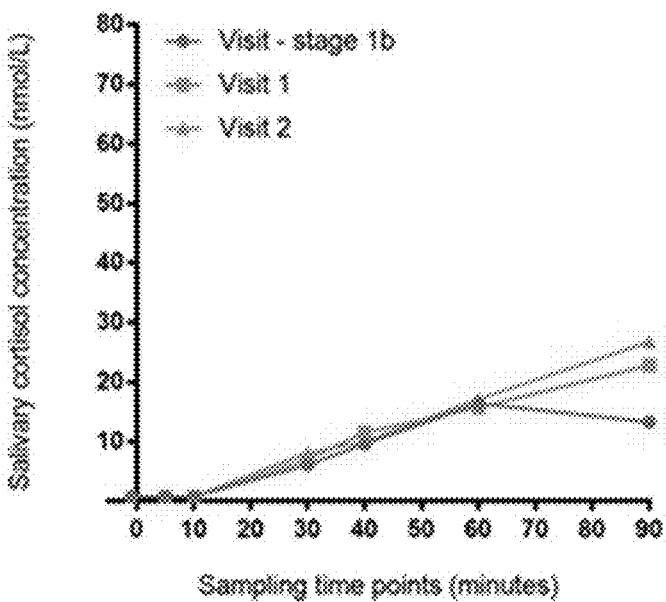
Figure 24C:
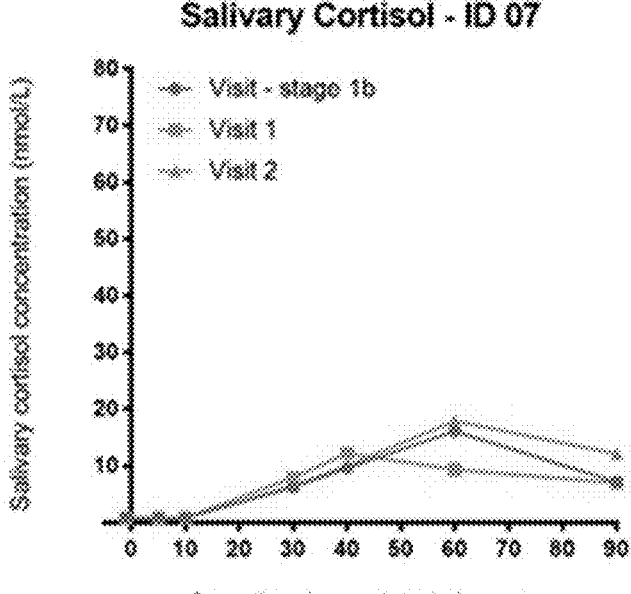
Figure 24C:
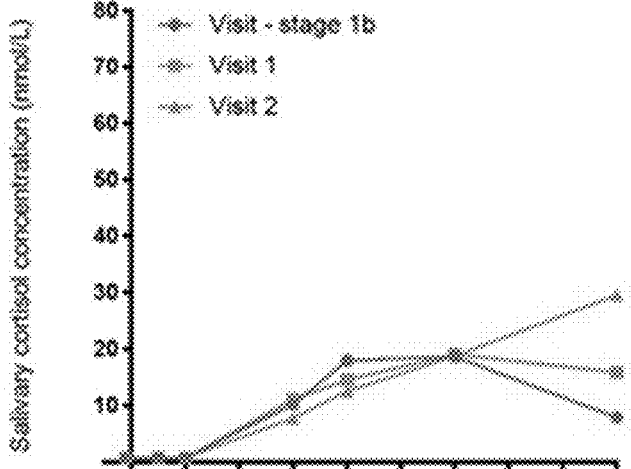
Figure 25A:
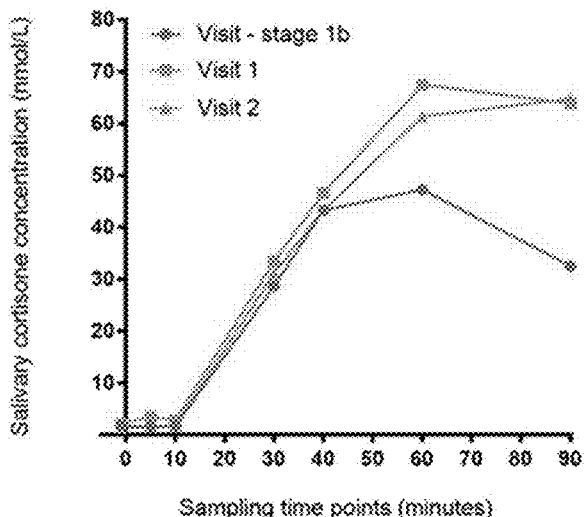
Figure 25A:
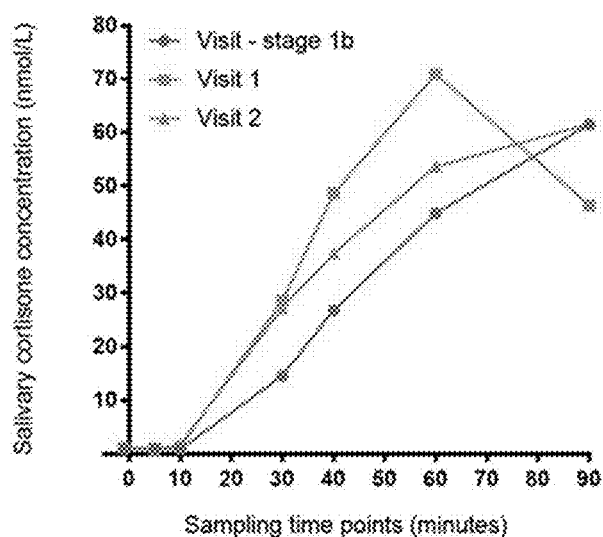
Figure 25B:
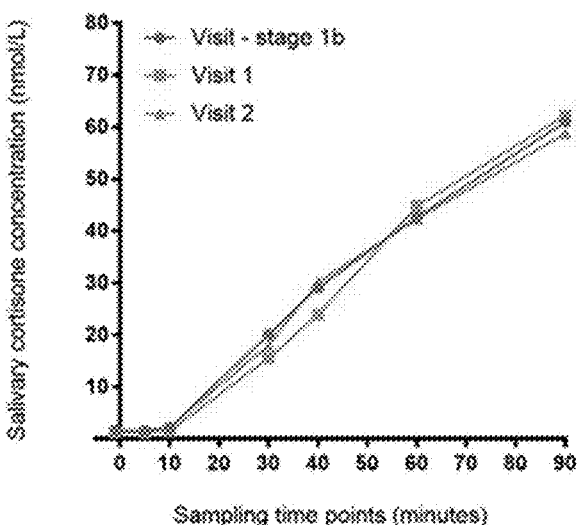
Figure 25B:
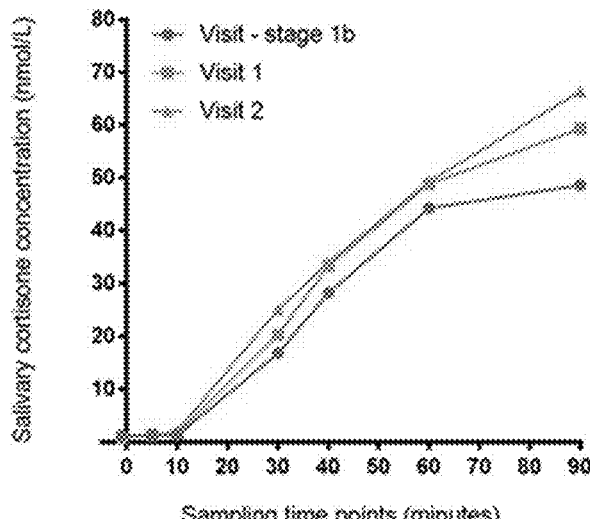
Figure 25C:
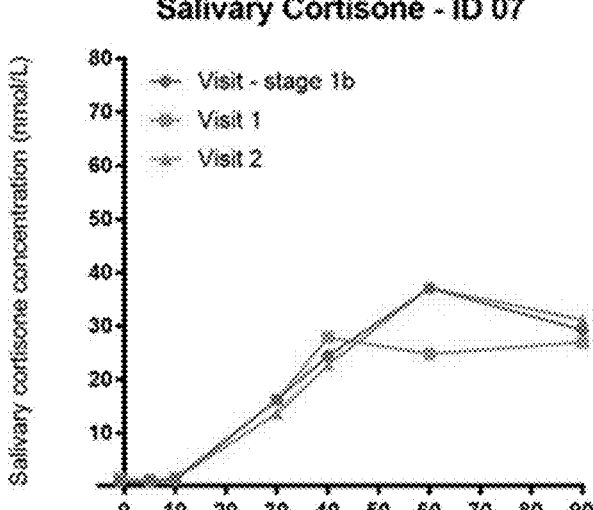
Figure 25C:
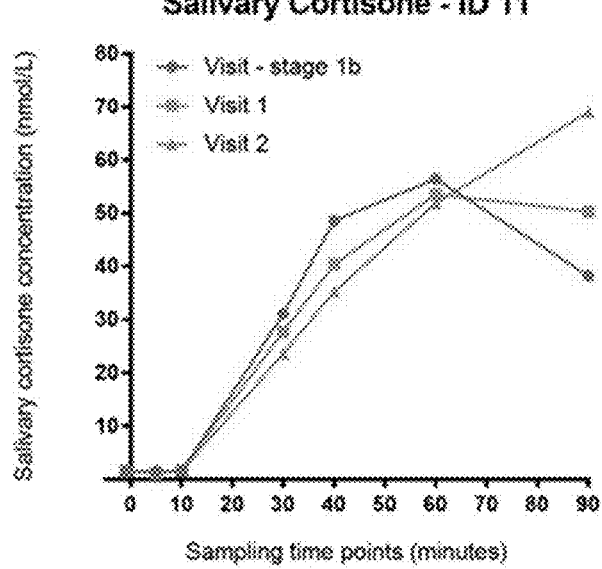
Figure 26:
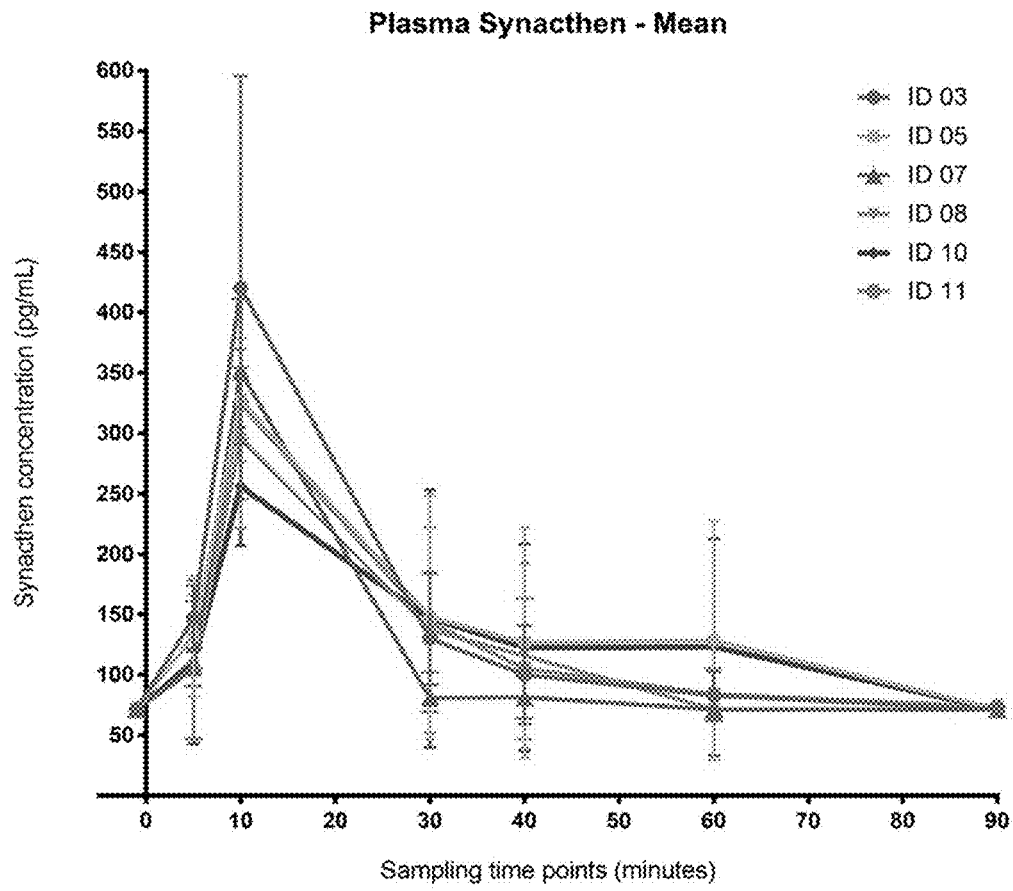
Figure 27:
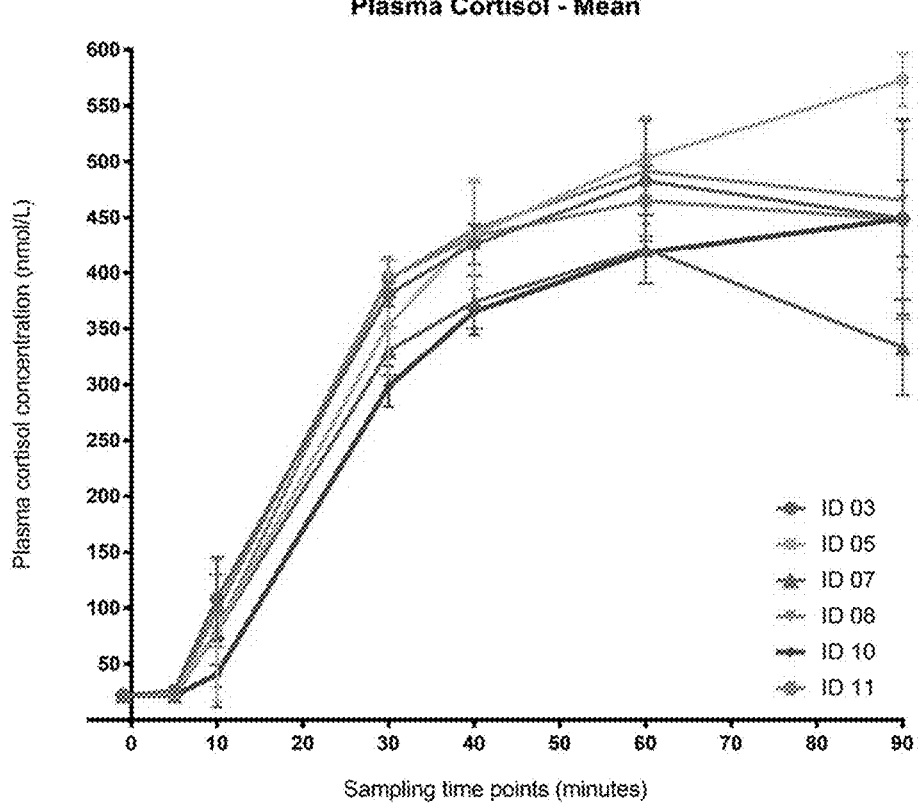
Figure 28:
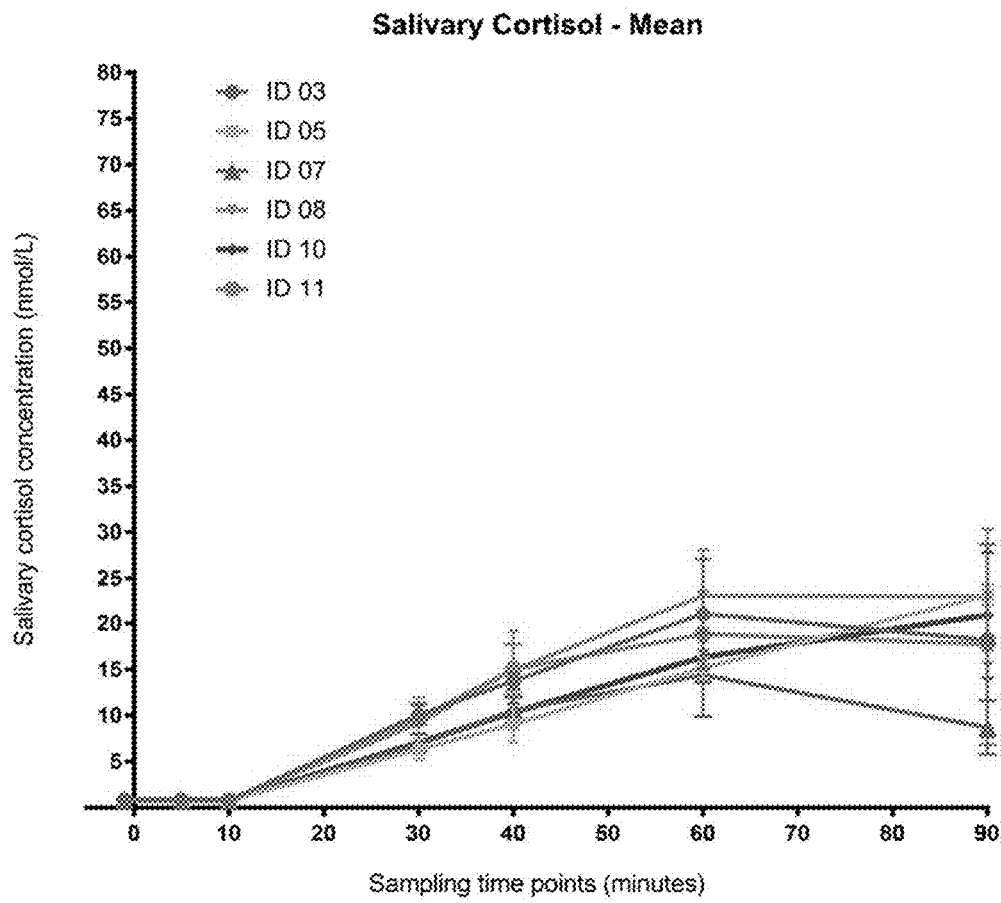
Figure 29:
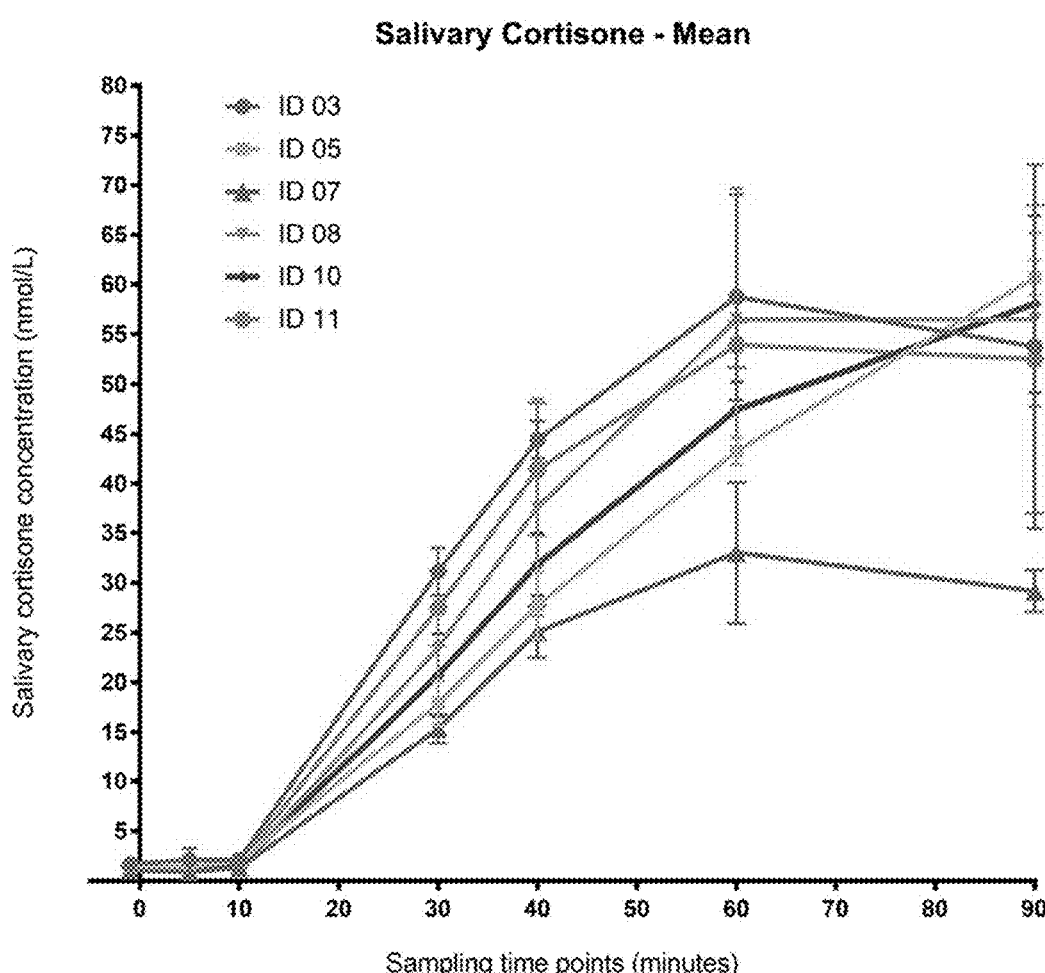
Figure 30:
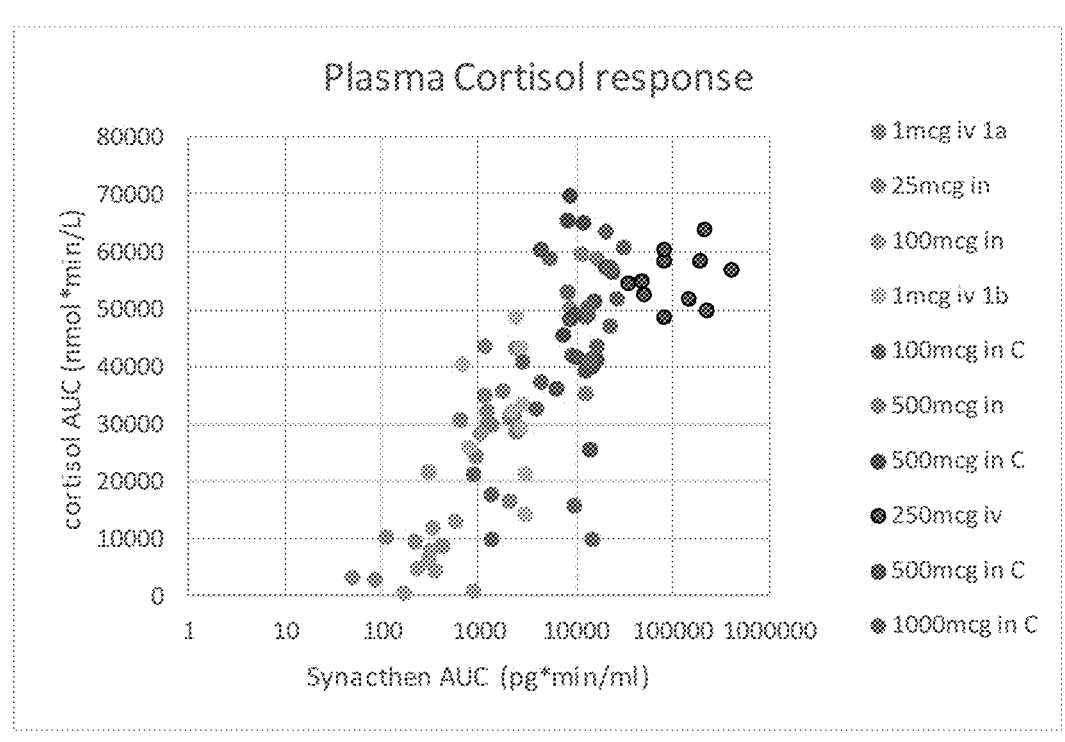
Figure 31A:
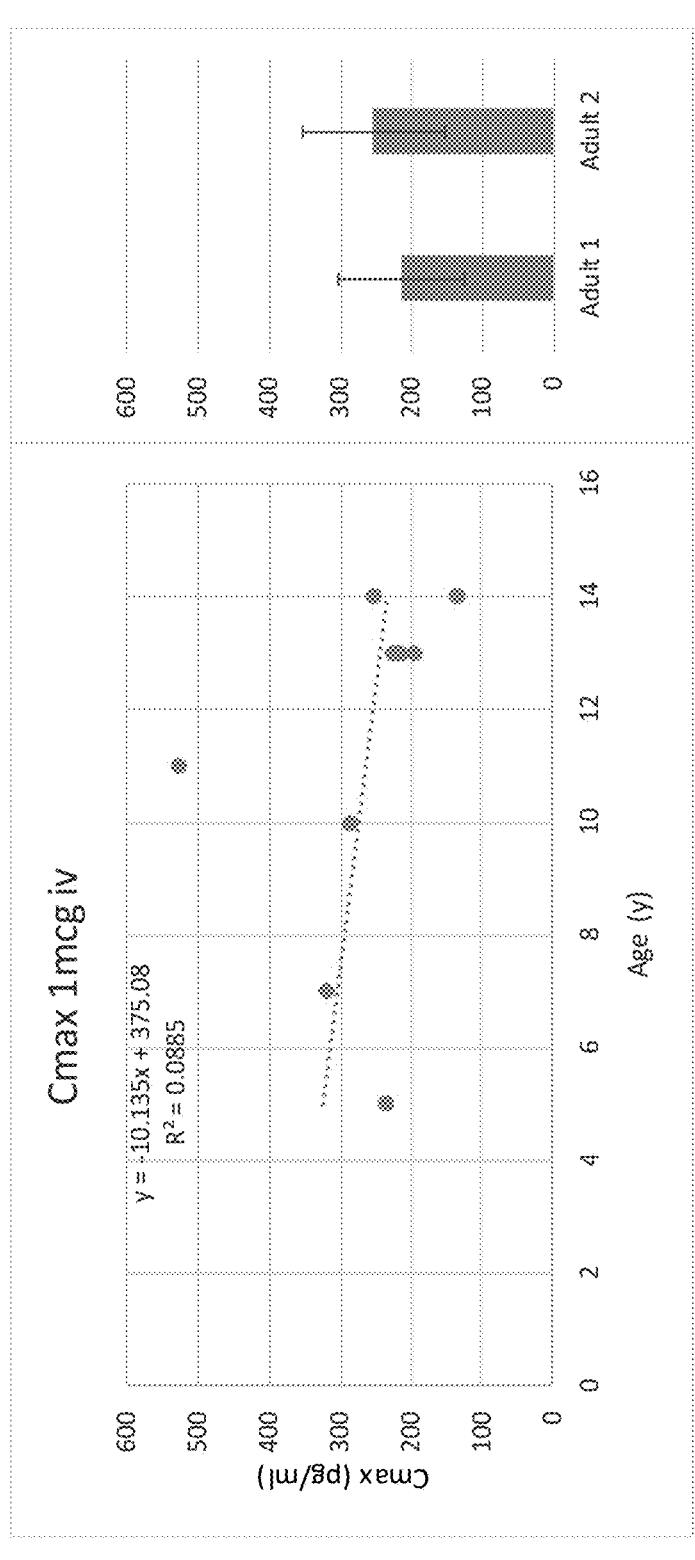
Figure 31B:
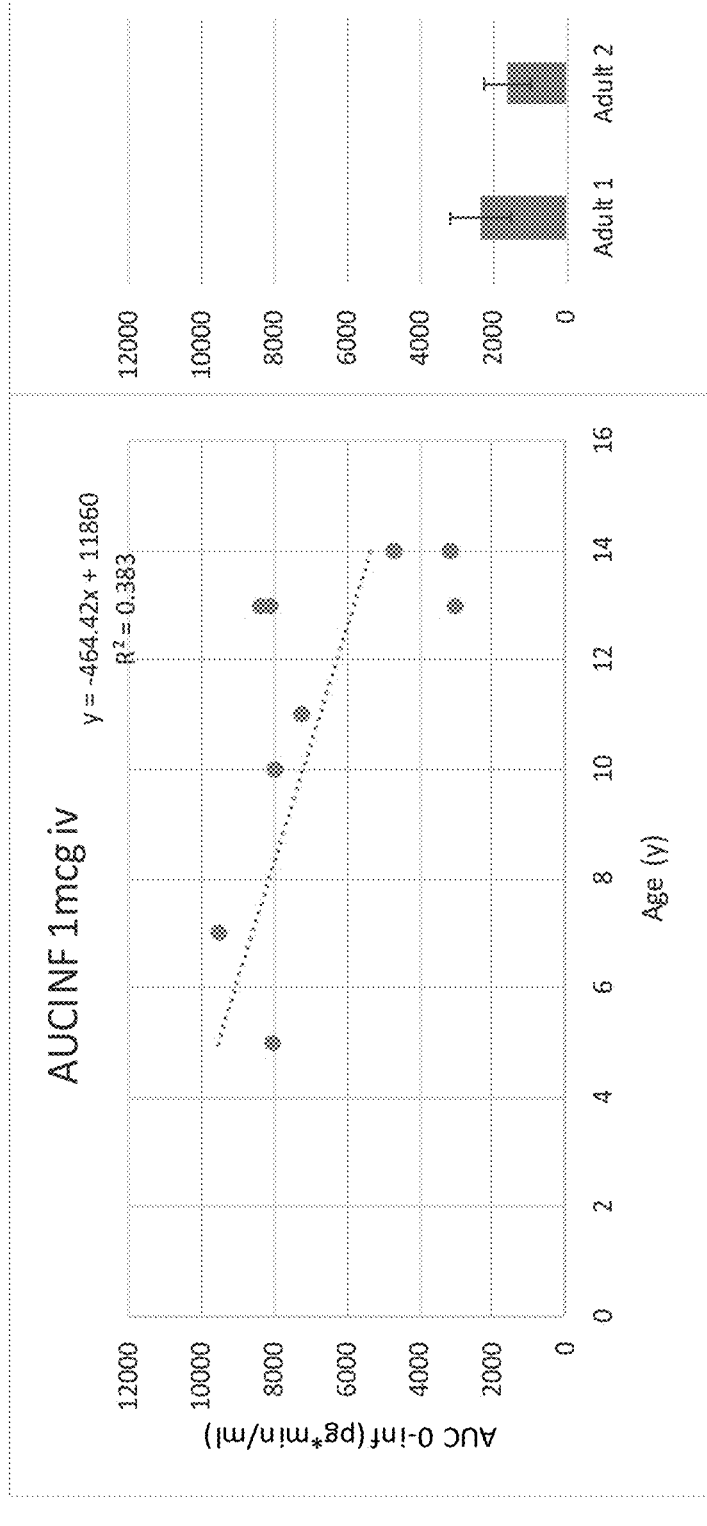
Figure 31C:
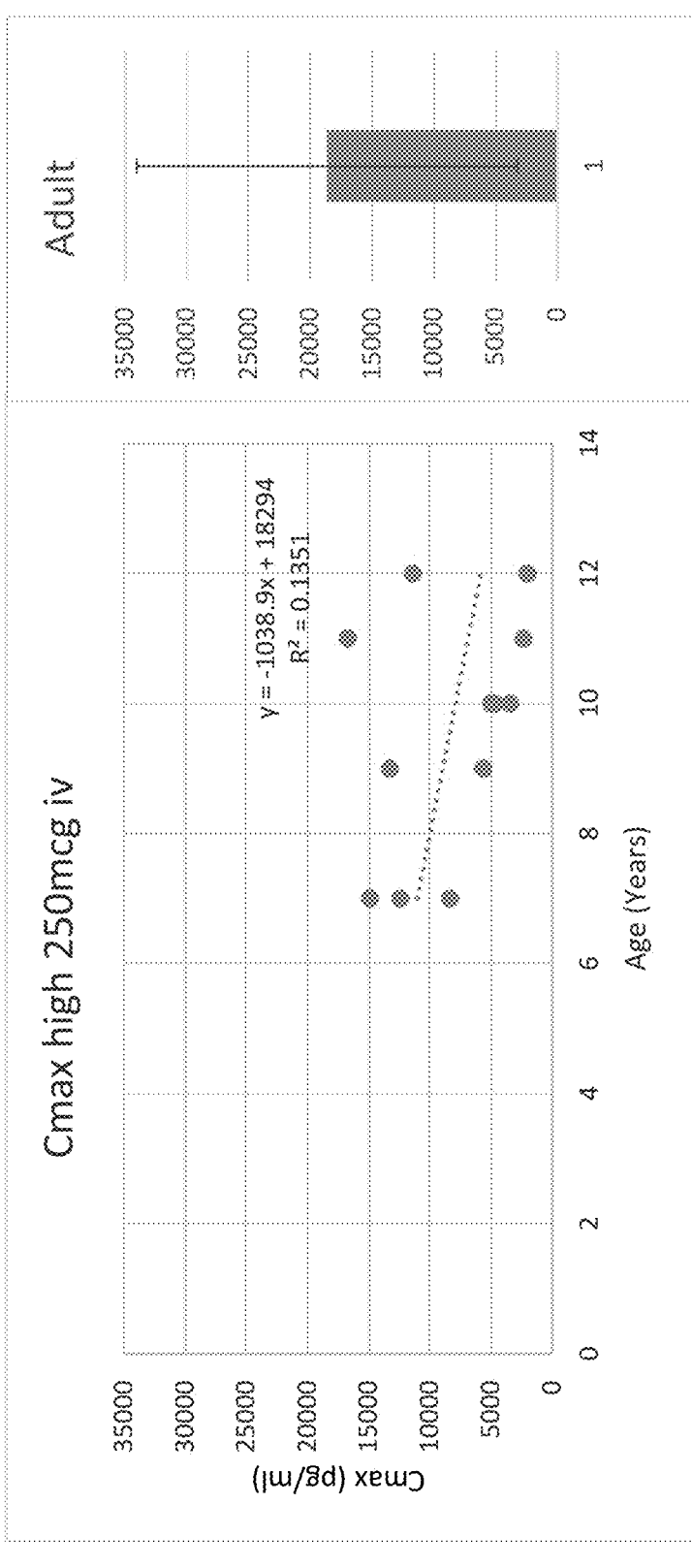
Figure 31D:
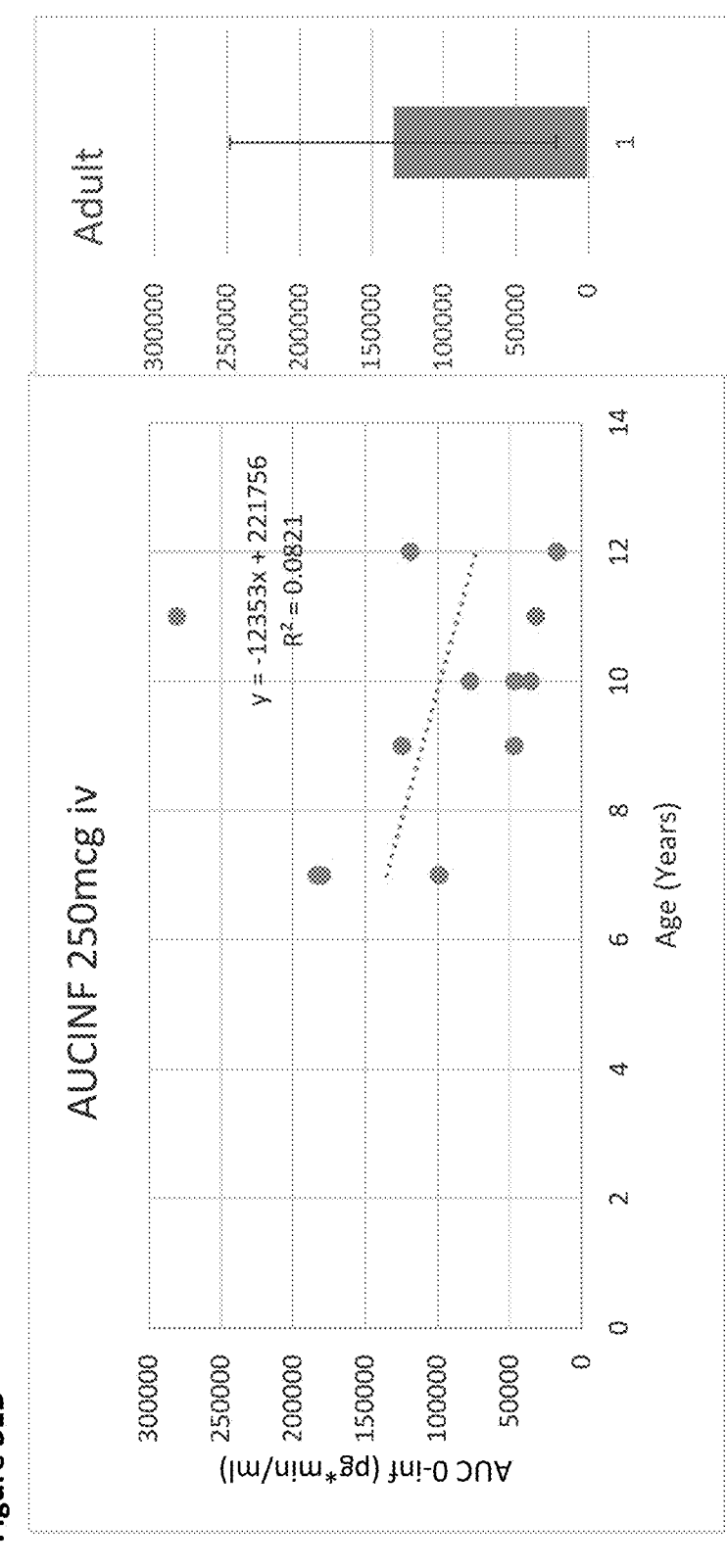

An embodiment of the invention will now be described by example only and with reference to the following figures:

FIG. 1: Graph of the mean rise of plasma Synacthen from baseline in subjects following administration with 1 mcg i.v, 100 mcg i.n and 25 mcg i.n Synacthen (STUDY 1, NeSST). Standard deviations shown as error bars;

FIG. 2: Graph of the mean rise of serum cortisol from a suppressed baseline in subjects following administration with 1 mcg i.v, 100 mcg i.n and 25 mcg i.n Synacthen (STUDY 1, NeSST). Standard deviations shown as error bars;

FIGS. 3A-3F: Comparison individual study volunteers' (A-C) plasma Synacthen levels and (D-F) serum cortisol responses to 1 mcg i.v Synacthen and three doses of nasal Synacthen (100 mcg with chitosan, 500 mcg and 500 mcg with chitosan) (STUDY 2 NeSST2 1a);

FIG. 4: Graph of the mean rise of plasma Synacthen from a suppressed baseline in subjects following administration with 1 mcg i.v, 500 mcg tetracosactide i.n, 100 mcg tetracosactide+chitosan i.n and 500 mcg tetracosactide+chitosan i.n (STUDY 2 NeSST2 1a). Standard deviations shown as error bars;

FIG. 5: Graph of the mean rise of serum cortisol from a suppressed baseline in subjects following administration with 1 mcg i.v, 500 mcg tetracosactide i.n, 100 mcg tetracosactide+chitosan i.n and 500 mcg tetracosactide+chitosan i.n. (STUDY 2 NeSST 1a). Standard deviations shown as error bars. Light blue line depicts a "normal" response on LDSST—500 nmol/L;

FIG. 6: Mean rise of serum cortisol from a suppressed baseline in subjects following Synacthen administration with 1 mcg i.v (data from STUDY 1 NeSST and STUDY 2 NeSST2 1a), 100 mcg i.n (NeSST), 100 mcg tetracosactide+chitosan i.n, 500 mcg tetracosactide i.n and 500 mcg tetracosactide+chitosan i.n. Standard deviations not shown for clarity. Light blue line depicts a "normal" response on LDSST—500 nmol/L;

FIG. 7: Box and Whisker plot of plasma Synacthen Area Under the Curve for different doses of Synacthen administered in STUDY 1 NeSST and STUDY 2 NeSST2 1a Studies;

FIGS. 8A-8C: Individual plasma Synacthen responses to 250 mcg IV (FIG. 8A), 1 mg IN (FIG. 8B) and 500 mcg IN (FIG. 8C) doses (STUDY 3 NeSST2 1b);

FIG. 9: Individual participants' plasma cortisol responses over time following 250 mcg IV Synacthen at 0 minutes (STUDY 3 NeSST2 1b);

FIG. 10: Individual participants' plasma cortisol responses over time following 500 mcg IN Synacthen at 0 minutes (STUDY 3 NeSST2 1b);

FIG. 11: Individual participants' plasma cortisol responses over time following 1 mg IN Synacthen at 0 minutes (STUDY 3 NeSST2 1b);

FIGS. 12A-12L: Individual participants' plasma cortisol responses over time following 250 mcg IV, 1 mg IN and 500 mcg IN Synacthen at 0 minutes (STUDY 3 NeSST2 1b);

FIG. 13: Scatterplot of paired serum and salivary cortisol samples following administration with 4 formulations of Synacthen in STUDY 2 NeSST2 1a (salivary cortisol below the limit of assay detection displayed as 0.74 nmol/L and serum cortisol as 21 nmol/L) N=671;

FIG. 14: Scatterplot of paired salivary cortisol and cortisone samples following administration with 4 formulations of Synacthen in STUDY 2 NeSST2 1a (salivary cortisol below the limit of assay detection displayed as 0.74 nmol/L and salivary cortisone as 0.4 nmol/L) N=674;

FIG. 15: Scatterplot of paired serum cortisol and salivary cortisone samples following administration with 4 doses of Synacthen in STUDY 2 NeSST2 1a (serum cortisol below the limit of assay detection displayed as 21 nmol/L and salivary cortisone as 0.4 nmol/L) N=670;

FIG. 16: Mean serum cortisol, salivary cortisol and salivary cortisone responses over time following nasal administration with 500 mcg tetracosactide with chitosan (N=9) (STUDY 2 NeSST2 1a);

FIG. 17: Mean salivary cortisol concentrations of each test against time following 250 mcg IV, 1 mg IN and 500 mcg IN Synacthen at 0 minutes (STUDY 3 NeSST2 1b). Standard deviation bars included;

FIG. 18: Mean salivary cortisone concentration of each test against time following 250 mcg IV, 1 mg IN and 500 mcg IN Synacthen at 0 minutes (STUDY 3 NeSST2 1b) Standard deviation bars included;

FIG. 19: Scatter plot of paired salivary cortisol and cortisone samples following administration with 3 formulations of Synacthen in STUDY 3 NeSST2 1b;

FIG. 20: Scatter plot paired serum cortisol and salivary cortisol samples following administration with 3 formulations of Synacthen in STUDY 3 NeSST2 1b;

FIG. 21: Scatter plot paired serum cortisol and salivary cortisone samples following administration with 3 formulations of Synacthen in STUDY 3 NeSST2 1b;

FIGS. 22A-22C: Plasma Synacthen over time for 6 participants receiving 3 doses of 500 mcg IN Synacthen (visit stage 1b unprimed mucosal atomiser device therefore lower and more variable dose delivered compared to visit 1 and 2—STUDY 4 NeSST2 1c);

FIGS. 23A-23C: Plasma cortisol over time for 6 participants receiving 3 doses of 500 mcg IN Synacthen (visit stage 1b unprimed mucosal atomiser device therefore lower and more variable dose delivered compared to visit 1 and 2—STUDY 4 NeSST2 1c);

FIGS. 24A-24C: Salivary cortisol over time for 6 participants receiving 3 doses of 500 mcg IN Synacthen (visit stage 1b unprimed mucosal atomiser device therefore lower and more variable dose delivered compared to visit 1 and 2—STUDY 4 NeSST2 1c);

FIGS. 25A-25C: Salivary cortisone over time for 6 participants receiving 3 doses of 500 mcg IN Synacthen (visit stage 1b unprimed mucosal atomiser device therefore lower and more variable dose delivered compared to visit 1 and 2—STUDY 4 NeSST2 1c);

FIG. 26: Mean plasma Synacthen for 6 participants receiving three doses of 500 mcg IN Synacthen (STUDY 4 NeSST2 1c)—SD error bars included;

FIG. 27: Mean plasma cortisol for 6 participants receiving three doses of 500 mcg IN Synacthen (STUDY 4 NeSST2 1c)—SD error bars included;

FIG. 28: Mean salivary cortisol for 6 participants receiving three doses of 500 mcg IN Synacthen (STUDY 4 NeSST2 1c)—SD error bars included;

FIG. 29: Mean salivary cortisone for 6 participants receiving three doses of 500 mcg IN Synacthen (STUDY 4 NeSST2 1c)—SD error bars included;

FIG. 30: Exposure response curve for different doses of intravenous synacthen and Nasacthin (see legend); A maximal response in terms of plasma cortisol AUC(0-t) is achieved with a synacthen AUC of around 10,000 pg*min/ml. The 500 mcg Nasacthin dose gives a cortisol response near to the maximum and comparable to 250 mcg iv synacthen, a higher dose of 1000 mcg Nasacthin does not improve the response.

Figure 32:
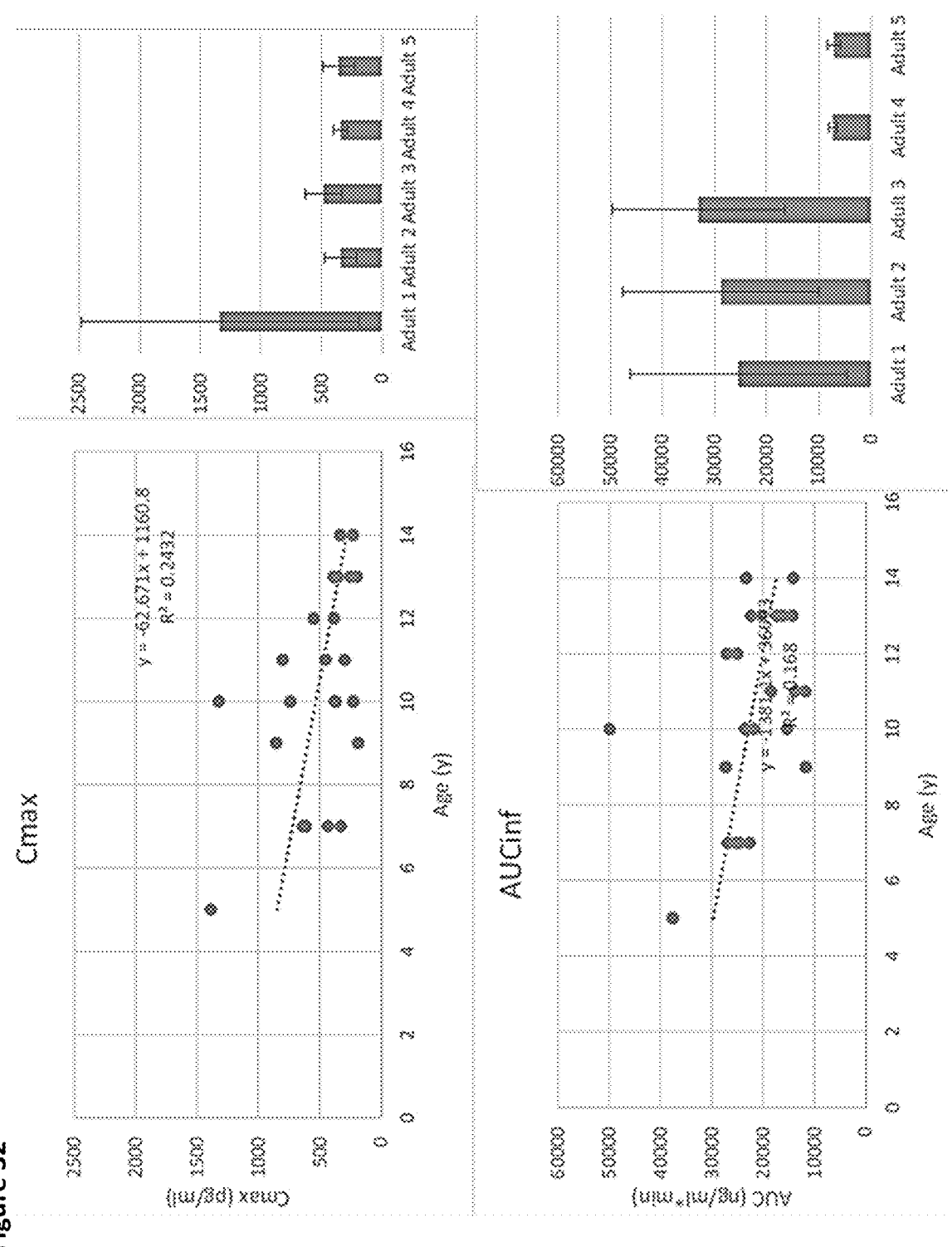
Figure 33A:
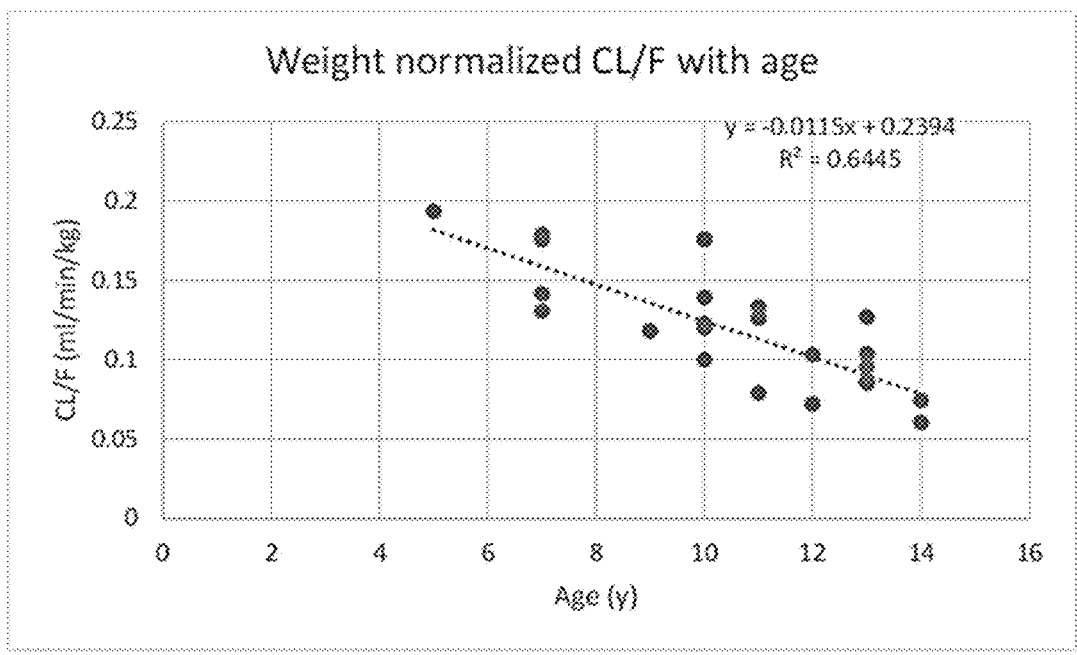
Figure 33B:
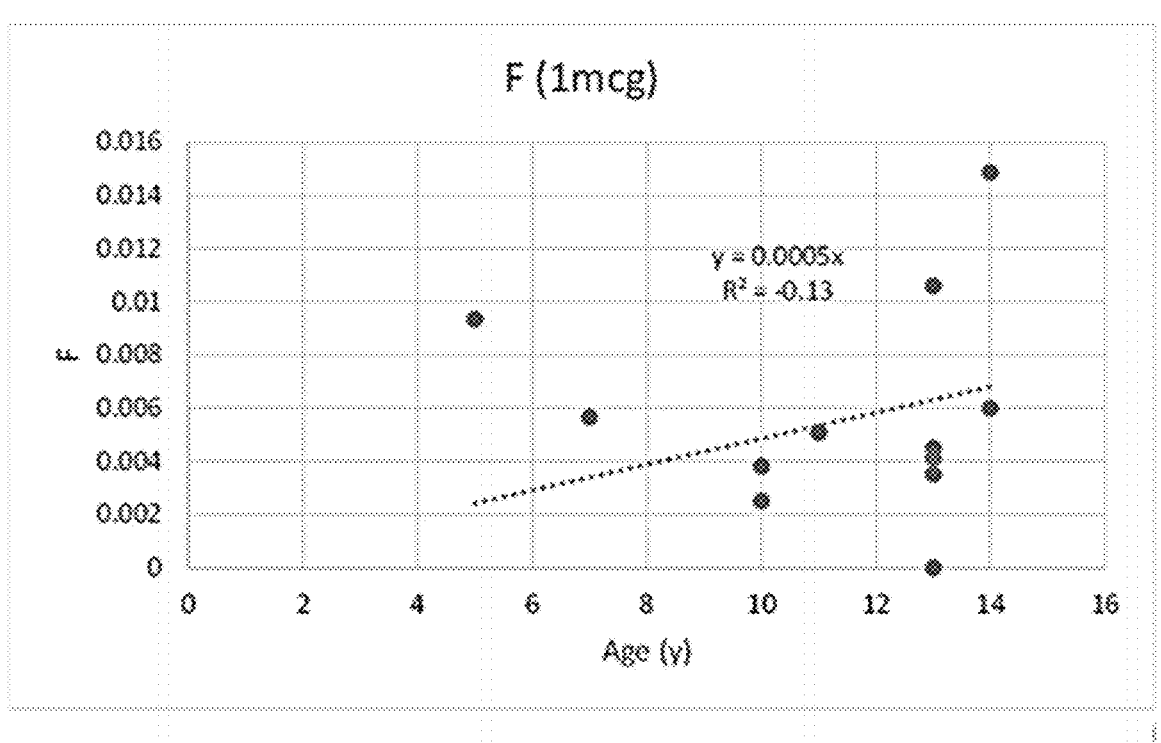
Figure 33C:
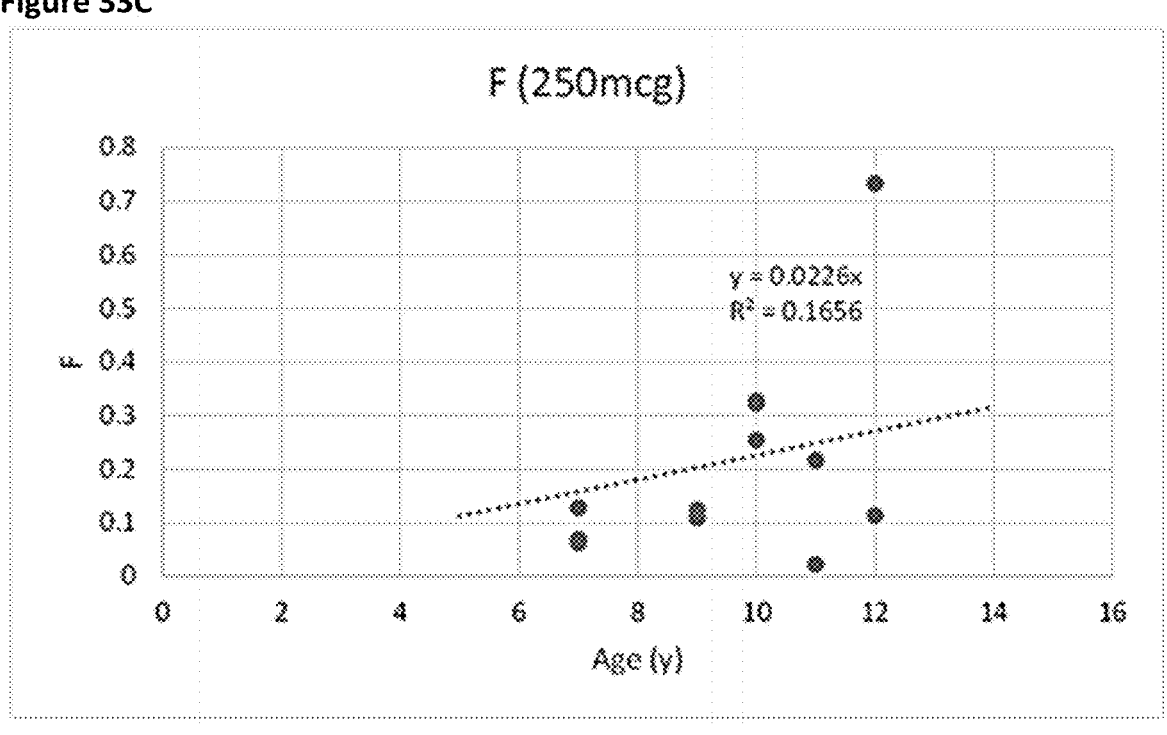

FIGS. 31A-31D Cmax and AUC(0-inf) against age in individual paediatric subjects for 1 mcg (FIGS. 31A and 31B) and 250 mcg (FIGS. 31C and 31D) iv doses of synacthen (LHS of each plot) compared against mean±SD results for the same doses in adult subjects from previous NeSST studies (RHS of each plot on same scale). The exposure to synacthen is as expected slightly higher in the paediatric population especially at younger age due to smaller body size. However, exposure is in line with the adult data where significant variability was seen;

FIG. 32 Cmax and AUC(0-inf) against age in individual paediatric subjects for a 500 mcg (bottom) dose of Nasacthin (LHS of each plot) compared against mean±SD results for the same doses in adult subjects from previous NeSST studies (RHS of each plot on same scale); the exposure to Nasacthin is as expected slightly higher in the paediatric population especially at younger age due to smaller body size. However, exposure is in line with the adult data where significant variability was seen. Some of this variability may be explained because of the original assay sensitivity for synacthen, a better more sensitive assay was used in Studies 3, 4+5;

FIGS. 33A-33C Top plot showing Nasacthin clearance with Age for the 500 mcg dose, the bottom graphs show the calculated bioavailability for this intranasal dose based on both the 1 mcg and 250 mcg iv synacthen data; the decrease in Nasacthin clearance (CL/F) with age can be explained by an increase in corresponding bioavailability (F) with age. Presumably, at younger ages the smaller surface area of the nasal mucosa results in greater loss of the applied solution and therefore a decreased F. The discrepant results for calculation of Nasacthin F with age between the 1 mcg and 250 mcg iv doses can be explained by assay sensitivity issues.

Figure 34A:
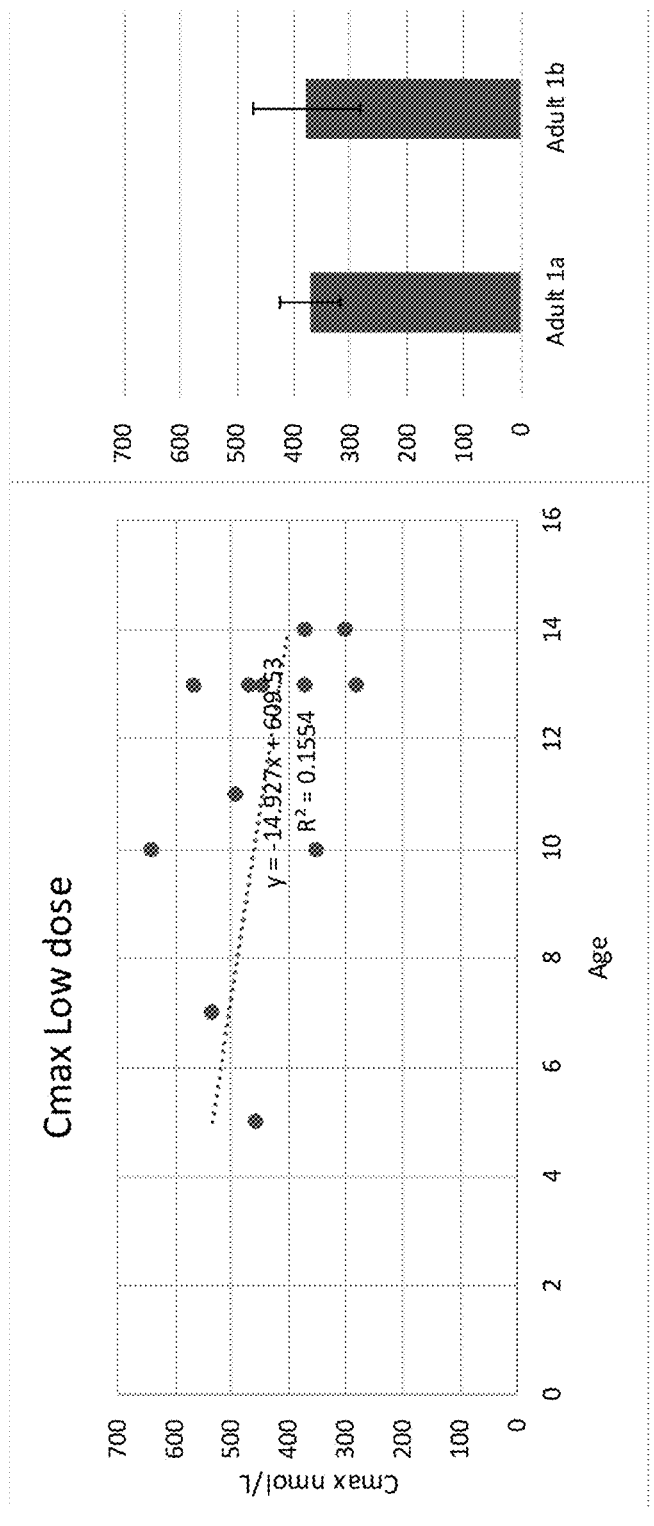
Figure 34B:
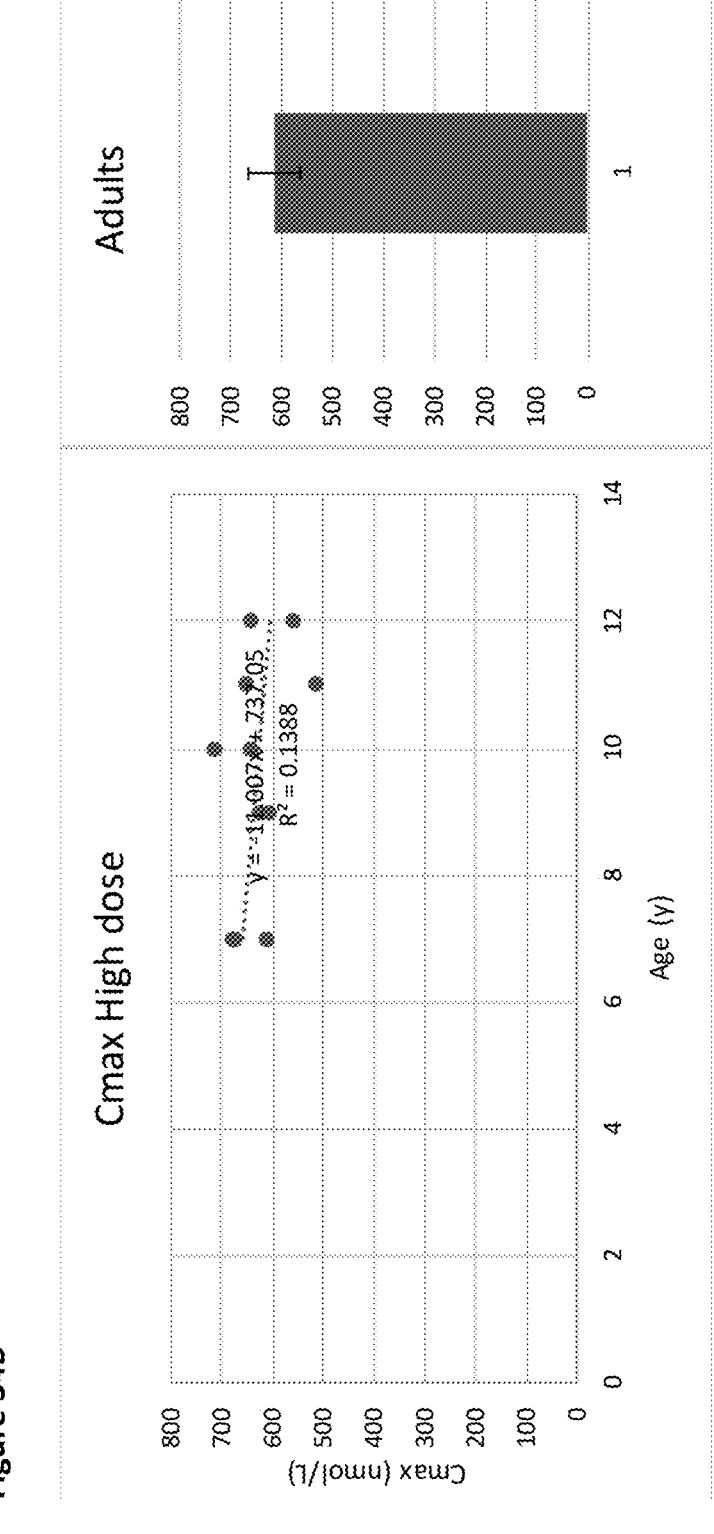
Figure 34C:
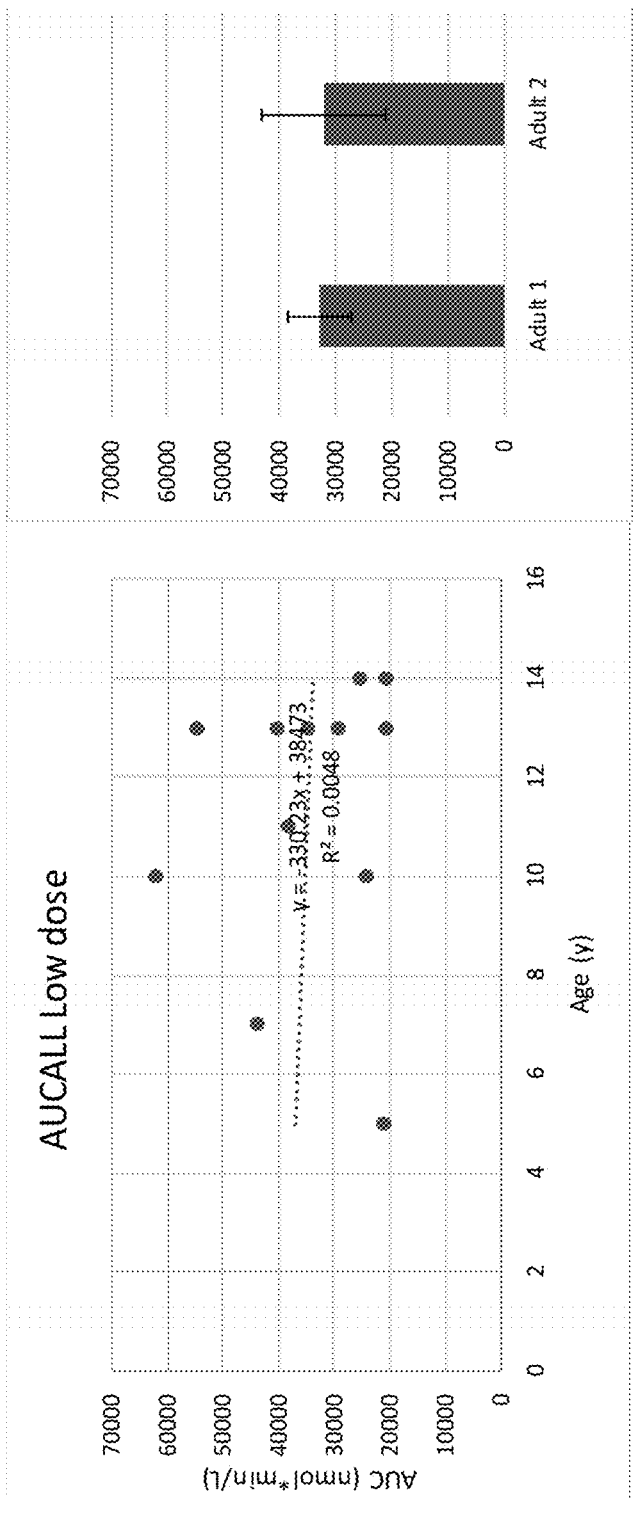
Figure 34D:
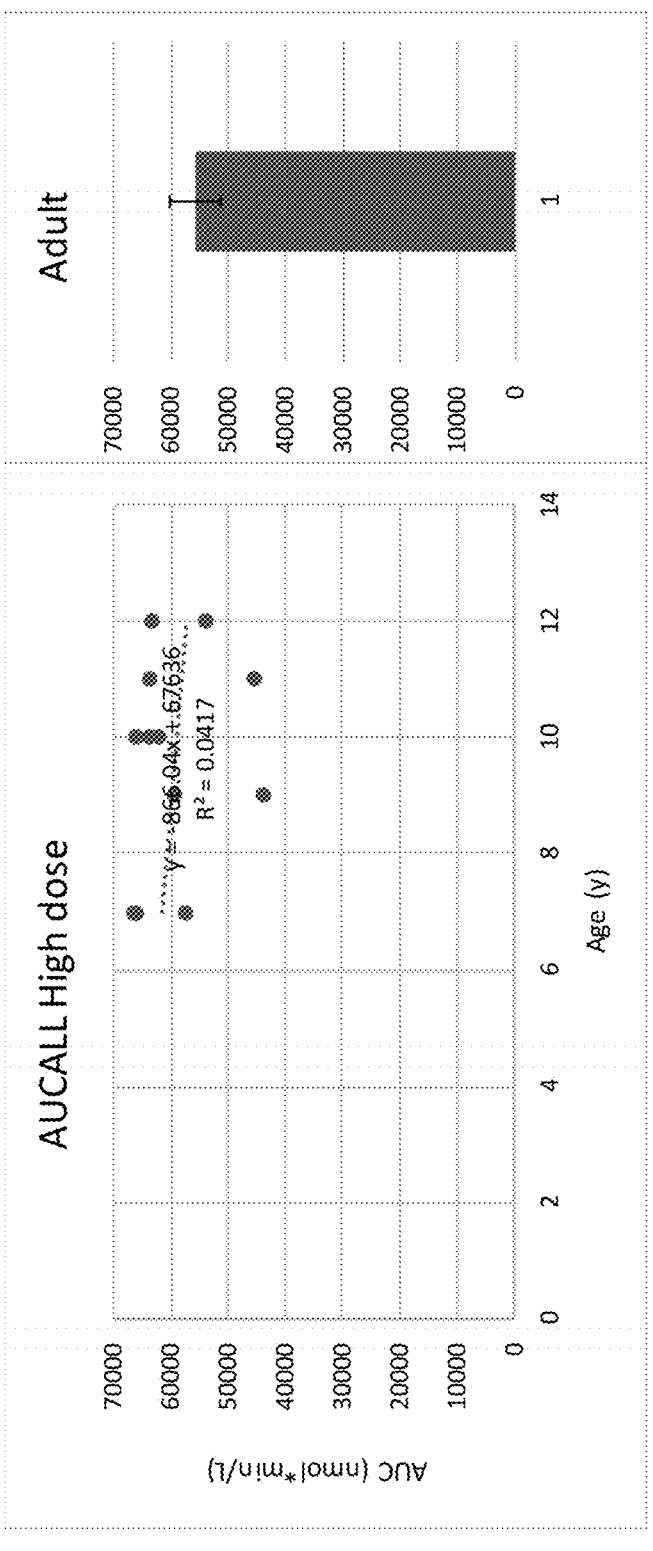

FIGS. 34A-34D Plasma cortisol response, Cmax and AUC, with age for individual paediatric subjects (LHS of each graph) following administration of the low (1 mcg; FIGS. 34A and 34C) and high (250 mcg; FIGS. 34B and 34D) intravenous doses of synacthen. The paediatric values are compared against mean±SD adult cortisol values (RHS of each graph). Overall the cortisol responses with age in the paediatric subjects were in line with those in adults.

Figure 35A:
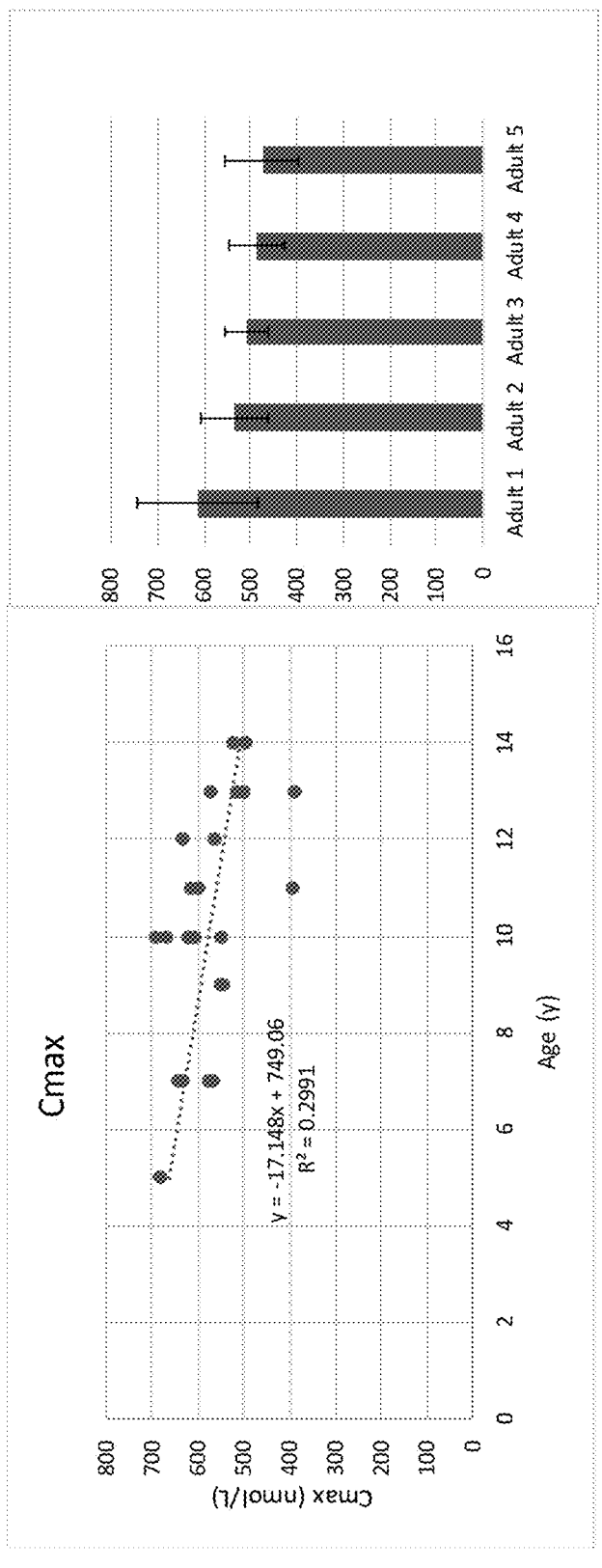
Figure 35B:
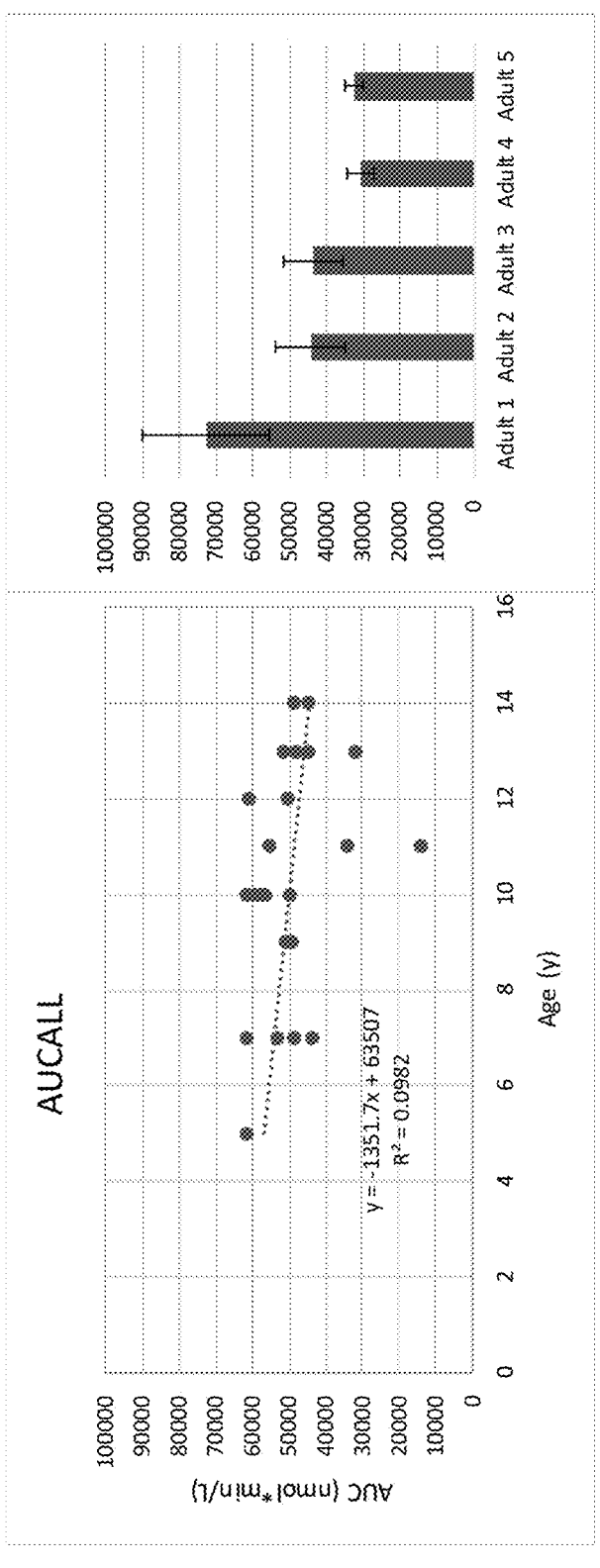
Figure 36A:
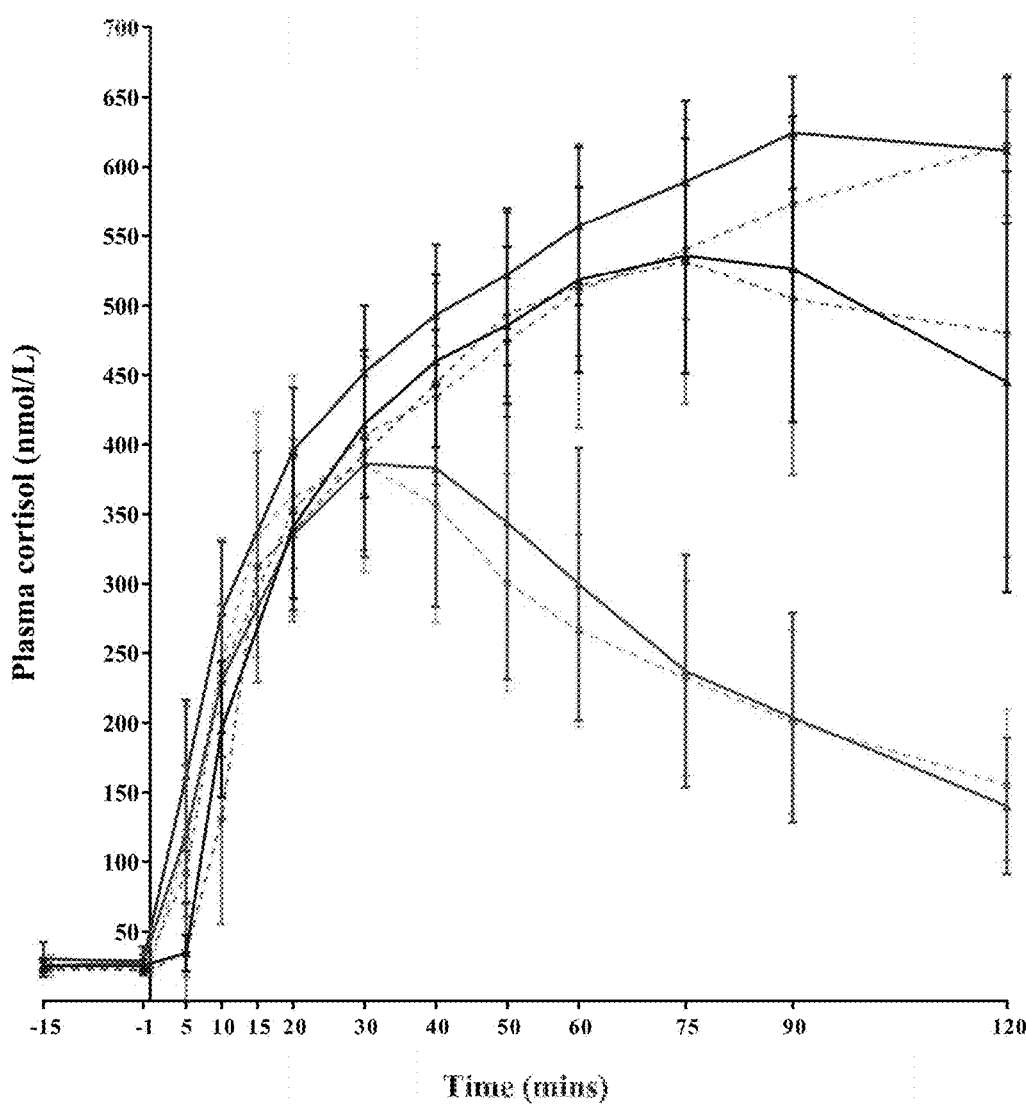
Figure 36B:
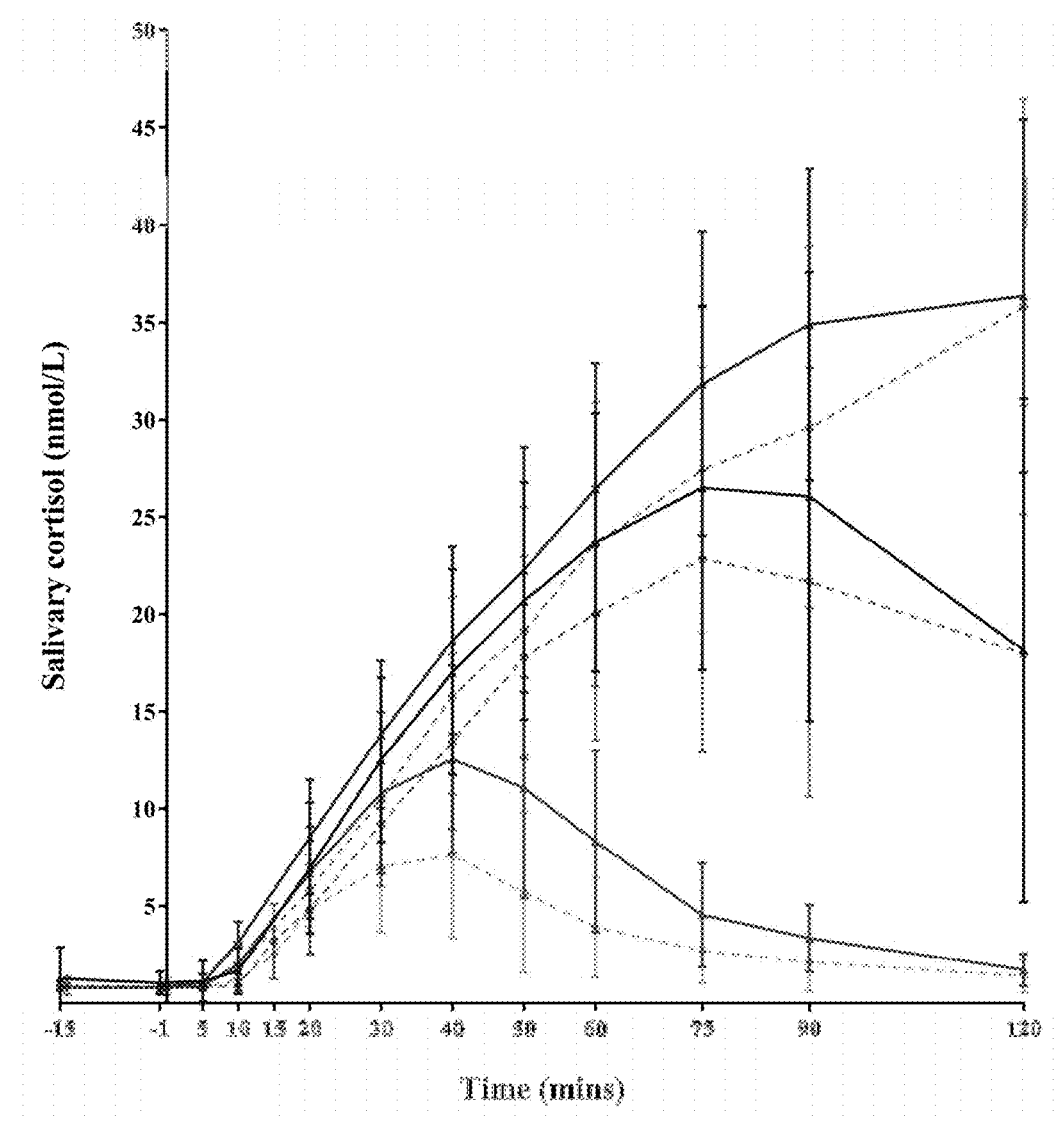
Figure 36C:
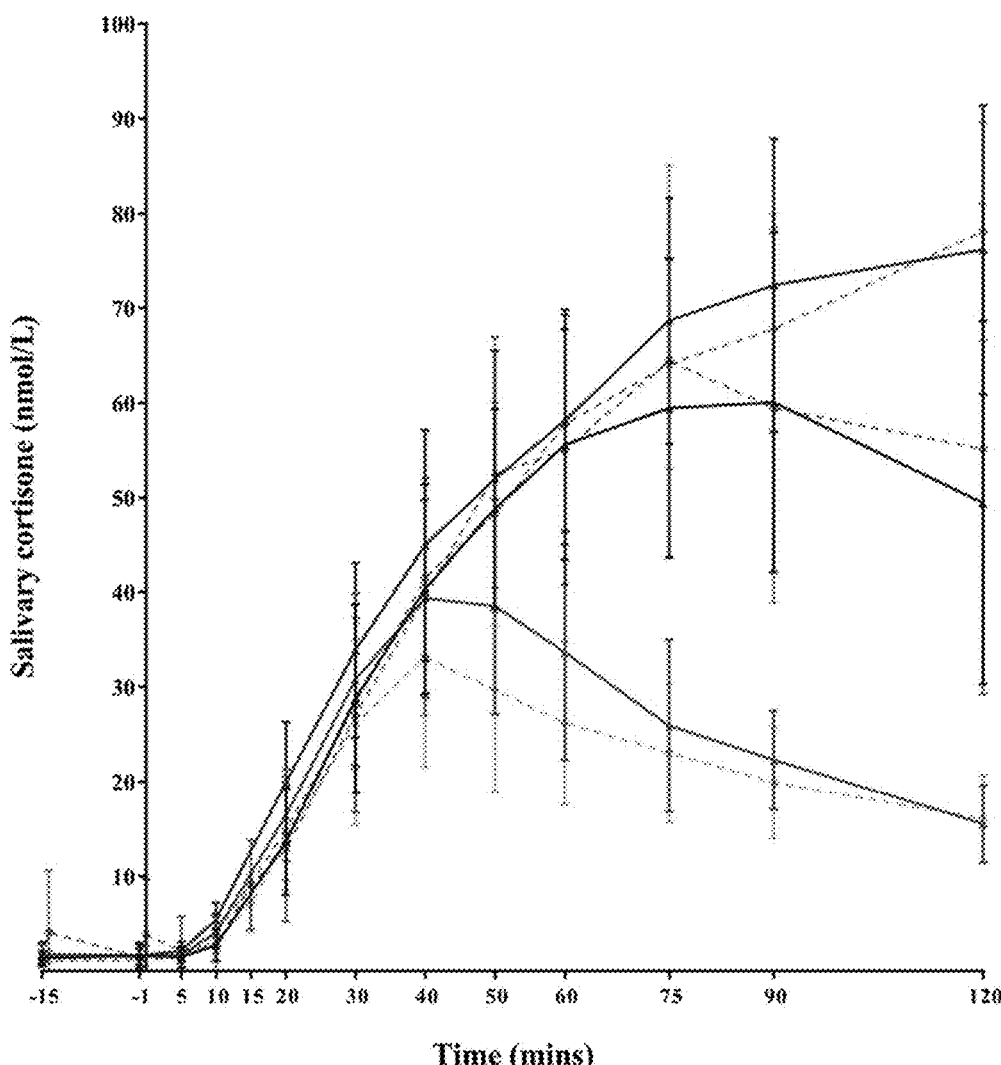

FIGS. 35A-35B Plasma cortisol response, (A-B) Cmax and (C-D) AUC with age for individual paediatric subjects (LHS of each graph) following administration of the 500 mcg Nasacthin dose. The paediatric values are compared against mean±SD adult cortisol values (RHS of each graph). There was a slight age-related trend for higher cortisol response at lower age but overall the cortisol responses with age in the paediatric subjects were in line with those in adults;

FIGS. 36A-36C Glucocorticoid response to 250 mcg IV (top), 1 mcg IV (bottom) and Nasacthin 003 IN (middle) over time, with administration being 0 minutes in dexamethasone-suppressed healthy volunteers. Adult responses are shown in dotted lines and Paediatric responses in solid lines. The glucocorticoid in FIG. 36A is plasma cortisol, in FIG. 36B salivary cortisol and in FIG. 36C salivary cortisone. The figures demonstrate the similarity between the responses in adults and children and between the three glucocorticoids. The also demonstrate there is not difference at 30 minutes in the glucocorticoid response between the doses of tetracosactide and no difference out to 75 minutes between the 250 mcg IV and nasacthin 003.

Figure 37:
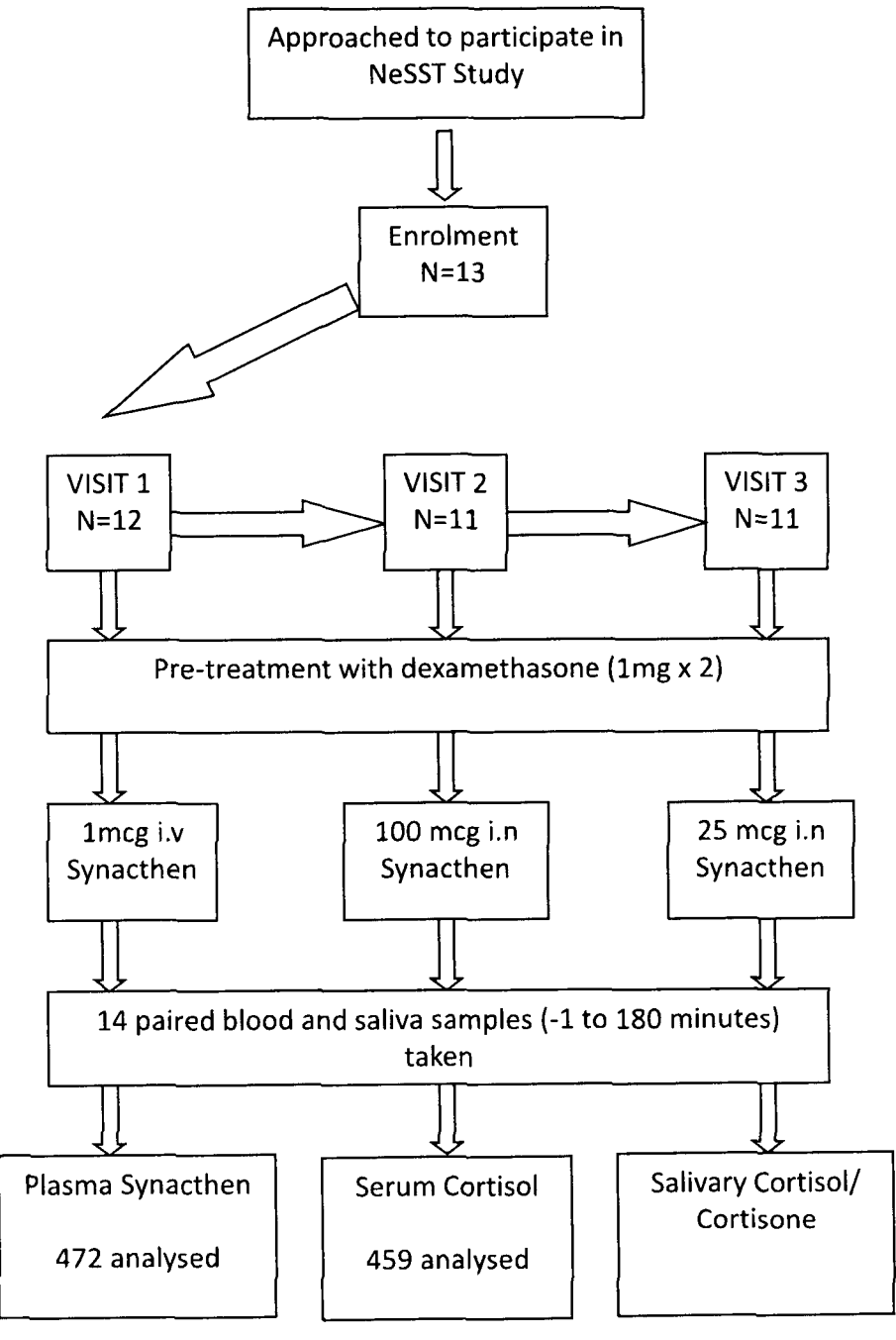

FIG. 37 Recruitment flow chart and volunteer pathway for NeSST study.

Figure 38:
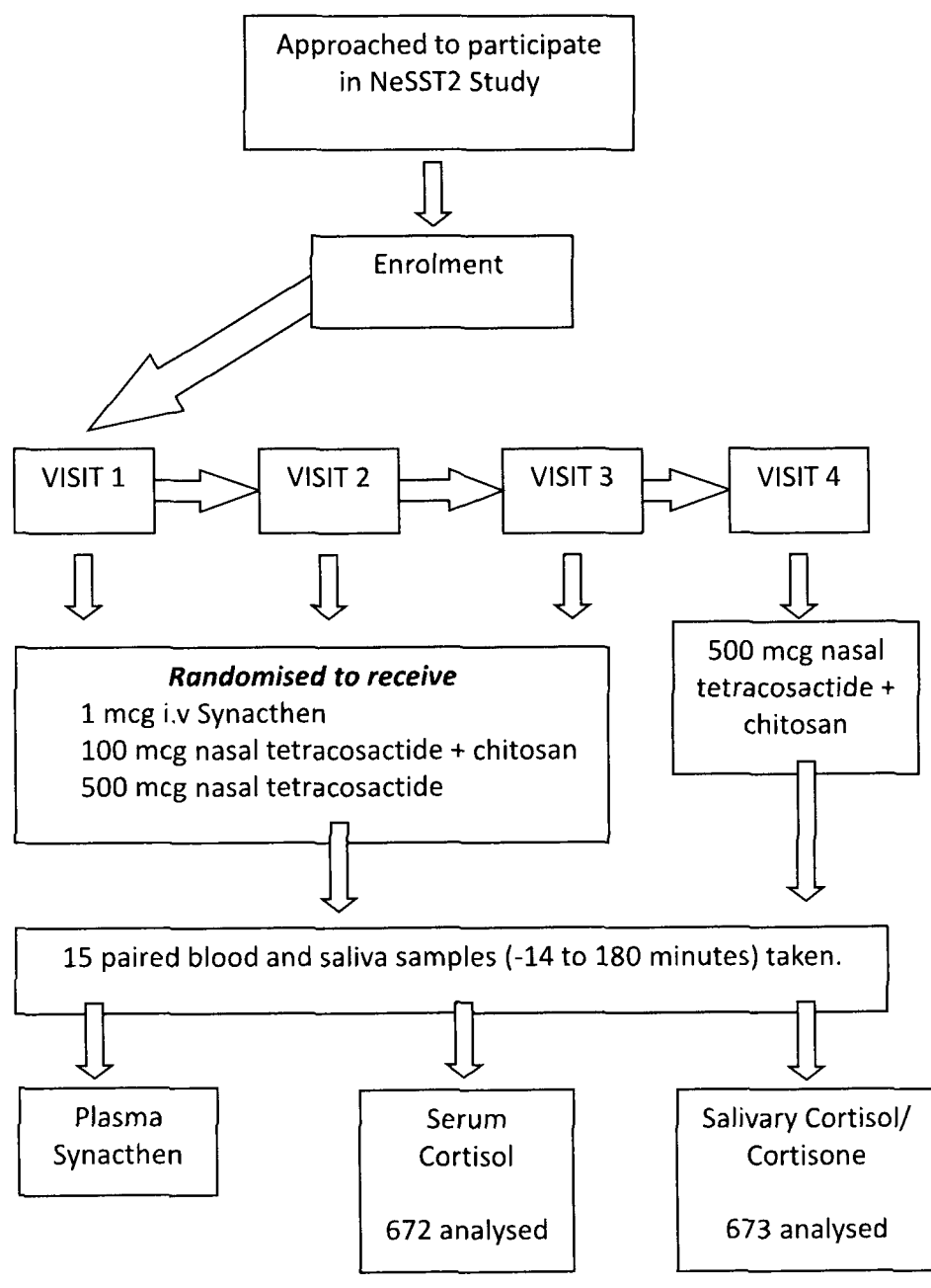

FIG. 38 NeSST2 stage 1a study flow chart.

TABLE 8

Mean plasma Synacthen and serum cortisol at each time point for subjects following 1 mcg IV. 100 mcg IN and 500 mcg IN (no chitosan) (STUDY 1 NeSST). SDs shown in parentheses.

| | 1 mcg i.v visit | | | | 100 mcg i.n visit | |
| | Synacthen pg/ml | | | | Synacthen pg/ml | |
| | | | Minus | Cortisol | | |
| Mins | N = 11 | No S3* N = 10 | baseline N = 11 | nmol/L N = 11 | N = 10 | No S3* N = 9 |
|---|---|---|---|---|---|---|
| −1 | 50.4 (40.4) | 38.6 (0.0) | 0.0 (0.0) | 23.6 (4.1) | 55.6 (47.2) | 41.3 (14.7) |
| 5 | 273.1 (101.8) | 254.0 (215.5) | 222.7 (87.0) | 92.2 (57.2) | 62.0 (45.7) | 48.3 (14.5) |
| 10 | 112.0 (55.4) | 95.9 (57.6) | 61.6 (21.1) | 226.9 (44.5) | 63.9 (53.9) | 47.7 (17.1) |
| 15 | 73.5 (42.8) | 61.2 (22.6) | 23.1 (13.5) | 338.7 (52.0) | 77.5 (59.2) | 63.3 (41.1) |
| 20 | 62.2 (44.8) | 49.1 (10.5) | 11.8 (7.4) | 359.0 (49.3) | 69.1 (47.9) | 56.1 (25.9) |
| 30 | 59.3 (44.5) | 46.4 (7.9) | 9.1 (6.8) | 377.1 (46.9) | 63.1 (48.9) | 49.1 (21.7) |

TABLE 8-continued

Mean plasma Synacthen and serum cortisol at each time point for subjects following 1 mcg
IV. 100 mcg IN and 500 mcg IN (no chitosan) (STUDY 1 NeSST). SDs shown in parentheses.

| 40 | 53.6 (41.7) | 41.5 (3.3) | 3.5 (2.5) | 337.0 (51.5) | 62.7 (48.9) | 48.8 (22.8) |
| 50 | 53.5 (41.0) | 41.5 (3.3) | 3.4 (3.0) | 285.4 (55.7) | 56.4 (53.2) | 39.1 (11.9) |
| 60 | 49.9 (38.8) | 38.6 (1.7) | 1.5 (2.6) | 253.5 (51.4) | 62.9 (58.1) | 45.8 (22.6) |
| 75 | 49.8 (38.2) | 38.5 (1.7) | 1.5 (2.5) | 216.4 (49.7) | 82.7 (110.1) | 48.5 (21.7) |
| 90 | 48.2 (39.8)) | 36.4 (0.9) | 0.8 (1.4) | 186.0 (51.4) | 94.6 (163.7) | 43.2 (17.6) |
| 120 | 50.2 (40.0) | 38.7 (1.5) | 1.4 (2.2) | 142.9 (37.0) | 60.4 (49.9) | 46.4 (24.1) |
| 150 | 47.9 (42.3) | 35.5 (0.3) | 0.6 (1.2) | 108.8 (27.3) | 52.9 (48.9) | 38.1 (14.7) |
| 180 | 46.9 (37.4) | 36.0 (0.6) | 0.5 (1.4) | 81.8 (22.1) | 52.4 (44.9) | 38.7 (12.4) |

| | 100 mcg i.n visit | | 25 mcg i.n visit | | | |
| | Synacthen pg/ml | | Synacthen pg/ml | | | |
| Mins | Minus baseline N = 10 | Cortisol nmol/L N = 10 | N = 10 | No S3* N = 9 | Minus baseline N = 10 | Cortisol nmol/L N = 10 |
|---|---|---|---|---|---|---|
| −1 | 0.0 (0.0) | 32.0 (23.8) | 51.2 (49.1) | 36.0 (10.6) | 0.0 (0.0) | 30.9 (31.6) |
| 5 | 6.4 (4.9) | 32.5 (25.7) | 62.5 (54.5) | 44.7 (11.2) | 7.6 (7.4) | 30.5 (30.0) |
| 10 | 8.6 (7.8) | 56.4 (34.5) | 57.3 (46.9) | 42.9 (10.9) | 6.2 (3.8) | 31.4 (25.2) |
| 15 | 22.0 (28.6) | 102.2 (55.0) | 57.1 (48.3) | 42.2 (11.8) | 6.0 (4.9) | 52.0 (41.6) |
| 20 | 13.5 (12.8) | 142.1 (74.8) | 54.5 (54.1) | 36.7 (10.1) | 4.1 (4.0) | 50.7 (40.7) |
| 30 | 7.5 (9.6) | 150.9 (73.7) | 50.6 (43.5) | 37.3 (12.0) | 2.3 (3.0) | 64.9 (55.9) |
| 40 | 7.1 (10.1) | 128.9 (63.6) | 54.8 (49.0) | 40.1 (16.5) | 5.4 (7.6) | 52.7 (43.0) |
| 50 | 3.1 (3.5) | 109.7 (57.7) | 56.1 (50.1) | 41.1 (17.6) | 7.0 (8.2) | 46.4 (33.1) |
| 60 | 6.0 (9.2) | 94.7 (49.6) | 58.5 (52.2) | 43.4 (22.5) | 9.3 (13.7) | 42.9 (28.3) |
| 75 | 7.4 (8.5) | 78.2 (32.0) | 58.6 (50.8) | 43.9 (21.6) | 9.2 (13.9) | 39.0 (23.9) |
| 90 | 2.7 (3.4) | 66.9 (36.6) | 61.0 (66.7) | 40.8 (21.2) | 12.4 (19.0) | 35.0 (19.6) |
| 120 | 6.3 (10.4) | 52.4 (26.8) | 62.7 (66.5) | 41.1 (16.0) | 11.6 (14.9) | 30.1 (12.9) |
| 150 | 1.4 (2.3) | 42.1 (19.1) | 57.6 (67.8) | 36.6 (13.6) | 10.0 (19.1) | 27.2 (8.7) |
| 180 | 1.0 (1.6) | 33.7 (11.7) | 57.4 (60.2) | 38.7 (11.8) | 8.9 (12.7) | 24.8 (5.2) |

*No S3—data with subject 3 removed (high baseline Synacthen in all three visits)

TABLE 9

Comparison of means, standard deviations (SD), ranges, coefficient of variation (CV) and timing of the
peak for peak plasma Synacthen and serum cortisol values in six different Synacthen tests performed in
STUDY 1 (NeSST) and STUDY 2 (NeSST2 1a). CV expressed in %. Ranges and modes displayed in parentheses.

| Visit | Number of subjects | Mean, SD, range & CV for plasma Synacthen peak in pg/ml | Median with IQR and mode timing of the Synacthen peak in mins | Number of subjects | Mean, SD, range & CV for serum cortisol peak in nmol/L | Median with IQR and mode timing of the cortisol peak in mins |
|---|---|---|---|---|---|---|
| 1 mcg i.v NeSST | 12 | 222.7 ± 87 (103-360.8) 39.1% | 5 ± 0 (5) | 11 | 389.8 ± 51.2 (314-450) 13.1% | 30 ± 10 (30) |
| 1 mcg i.v NeSST2 | 10 | 258.0 ± 102.6 (95.2-393.4) 39.8% | 5 ± 0 (5) | 10 | 392.3 ± 92 (271.8-532.4) 23.5% | 30 ± 0 (30) |
| 100 mcg i.n NeSST | 10 | 55.6 ± 104.4 (6.0-374.0) 187.8% | 20 ± 5 (20) | 10 | 159.6 ± 95 (60.5-318.7) 59.2% | 30 ± 7.5 (30) |
| 100 mcg + chitosan NeSST2 | 11 | 171.7 ± 90.4 (48.4-336.3) 52.6% | 10 ± 7.5 (10) | 11 | 336.1 ± 160.8 (29.1-558.7) 47.8% | 40 ± 20 (50) |
| 500 mcg i.n NeSST2 | 12 | 974.7 ± 780.5 (46.1-1800.2) 80.1% | 10 ± 10 (10) | 12 | 401.6 ± 183 (40-632.1) 45.6% | 50 ± 60 (90) |
| 500 mcg i.n + chitosan NeSST2 | 6 | 1393.6 ± 1498.6 (366.7-4318.7) 107.5% | 12.5 ± 5 (10) | 9 | 645.4 ± 132.7 (503.1-900.6) 20.6% | 75 ± 30 (90) |

TABLE 10

Plasma Synacthen PK data for STUDY 1 NeSST and STUDY 2 NeSST2 1a studies. (All data are median values plus range)

| Dose | NeSST & NeSST2 | NeSST Study | | NeSST2 Study | | |
|---|---|---|---|---|---|---|
| | | | | 100 mcg i.n with | | 500 mcg i.n with |
| | 1 mcg iv | 25 mcg in | 100 mcg in | chitosan | 500 mcg i.n | chitosan |
| Numbers of subjects analysed | 11*$ | 10 | 10 | 8 | 10 | 7 |
| AUC$_{0-\infty}$, (min/pg/ml) | 1442 (691-3082)* 2901 (864-3198)$ | 148.4 (19.6-459) | 341.2 (152.2-1237) | 2916 (1041-20937) | 16191 (1285-47411) | 20371 (7628-68479) |
| Cmax (pg/ml) | 178 (104-361)* 316 (95-395)$^{\&}$ | 10.2 (2.9-18.6) | 14.92 (5.96-97.02) | 170.3 (48.4-1336.8) | 960 (34-2643) | 1287 (366-3519) |
| Tmax (min) | 5 5 | 10 (5-15) | 10 (5-20) | 10 (5-20) | 10 (5-20) | 12.5 (10-20) |
| Bioavailability (F) | | 0.0024 (0.0006-0.027) | 0.00198 (0.0007-0.0179) | 0.007231 (0.0036-0.051) | 0.0125 (0.0008-0.051) | 0.019 (0.0052-0.0475) |
| CL/F (ml/min) | | 139273 (53285-1150431) | 289013 (62774-541017) | 34288 (4765-90657) | 26415 (10543-331929) | 339 (312-1132) |
| Vd/F (ml) | | 1703027 (946475-5385143) | 5584221 (971911-16325569) | 293259 (42167-2142164) | 293198 (130072-12157505) | 3253 (1247-7657) |
| Mean Residence Time (min) | 7.2 (4.2-16.9)* 9.5 (7.0-12.3)$ | 12.2 (8.1-25.7) | 19.7 (13.7-30.2) | 17.02 (9.8-20.0) | 19.79 (11.1-26.1) | 16.69 (9.2-29.4) |
| Elimination half-life (min) | 5.52 (3.0-41.6)* 5.04 (2.5-8.1)$ | 10.68 (2.9-17.7) | 16.39 (4.5-39.1) | 7.53 (3.7-21.7) | 8.66 (5.3-72.9) | 5.32 (3.53-34.3) |

*NeSST Study
$NeSST2 Study

TABLE 11

STUDY 5 (NeSST2 stage 2 Paediatric study). Overall better exposure to 500 mcg in compared to 1 mcg iv. All values GM (95% Cl GM) except Tmax median (range).

| PK Parameter | NeSST Paediatric study | | | |
|---|---|---|---|---|
| | 1 mcg IV | 250 mcg IV | 500 (IN in C | 500 (IN in C |
| AUC$_{0-inf}$ (pg/ml.min) | 7056 (5229-9519) | 77058 (46899-126611) | 20934 (16274-24156) | |
| AUC$_{0-last}$ (pg/ml.min) | 4676 (3043-7185) | 75329 (45537-124611) | 16672 (12845-20192) | |
| Cmax (pg/ml) | 340 (208-555) | 6702 (4346-10335) | 433.3 (324-602) | |
| | | | Based on 1 mcg iv | Based on 250 mcg iv |
| F$_{0-inf}$ | | — | 0.00556 (0.00409-0.00768) | 0.143 (0.05-0.130) |
| F$_{0-last}$ | | — | | |
| CmaxD ratio | | — | | |
| Tmax (min) | | — | 10 (5-20) | |

MATERIAL AND METHODS

Study
  NeSST (study 1)
  N=11; Nasal doses tested: 25 mcg and 100 mcg; IV comparator: 1 mcg
  NeSST2 1a (study 2)
  N=12; Nasal doses tested: 100 mcg+chitosan, 500 mcg, 500 mcg+chitosan; IV comparator: 1 mcg
  NeSST2 1b (study 3)
  N=12; Nasal doses tested: 500 mcg+chitosan, 1 mg+chitosan; IV comparator: 250 mcg
  NeSST2 1c (study 4)

N=6 (recruited from study 3, NeSST2 1b); 2 further 500 mcg+chitosan IN visits. No IV comparator—repeatability study.
All used healthy adult, male volunteers.
NeSST2 2 (study 5)
N=24 healthy children aged 4-14 recruited, equal sex distribution
All 24 received 500 mcg+chitosan
IV comparator randomised—12 received 1 mcg and 12 250 mcg
Volunteers were their own controls receiving the nasal doses and an IV comparator at separate visits, at least a week apart (fortnight in study 1).

The materials and methods below are from NeSST ($1^{st}$ study). I have indicated when differences between the studies are relevant.

Study Design

These were four pharmacokinetic (PK) studies as described above (studies 1-3 & 5). All were open-label. A crossover design was used, such that the same individual received the IV comparator and IN formulations. STUDY 4 was a repeatability PK study and therefore no IV comparator was used. The crossover design, where between occasion variables are minimized (e.g. fasting or fed conditions, time of day, concomitant medication), is the recommended methodology for generating bioequivalence data (European Medicines Agency 2010). The study design was based on that recommended for bioequivalence studies, although this was a bioavailability study. It was considered unnecessary to demonstrate that the two formulations (i.v and i.n) have the same (bioequivalence) but instead show that an adequate amount of Synacthen is absorbed to produce equivalence in the resultant cortisol response (FIGS. 37 and 38).

In keeping with pharmacokinetic trials of this kind the subjects were neither randomized nor blinded and did not receive a placebo. Studies 1, 2, 3+5 were conducted from Sheffield Children's NHS Foundation Trust (SCH), Sheffield, UK and studies 3+4 from Sheffield Teaching Hospitals NHS Trust, Sheffield, UK.

Subjects

The participants for studies 1-4 were healthy, male volunteers between the ages 19-44. The healthy children in study 5 were aged between 4-14 years. European Medicines Agency (EMA) guidelines were followed and only adult, male volunteers were enrolled in the initial studies due to the possible adverse effects of the drug on a fetus or child and to reduce variability not attributable to the difference between routes of administration. EMA guidance states that "this model, in vivo healthy volunteers, is regarded as adequate in most instances to detect formulation differences and to allow extrapolation of the results to populations for which the reference medicinal product is approved (the elderly, children, patients with renal or liver impairment, etc.)".

Number of Subjects

European Medicines Agency guidance was followed and 12 subjects were selected as the minimum number for a bioavailability study.

Inclusion Criteria

1. Aged between 18 and 64 years of age (in study 5—children aged 2-15)
2. Male (in study 5—children of both sexes)
3. Body Mass Index (BMI) between 18.5 and 30 kg/m$^2$
4. Healthy (see exclusion criteria)
5. Non-smoker Exclusion Criteria 1. Past or present history of an endocrinopathy
2. Past or present history of asthma
3. Past or present history of allergic rhinitis
4. Past or present history of peptic ulcer disease/gastro-intestinal bleed/significant dyspepsia
5. Past history of intra-cranial or renal/adrenal pathology
6. Presently on any medication
7. Presently, or within the last 3 months, been prescribed any type of corticosteroid (oral, inhaled, nasal, rectal, i.v, i.m, intra-articular, intra-ocular, topical)
8. Ever been prescribed a prolonged course of oral corticosteroids (more than 1 month)
9. Previous adverse reaction (including mild hypersensitivity) to ACTH or Synacthen 10. Previous severe allergic reaction or anaphylaxis
11. Coryzal symptoms within the last week* (and will be asked to report any new symptoms occurring within 24 hours of the test)

* Not exclusion criteria, if met all other criteria and had coryzal symptoms visit was delayed until a week after resolution of the symptoms.

12. Currently anaemic

Subject Data

Basic demographic data was collected on all volunteers at visit one. This included age and ethnic group. Volunteers had their height and weight measured. This allowed calculation of body mass index (BMI) and body surface area (BSA) to enable volume of distribution calculations for Synacthen.

At each visit subjects were asked to report coryzal symptoms beginning within 24 hours of the test (which may impact on nasal absorption due to changes in the mucosa) and this was additionally checked on all subsequent visits.

Paired samples of blood and saliva were taken throughout each visit. These were analysed for plasma Synacthen and serum cortisol and salivary cortisol and cortisone levels.

Subject Visits

Following recruitment, subjects were asked to attend the Children's Clinical Research Facility (CCRF) at SCH or RHH for their visits, each separated by a minimum of a week (fortnight in study 1). This allows for a sufficient washout period between administrations, at least 5-half lives of the drug.

Prior to each visit volunteers were asked to abstain from alcohol and recreational drugs for 24 hours and to take 1 mg of dexamethasone on retiring the night before the visit and a second 1 mg dose after breakfast on the morning of the visit (0.5 mg if child younger than 8 years). There are no commercially available Synacthen assays, or any for research purposes, and therefore it was necessary to temporarily suppress the volunteers' endogenous production of ACTH to enable use of an ACTH assay, with the inference that anything detected was Synacthen.

Each visit commenced between 08.30 and 09.30. Volunteers were not required to fast. An i.v cannula was sited and the volunteer was asked to rest, lying down, for 30 minutes to recover from the physiological stress of cannulation. Ten-fifteen minutes before the first samples were taken the subject was asked to rinse their mouth thoroughly with water to minimise contamination that may compromise salivary cortisol assay performance. Additionally it was requested that they refrain from eating or drinking, other than water, during the visit. The volunteers were asked to remain supine for the duration of the test.

Synacthen Administration

Nasal Synacthen was administered by atomiser syringe (Mucosal Atomizer Device™, Wolfe Tory Medical Inc. Utah, USA). The Mucosal Atomizer Device™ (MAD) atomises liquids to 30-100 microns allowing rapid absorption into the bloodstream.

Between 0.1-0.2 mls were given up each nostril per administration:

25 mcg-0.1 ml to a single nostril
100 mcg-0.2 ml to each nostril
100 mcg plus chitosan-0.1 ml to each nostril
500 mcg-0.1 ml to each nostril
500 mcg plus chitosan-0.1 ml to each nostril
1 mg-0.2 ml to each nostril Tetracosactide Nasal Solution (TNS) (Investigative Medicinal Product Nasacthen 001, 002 and 003

The pharmacokinetic, metabolic, toxicological and clinical properties of tetracosactide following i.v injection are well known and are described in the Summary of Product Characteristics. Tetracosactide nasal solution (TNS) has the same active pharmaceutical ingredient but with the addition of an excipient, chitosan, to aid absorption when administered nasally.

Pharmacokinetic extrapolation using NeSST Study (study 1) AUC data estimated that 500 mcg of intranasal Synacthen would be required to give an equivalent response to the 1 mcg i.v LDSST. TNS is an aqueous solution containing either 0.5 mg/ml (providing 50 mcg tetracosactide) or 2.5 mg/ml (containing 250 mcg of tetracosactide) in the form of the acetate salt. In order to deliver 100 mcg and 500 mcg one spray (of 0.1 ml) per nostril (0.2 ml in total) was required. Two TNS solutions also contained chitosan glutamate (a cationic biopolymer which acts as a mucoadhesive/bioadhesive agent. In addition, the three TNS solutions contained sodium chloride for tonicity adjustment, benzalkonium chloride as a preservative, and acetic acid and sodium acetate as a buffer to adjust/maintain pH (Table 3).

Tetracosactide is used as the acetate salt form in the existing injection product. This salt form is reported to be sparingly soluble in water (approximately 10-30 mg/ml), however this solubility is sufficient to provide a solution suitable for intranasal administration. Two of the three TNS formulations contained chitosan (in the glutamate salt form). A chitosan glutamate concentration of 5 mg/ml was selected for the TNS formulations.

TABLE 3

Composition of each 0.5 ml vial of Tetracosactide Nasal Solution.

| | | Quantity per 0.5 ml | | |
| | | TNS Nasacthen 001 0.5 mg/ml + chitosan | TNS Nasacthen 002 2.5 mg/ml | TNS Nasacthen 003 2.5 mg/ml + chitosan |
| Component | Function | | | |
| --- | --- | --- | --- | --- |
| Tetracosactide acetate | Active | 0.25 mg | 1.25 mg | 1.25 mg |
| Chitosan glutamate | Bioadhesive | 2.5 mg | — | 2.5 mg |
| Sodium chloride | Osmolality adjustment | 2.7 mg | 2.7 mg | 2.7 mg |
| Benzalkonium chloride | Preservative | 0.075 mg | 0.075 mg | 0.075 mg |
| Acetic acid | pH adjustment | 2.55 mg | 2.55 mg | 2.55 mg |
| Sodium acetate trihydrate | pH adjustment | 1.05 mg | 1.05 mg | 1.05 mg |
| Water for injections | Vehicle | To 0.5 ml | To 0.5 ml | To 0.5 ml |

Physicochemical Characteristics for Tetracosactide Drug Compound

| | |
| --- | --- |
| Molecular formula | $C_{136}H_{210}N_{40}O_{31}S$ (net) |
| Molecular mass | 2933.5 g/mol |
| Salt form | Acetate salt (between 4 and 8 moles of acetic acid may be present per mole of peptide) |
| Physical form | White to yellow powder |
| Polymorphism | Amorphous powder, as tetracosactide is isolated by lyophilisation. No crystalline or polymorphic forms are known. |
| Appearance of solution | Clear and colourless (1 mg/mL in water) |

Physiochemical Characteristics of the Chitosan Used in the NeSST2 Study

Generic name: Chitosan glutamate

Chemical name: ß-(1→4)-linked 2-acetamido-2-dexoy-D-glucopyranose and 2-amino-2-deoxy-D-glucopyranose glutamate; ß-(1→4)-linked N-acetyl-D-glucosamine and D-glucosamine glutamate Manufacturers name: PROTOSAN™ UP G 213

CAS registry: 84563-76-8

Molecular weight: The molecular weight (g/mol) of the monomer unit is 161 for D-glucosamine and 203 for N-acetyl-D-glucosamine. Glutamate has a molecular weight of 146. Typically, the molecular weight for PROTASAN UP G 213 is in the range 200000-600000 g/mol.

Description: PROTASAN UP G 213 is a white or off-white powder that forms a clear, colourless to slightly yellowish solution when dissolved in water. The solution may become thick, i.e. viscous depending upon the concentration of PROTASAN UP G 213 used.

pH of aqueous solution: The pH of an aqueous solution (1%) of PROTASAN UP G 213 is between 4 and 6.

Solubility of PROTASAN UP G 213 is a function of the Solubility: concentration (g/l or mg/ml), ionic strength of the solution and the presence of buffering ions.

Chitosan Safety

Chitosan glutamate has been tested for safety and toxicity in a number of animal species using different routes of administration. The preclinical data augment the considerable clinical data on intranasal chitosan in both human volunteers and patients. Nasal formulations containing chitosan, both in the form of solutions containing 5 mg/ml chitosan as well as powders, have been administered to over 1000 people in clinical trials and in excess of 2900 doses have been administered. Collectively no safety or tolerability issues were identified in any study and these data do not identify any specific hazard that would preclude the use of chitosan in further clinical trials (personal communication, Peter Watts, Phormulate Consulting Ltd).

Blood and Saliva Sampling

Paired blood and saliva samples were taken at:

Study 1: −1, 5, 10, 15, 20, 30, 40, 50, 60, 75, 90, 120, 150 and 180 minutes (where Synacthen administration was 0 minutes).

Study 2: −15, −1, 5, 10, 15, 20, 30, 40, 50, 60, 75, 90, 120, 150 and 180 minutes Study 3: −15, −1, 2, 5, 10, 20, 30, 40, 50, 60, 75, 90, 120, minutes Study 4: −15, 5, 10, 30, 40, 60, 90 minutes Study 5: −15, −1, 2, 5, 10, 20, 30, 40, 50, 60, 75, 90, 120, minutes Saliva was obtained by passive drool technique, with 1 ml, dribbled down a straw into a salicap container.

Plasma Synacthen Analysis

Studies 1+2: Analysed by ACTH radioimmunoassay with Synacthen standards

Study 3, 4+5: Synacthen EIA.

Serum Cortisol

Abbott Architect chemiluminescent microparticle immunoassay method. Abbott Diagnostics quoted functional sensitivity (with applied 95% confidence interval) as 28 nmol/L, a linear range of 28-1650 nmol/L, and <10% total CV for serum samples in the ≥83 to ≤966 nmol/l range. Quoted limit of detection (LoD) is 22 nmol/L; typical daily Quality Control precision (CV) at the Sheffield Children's Hospital was 2-3% at 100, 500 and 800 nmol/l levels. Quoted cross-reactivity with dexamethasone was 0.0%.

Salivary Cortisol and Cortisone

CORTISOL: Liquid chromatography-tandem mass spectrometry (LC-MS/MS) was used. Derived assay characteristics showed the assay to be linear up to 3393 nmol/L, with lower limits of quantitation of 0.75 nmol/L and intra- and inter assay imprecision of <8.9% over three levels of internal QC, with recovery and accuracy within acceptable limits. Additionally interference studies demonstrated high specificity. The cortisol assay was unaffected by the presence of dexamethasone.

CORTISONE: LC-MS/MS Derived assay characteristics showed the assay to be linear up to 3676 nmol/L, with lower limits of quantitation of 0.50 nmol/L and intra- and inter assay imprecision of <6.5% over three levels of internal QC, with recovery and accuracy within acceptable limits. The cortisone assay was unaffected by the presence of dexamethasone.

Statistical Analysis

The aim of the study was to determine the bioavailability of intranasal Synacthen and ascertain if equivalence (for the purposes of an adrenal suppression test) is possible via the nasal route.

The analysis was performed using WinNonLin 6.1 (Pharsight, Missouri, USA). This is the industry standard for PK, pharmacodynamic (PD) and non-compartmental analysis.

Pharmacokinetic Data Preparation

Prior to analysis the concentration-time data for i.v and nasal Synacthen were visually inspected by plotting the individual profiles in Microsoft® Excel. Any baselines effects (from endogenous substances i.e. ACTH or an interfering substrate detected in the assay) should be removed from the PK profile prior to analysis and thus the −1 minute Synacthen values were subtracted from all concentration time points. If necessary the values were fixed after the concentration fell to zero, as PK analysis cannot compute negative numbers. All plasma concentrations reported as missing or below the lower limit of quantification were excluded from the analysis. Data was then arranged (subject, time, concentration, dose and route) for import into the pharmacokinetic (PK) software Phoenix WinNonLin 6.1.

Pharmacokinetic Data Analysis

The standard PK parameters for bioavailability, time to maximum plasma concentration (Tmax), maximum plasma concentration (Cmax), area under the concentration time curve from time zero until the last quantifiable time point ($AUC_{0-t}$), area under the concentration time curve from time zero until infinity ($AUC_{0-\infty}$) and terminal half-life (terminal t½) were calculated for each individual using standard methods within the Phoenix WinNonLin 6.1 non compartmental analysis software. For calculating the terminal t½ a minimum of three of the last data points were used.

Bioavailability of the i.n formulation to the i.v formulation were assessed on the basis of Cmax and $AUC_{0-t}$ ($AUC_{0-\infty}$ was not used as the Synacthen was eliminated very rapidly with plasma concentrations being virtually zero by time t).

The concentration-response data in terms of the Cmax for the Synacthen and cortisol data was collated manually in Microsoft® Excel. The concentration-response data were analysed using a number of known models (Emax, sigmoidal Emax, linear and power function), models were fitted using non-linear regression. Weighted residuals were calculated to determine the difference between the observed and model predicted cortisol values at each Synacthen concentration, these were weighted based on the concentration of Synacthen to allow for potential analytical errors. The sum of the squares of the weighted residual values was calculated and the solver function in Excel used to fit model parameters to minimise this value. The best-fit model was determined using the Akaike information criteria.

Non-PK Data Analysis

In addition to the pharmacokinetic modelling mean cortisol and Synacthen at the various time points were compared by paired t-tests with a Bonferroni correction applied. The timing of the peak cortisol response, the dose-response relationship between nasal Synacthen and cortisol production and the inter-individual variability of nasal Synacthen have all been deduced.

EXAMPLE 1

The mean plasma Synacthen responses to the four different doses of Synacthen are heightened both by the increase in dose and the addition of chitosan (FIGS. 3, 4, 7). The resultant cortisol response was similarly affected by both dose and the addition of chitosan (FIGS. 3, 5, 6). The peak in plasma Synacthen following administration with 1 mcg i.v Synacthen is much lower compared with the nasal formulations however the cortisol peak is similar to those seen following 100 mcg with chitosan and 500 mcg nasal Synacthen and much greater with 500 mcg with chitosan (FIGS. 3+4).

EXAMPLE 2

The two 1 mcg i.v tests produced broadly similar plasma Synacthen responses, both with a suppressed cortisol response. Considerable variability in plasma Synacthen levels with all formulations and serum cortisol response following nasal administration are demonstrated by the large ranges and SDs and can be seen by the large error bars (FIGS. 1, 2, 4, 5). The calculation of CVs gives a measure of variability and is considerably smaller for the i.v dose than the nasal formulations. When chitosan is added to 100 mcg tetracosactide it reduces the variability of peak plasma Synacthen values (CV falls from 187.8% to 52.6%) however with the 500 mcg tetracosactide dose the addition of chitosan appears to worsen variability (80.1% to 107.5%). The addition of chitosan reduced the variability of peak serum cortisol at both doses (100 mcg 59.2% to 47.8% and 500 mcg from 45.6% to 20.6%). The timing of the cortisol peak is seen to vary more after nasal Synacthen than following i.v administration (table 9).

In study 4 six volunteers received the same dose of nasal Synacthen on two occasions, in addition to the administration with the same dose/formulation in study 3 (although this had been with an unprimed mucosal atomiser device so a lower and potentially more variable dose). There was no difference between all three visits for Synacthen Cmax, plasma cortisol Cmax and $AUC_{0-t}$, salivary cortisone Cmax and $AUC_{0-t}$. There was a difference between visits for Synacthen $AUC_{0-t}$ and $AUC_{0-inf}$. The difference was due to visit 1, where a slightly lower dose was given due to MAD lack of priming—there was no statistical difference between visits 2 and 3. (FIGS. 22, 23, 24+25 and 26-29).

The cortisol response to the higher dose of nasal Synacthen given in the first NeSST Study (study 1) (100 mcg), the combined mean of the two 1 mcg i.v tests from both studies and the three nasal doses from the NeSST2 Study are included for a visual comparison of the effect of increase dose and addition of a nasal drug enhancer (FIG. 6).

The median absolute bioavailability of the 100 mcg with chitosan intranasal dose was approximately 0.72% (range 0.36 to 5.1%) of the 1 mcg i.v dose. The bioavailability with 500 mcg tetracosactide showed the greatest variability, 1.25% (0.08-5.1%) and the highest bioavailability was achieved with the 500 mcg tetracosactide and chitosan formulation, 1.9% (0.52-4.8%). The time to maximum concentration (Tmax) was longer for intranasal formulations, 10-12.5 minutes, compared with five minutes following i.v administration and was longest with the 500 mcg tetracosactide and chitosan preparation (12.5 compared to 10 minutes). The maximum concentration (Cmax) was approximately 53.9% following 100 mcg with chitosan, 303.8% after 500 mcg tetracosactide and 407.3% following 500 mcg tetracosactide with chitosan, much greater than those seen with the nasal doses given in the NeSST Study (study 1). Table 10.

The bioavailability of the 100 mcg Synacthen intranasal dose increased by 3.65-fold following formulation with chitosan, although the populations were not the same as the results are combined from the NeSST and NeSST2 studies. The bioavailability of the 500 mcg intranasal dose was higher than anticipated without the addition of chitosan and the addition of the nasal enhancer only increased the bioavailability by 1.5-fold. Table 10.

Mean residence time (MRT) measures the time that molecules of Synacthen remain in the body after injection/nasal ingestion to elimination and therefore, as one would expect, the MRT was longer for the nasal formulations than for the i.v preparation. At both 100 and 500 mcg the MRT was reduced following the addition of chitosan, but dose escalation appeared not to influence it. Similarly the elimination (or terminal) half-life of plasma Synacthen was shorter following the addition of chitosan to both the 100 and 500 mcg doses. It was almost the same for the i.v and 500 mcg tetracosactide with chitosan formulations. Despite a shorter half-life, the cortisol response appeared more prolonged with the higher nasal doses. Table 10.

Following both the 100 mcg tetracosactide with chitosan and the 500 mcg tetracosactide doses individuals showed a similar cortisol response to the 1 mcg i.v test but consistency was lacking. As expected there was more variability in the data following intranasal administration compared with i.v. Table 9.

EXAMPLE 3

IV 250 Mcg Test (N=12)

Plasma cortisol rose 5 minutes after Synacthen administration (FIG. 8a). Plasma cortisol Tmax was at 120 minutes for all participants. The IV 250 mcg SST was the least variable, with standard deviations ranging from ±31.94-53.04 nmol/l for time-points.

Mean plasma cortisol concentration:
30 minutes: 406.8 nmol/l (±44.33, range 349-477),
60 minutes: 510.5 nmol/l (±49.15, range 433-581).

IN 500 Mcg Test (N=12)

Cortisol levels increased 10 minutes after intranasal Synacthen administration, later than in the IV test (FIG. 8c). Mean peak cortisol was lower in the lower dose IN test than the IV test, at 537.3 nmol/l (±77.65).

Plasma cortisol results for IN 500 mcg were more variable than the IV test, as shown by higher standard deviations, except at 30 minutes post Synacthen. Results were nearly three times as spread at 90 and 120 minutes, although the lower mean concentration and varying Cmax and Tmax of the IN 500 mcg test should be taken into account.

Mean plasma cortisol concentration:
30 minutes: 383.2 nmol/l (±39.28, range 314-449),
60 minutes: 486 nmol/l (±58.62, range 414-567).

IN 1 mg Test (N=12)

Participants showed a rise from baseline after 10 minutes (FIG. 8b). Unfortunately, two participants had a cannula failure midway through the test and so blood results were missed from samples beyond 50 and 60 minutes. Standard deviation, and thus variability, was higher in the IN 1 mg test than the IV test and similar to the IN 500 mcg test.

Mean cortisol concentration:
30 minutes: 380 nmol/l (±49.41, range 317-487),
60 minutes: 488.2 nmol/l (±62.7, range 415-602).

Plasma Cortisol Cmax and Tmax

The IV 250 mcg test showed the highest mean Cmax, at 615.2 (±53.04) nmol/l, ranging from 519-712 nmol/l.

Unpaired t-tests compared the mean Cmax of each nasal test against the IV test. There was a statistically significant difference between the mean Cmax in the IN 500 mcg test (−77.9 nmol/l (p=0.009, CI −21.6 to −134.2 nmol/l).

In the IN 500 mcg test, Tmax was more variable: the majority reached Cmax at 60 or 120 minutes, but one participant was as early as 44 minutes. An unpaired t-test compared Cmax results against early Tmax (≤75 minutes (N=7)) and late Tmax (≥90 minutes (N=4)). There was a statistically significant difference in Cmax for the early Tmaxs (−121.6 nmol/l (p=0.004, CI −191.7 to −51.5 nmol/l)) showing that those who peak early get lower peak concentrations. The mean $C_{max}$ of the IN 1 mg test was in between the two other tests at 586.9 nmol/l (+84), the difference between this test and the IV was not statistically significant (−28.3 nmol/l (p=0.34, CI 33 to −89 nmol/l)). Tmax was at 120 minutes by the majority of participants (N=8) and ≤90 minutes by the rest (N=2). The mean difference was statistically significant (early: −152 nmol/l (p=0.01, CI −256.8 to −48.2) (Table 4).

TABLE 4

| | Individuals' plasma cortisol Cmax and Tmax for each test Individual Peak Plasma Cortisol (Cmax) and corresponding time (Tmax) per test | | | | | |
|---|---|---|---|---|---|---|
| | IV 250 mcg | | IN 500 mcg | | IN 1 mg | |
| ID | Cmax (nmol/l) | Tmax (minutes) | Cmax (nmol/l) | Tmax (minutes) | Cmax (nmol/l) | Tmax (minutes) |
| 01 | 711.8 | 120 | 651.2 | 90 | 736.4 | 120 |
| 02 | 627.3 | 120 | 509.7 | 60 | 603.9 | 120 |
| 03 | 612.3 | 120 | 443.2 | 50 | 677.8 | 120 |
| 04 | 617.6 | 120 | 545.1 | 75 | 611.5 | 120 |
| 05 | 643.7 | 120 | 599.6 | 90 | — | — |
| 06 | 611.6 | 120 | 634.3 | 120 | 580.3 | 120 |
| 07 | 553.8 | 120 | 429.5 | 60 | 453.9 | 76 |
| 08 | 658.3 | 120 | 545.1 | 60 | — | — |
| 09 | 588.3 | 120 | 614.6* | 120* | 603.9 | 120 |
| 10 | 669.2 | 120 | 497.9 | 75 | 578.6 | 120 |
| 11 | 519.4 | 120 | 431.9 | 44 | 476.1 | 90 |
| 12 | 568.7 | 120 | 545.8 | 120 | 546.5 | 120 |
| Mean | 615.2 | — | 537.3 | — | 586.9 | — |
| SD | 53.04 | — | 77.65 | — | 84 | — |

*Excluded from analysis due to high basal levels

EXAMPLE 4

Relationship Between Serum Cortisol, Salivary Cortisol and Salivary Cortisone.

The relational analysis of the NeSST Study (study 1) salivary samples, both to each other and the paired serum sample revealed a correlation, but not as tight as had been anticipated. The data from the NeSST2 Study (study 2) (FIGS. 13, 14, 15) and study 3 (NeSST2 1b) (FIGS. 19, 20, 21) were analysed in the same way. The NeSST Study and NeSST2 Study data were combined to give approximately 1150 paired samples. Tighter relationships than previously were seen between serum and salivary cortisol, salivary cortisol and cortisone and serum cortisol and salivary cortisone. A clear exponential, or biphasic response is seen between salivary and serum cortisol. A tight linear relationship between salivary cortisol and cortisone is observed and between serum cortisol and salivary cortisone.

EXAMPLE 5

The relationship between the timing of the serum cortisol peak and the peaks in salivary cortisol and cortisone following administration with 500 mcg tetracosactide and chitosan were examined in a number of ways to determine recommended sampling times (Table 5).

TABLE 5

Times of peak serum cortisol, salivary cortisol and salivary cortisone following nasal administration with 500 mcg tetracosactide and chitosan (N = 9) (STUDY 2). Mode and median, with interquartile ranges (IQR) have been calculated and are displayed in red.

| | Peak cortisol/cortisone times in minutes | | |
|---|---|---|---|
| | Serum cortisol | Salivary cortisol | Salivary cortisone |
| Subject 1 | 75 | 75 | 75 |
| Subject 2 | 40 | 50 | 60 |
| Subject 3 | 75 | 75 | 75 |
| Subject 4 | 60 | 75 | 60 |
| Subject 5 | 90 | 120 | 120 |
| Subject 6 | 90 | 90 | 90 |
| Subject 7 | 90 | 90 | 90 |
| Subject 8 | 60 | 75 | 75 |
| Subject 9 | 90 | 90 | 120 |
| Mode | 90 | 75 | 75 |
| Median (IQR) | 75 (30) | 75 (15) | 75 (15) |

When viewing the graph of mean cortisol response to 500 mcg tetracosactide and chitosan the peak times for peak salivary cortisol and cortisone appear to occur slightly later, at 75 minutes, compared to the 60 minute peak seen when measuring the response in serum. However the modal peak time occurs at 90 minutes when measuring serum cortisol and earlier at 75 minutes for the salivary markers, but at 75 minutes for all markers when the median is used; (FIG. 16).

EXAMPLE 6

Assessment of correlation between salivary cortisol and cortisone identified a strong positive correlation (Pearson's r=0.95, p<0.0001; (FIG. 19), $R^2$ 0.87 (FIG. 14).

EXAMPLE 7

Assessment of correlation between serum and salivary cortisol identified a strong positive correlation (Pearson's r=0.85, p<0.0001); (FIG. 20).

EXAMPLE 8

Pearson's correlation coefficient identified a strong positive association between plasma cortisol and salivary cortisone (r=0.90, p<0.0001), which was stronger than the correlation found between plasma cortisol and salivary cortisol (FIG. 21).

EXAMPLE 9

As shown in table 6 and 7 the bioavailability of 500 mcg IN is approximately 2-fold higher that 1000 mcg based on AUC0-inf. 1.5-fold higher is based on AUC0-Last.

TABLE 6

PK summary for STUDY 3 (NeSST2 1b)

| PK Metric | Stat | 250 mcg IV | 1000 mcg IN | 500 mcg IN |
|---|---|---|---|---|
| $AUC_{0\text{-}inf}$ | GM (pg/ml.min) | 105069 | 22253 | 23120 |
| | GM Cl | 67256-164141 | 19989-28445 | 15247-35057 |
| | Fold (Max:min) | 11.73 | 3.68 | 6.97 |
| $AUC_{0\text{-}Last}$ | GM (pg/ml.min) | 95441 | 16575 | 11906 |
| | GM Cl | 58189-156542 | 13241-20749 | 9044-15674 |
| | Fold (Max:min) | 19.1 | 3.69 | 5.55 |
| $C_{max}$ | GM (pg/ml) | 11888 | 618 | 319.8 |
| | GM Cl | 6256-22591 | 502-760 | 256-399 |
| | Fold (Max:min) | 28.8 | 3.12 | 4.38 |

TABLE 7

Bioavailability of IN doses (STUDY 3, NeSST2 1b):

| PK Metric | Stat | 1000 mcg IN | 500 mcg IN |
|---|---|---|---|
| $F_{0\text{-}inf}$ | GM | 0.053 | 0.11 |
| | GM Cl | 0.032-0.087 | 0.056-0.217 |
| | Fold (Max:min) | 12.83 | 58.53 |
| $F_{0\text{-}Last}$ | GM | 0.043 | 0.062 |
| | GM Cl | 0.026-0.071 | 0.033-0.117 |
| | Fold (Max:min) | 12.3 | 55.5 |
| $C_{max}$ ratio | GM | 0.013 | 0.013 |
| | GM Cl | 0.0073-0.023 | 0.0065-0.02765 |
| | Fold (Max:min) | 34.92 | 92.65 |

EXAMPLE 10

FIG. 1 shows the mean rise of plasma Synacthen from baseline in subjects following administration with different amounts of i.n Synacthen, FIG. 2 depicts the mean rise of serum cortisol from a suppressed baseline in subjects following administration with different amounts of i.n Synacthen. As shown in the FIGS. 1 and 2 cortisol response is very minimal after i.n. administration of synachten, supporting the use of chitosan to improve cortisol response. See also table 8.

The invention claimed is:

1. A method of diagnosing adrenal insufficiency in a paediatric subject, comprising:
   i) obtaining a sample of saliva from the paediatric subject and measuring cortisone concentration in said saliva sample;
   ii) intranasally administering a pharmaceutical composition to the paediatric subject at a dose of between 500-1000 μg, the composition comprising:
   tetracosactide acetate 0.25% (w/v);
   chitosan glutamate 0.5% (w/v);
   sodium chloride 0.54% (w/v);
   benzalkonium chloride 0.015% (w/v);
   acetic acid 0.51% (w/v); and
   sodium acetate trihydrate 0.21% (w/v); and
   iii) repeating step i) 120 minutes or 180 minutes after the intranasal administration of step ii).

2. The method of claim 1, further comprising:
   iv) comparing the concentration of cortisone in the saliva sample of step (i) with the cortisone concentration of step (iii); and
   v) determining if the paediatric subject has adrenal insufficiency.

3. The method of claim 1, wherein the pharmaceutical composition is administered to the paediatric subject at an effective dose selected from the group consisting of 500, 550, 600, 650, 700, 750, 800, 850, 900, 950, and 1000 μg tetracosactide acetate.

4. The method of claim 1, wherein the pharmaceutical composition is administered to the paediatric subject at an effective dose of 500 μg tetracosactide acetate.

5. The method of claim 1 wherein step iii) is performed 120 minutes after the intranasal administration of step ii).

6. The method of claim 1 wherein step iii) is performed 180 minutes after the intranasal administration of step ii).

7. A method of diagnosis of adrenal insufficiency in a neonate subject between 0-28 days old or an infant subject between 1 to 12 months old, comprising:
   i) obtaining a sample of saliva from the neonate or infant subject and measuring cortisone concentration in said saliva sample;
   ii) intranasally administering a pharmaceutical composition adapted for nasal administration comprising an effective dose of tetracosactide acetate, chitosan glutamate, and an acid, wherein said composition has a viscosity of between 10 to 300 mPAs;

iii) repeating step i);
   iv) comparing the concentration of cortisone in the saliva sample of step (i) with the cortisone concentration of step (iii); and
   v) identifying adrenal insufficiency in the neonate or infant subject.

8. The method according to claim 7, wherein step iii) is performed 5, 10, 15, 20, 30, 40, 45, 50, 60, 75, 90, 120 and/or 180 min after intranasal administration of the pharmaceutical composition of step ii).

9. The method according to claim 7, wherein step i) is repeated 2, 3, 4, or 5 times after intranasal administration of the pharmaceutical composition according to step ii).

10. The method according to claim 7, wherein said acid is acetic acid.

11. The method according to claim 7, wherein said pharmaceutical composition comprises an effective dose of between 100-1000 μg tetracosactide acetate.

12. The method according to claim 7, wherein said viscosity is between 20 to 200 mPa·s.

13. The method according to claim 12, wherein said viscosity is between 50 mPa·s to 100 mPa·s.

14. A method of diagnosis of adrenal insufficiency in a neonate subject between 0-28 days old or an infant subject between 1 to 12 months old, comprising:
   i) obtaining a saliva sample from the neonate or infant subject and measuring cortisone concentration in the saliva sample;
   ii) intranasally administering a pharmaceutical composition to the neonate or infant subject at a dose of between 500-1000 μg, wherein the pharmaceutical composition comprises:
   tetracosactide acetate 0.25% (w/v),
   chitosan glutamate 0.5% (w/v),
   sodium chloride 0.54% (w/v),
   benzalkonium chloride 0.015% (w/v),
   acetic acid 0.51% (w/v), and
   sodium acetate trihydrate 0.21% (w/v);
   iii) repeating step i);
   iv) comparing the concentration of cortisone in the saliva sample of step (i) with the cortisol or cortisone concentration of step (iii); and
   (v) identifying adrenal insufficiency in the neonate or infant subject.

15. The method of claim 1, wherein the pediatric subject is a neonate subject between 0-28 days old or an infant subject between 1 to 12 months old.

* * * * *